(12) United States Patent
Ketchel, III

(10) Patent No.: US 11,341,555 B2
(45) Date of Patent: May 24, 2022

(54) CREATING DIGITAL HEALTH ASSETS

(71) Applicant: MDSAVE SHARED SERVICES INC., Brentwood, TN (US)

(72) Inventor: Paul J. Ketchel, III, Nashville, TN (US)

(73) Assignee: MDSAVE SHARED SERVICES INC., Brentwood, TN (US)

( * ) Notice: Subject to any disclaimer, the term of this patent is extended or adjusted under 35 U.S.C. 154(b) by 0 days.

(21) Appl. No.: 17/368,927

(22) Filed: Jul. 7, 2021

(65) Prior Publication Data

US 2021/0342909 A1 Nov. 4, 2021

Related U.S. Application Data

(63) Continuation-in-part of application No. 17/209,117, filed on Mar. 22, 2021, now Pat. No. 11,170,423, (Continued)

(51) Int. Cl.
*G06Q 40/00* (2012.01)
*G06Q 30/06* (2012.01)
(Continued)

(52) U.S. Cl.
CPC ....... *G06Q 30/0621* (2013.01); *G06Q 20/065* (2013.01); *G06Q 20/10* (2013.01);
(Continued)

(58) Field of Classification Search
CPC .............. G06Q 40/00; G06Q 30/0621; G06Q 30/0206; G06Q 30/0239; G06Q 30/0613;
(Continued)

(56) References Cited

U.S. PATENT DOCUMENTS

| 7,034,691 B1 | 4/2006 | Rapaport |
| 7,895,061 B2 | 2/2011 | Schoenberg |

(Continued)

FOREIGN PATENT DOCUMENTS

| CA | 2447731 | 4/2005 |
| JP | 2003-22409 | 1/2003 |
| WO | 2018039312 | 3/2018 |

OTHER PUBLICATIONS

A survey of blockchain-based strategies for healthcare EJ De Aguiar, BS Faiçal, B Krishnamachari . . . —ACM Computing . . . , 2020—dl.acm.org (Year: 2020).*

(Continued)

*Primary Examiner* — Lalita M Hamilton
(74) *Attorney, Agent, or Firm* — Hollowell Patent Group; Kelly Hollowell

(57) ABSTRACT

Apparatus and associated methods relate to encoding a digital asset representing a service bundle, with parameters uniquely identifying the bundle, based on the bundle definition, and with a value and availability determined as a function of asset state. The bundle may include a health service. The encoded asset may be a digital asset token, configured in computing device memory, or transported via network, to transfer possession, transfer ownership, verify ownership, change state, or access a bundled service. The asset token may include individually manageable sub-tokens. The bundle definition may include a unique combination of facility, location, time, or professional resources allocated to provide a service. The bundle may be certified, based on verified funding or confirmed resource allocation. Asset class may be based on certification. The asset may be non-fungible based on the unique resource combination's inherently limited supply, permitting the bundle to have intrinsic value with a demand-based price.

28 Claims, 31 Drawing Sheets

Related U.S. Application Data which is a continuation of application No. 16/913,662, filed on Jun. 26, 2020, now Pat. No. 10,991,021, which is a continuation-in-part of application No. 16/685,888, filed on Nov. 15, 2019, now Pat. No. 11,030,666, which is a continuation-in-part of application No. 16/520,906, filed on Jul. 24, 2019, now Pat. No. 11,030,665, which is a continuation-in-part of application No. 15/055,076, filed on Feb. 26, 2016, now abandoned, which is a continuation-in-part of application No. 14/874,004, filed on Oct. 2, 2015, now abandoned, which is a continuation of application No. 14/827,026, filed on Aug. 14, 2015, now abandoned, which is a continuation-in-part of application No. 14/461,209, filed on Aug. 15, 2014, now Pat. No. 9,123,072.

(60) Provisional application No. 61/866,922, filed on Aug. 16, 2013.

(51) Int. Cl.
| | |
|---|---|
| *G06Q 50/22* | (2018.01) |
| *G06Q 30/02* | (2012.01) |
| *G06Q 20/06* | (2012.01) |
| *G06Q 20/10* | (2012.01) |
| *G06Q 20/38* | (2012.01) |
| *G16H 40/20* | (2018.01) |
| *G16H 10/60* | (2018.01) |
| *G16H 20/00* | (2018.01) |

(52) U.S. Cl.
CPC ....... *G06Q 20/381* (2013.01); *G06Q 30/0206* (2013.01); *G06Q 30/0239* (2013.01); *G06Q 30/0613* (2013.01); *G06Q 30/0629* (2013.01); *G06Q 30/0633* (2013.01); *G06Q 50/22* (2013.01); *G16H 10/60* (2018.01); *G16H 40/20* (2018.01); *G16H 20/00* (2018.01)

(58) Field of Classification Search
CPC ........... G06Q 30/0629; G06Q 30/0633; G06Q 50/22; G06Q 20/065; G06Q 20/10; G06Q 20/381; G06Q 20/00; G06H 40/20; G06H 20/00

See application file for complete search history.

(56) References Cited

U.S. PATENT DOCUMENTS

| | | | |
|---|---|---|---|
| 8,428,964 B2 | 4/2013 | Picken | |
| 8,494,881 B1 | 7/2013 | Wizig | |
| 8,612,267 B1 | 12/2013 | Shrivastava | |
| 9,123,072 B2 | 9/2015 | Ketchel, III | |
| 10,373,158 B1 | 8/2019 | James et al. | |
| 10,600,050 B1 | 3/2020 | Anton et al. | |
| 10,708,042 B1 | 7/2020 | Rubenstein et al. | |
| 11,012,429 B2 | 5/2021 | Dhanabalan et al. | |
| 11,126,593 B2* | 9/2021 | Hurley | G06F 16/9024 |
| 2002/0004782 A1 | 1/2002 | Cincotta | |
| 2002/0059082 A1 | 5/2002 | Moczygemba | |
| 2002/0065758 A1 | 5/2002 | Henley | |
| 2002/0103672 A1 | 8/2002 | Torres et al. | |
| 2003/0009402 A1 | 1/2003 | Mullen | |
| 2003/0018530 A1 | 1/2003 | Walker et al. | |
| 2005/0010440 A1 | 1/2005 | Merkin | |
| 2005/0021455 A1 | 1/2005 | Webster | |
| 2005/0075975 A1 | 4/2005 | Rosner | |
| 2007/0043595 A1 | 2/2007 | Pederson | |
| 2007/0088580 A1 | 4/2007 | Richards, Jr. | |
| 2007/0150986 A1 | 6/2007 | Jung | |
| 2009/0144088 A1 | 6/2009 | Zubiller | |
| 2009/0210251 A1 | 8/2009 | Callas | |
| 2010/0070295 A1 | 3/2010 | Kharraz Tavakol et al. | |
| 2010/0121727 A1 | 5/2010 | Butler | |
| 2010/0250271 A1 | 9/2010 | Pearce et al. | |
| 2010/0306013 A1 | 12/2010 | Mark | |
| 2011/0106593 A1 | 5/2011 | Schoenberg | |
| 2011/0145149 A1 | 6/2011 | Valdes et al. | |
| 2012/0053963 A1 | 3/2012 | Seymour | |
| 2012/0054119 A1 | 3/2012 | Zecchini | |
| 2012/0215563 A1 | 8/2012 | Lassen et al. | |
| 2012/0232936 A1 | 9/2012 | Bravata et al. | |
| 2012/0239560 A1 | 9/2012 | Pourfallah et al. | |
| 2012/0245953 A1 | 9/2012 | Morris | |
| 2013/0096937 A1 | 4/2013 | Campbell et al. | |
| 2013/0179194 A1 | 7/2013 | Lorsch | |
| 2013/0198025 A1 | 8/2013 | Picken | |
| 2014/0067406 A1 | 3/2014 | Hyatt et al. | |
| 2014/0149135 A1 | 5/2014 | Boerger et al. | |
| 2014/0195370 A1 | 7/2014 | Devasia | |
| 2014/0365240 A1 | 12/2014 | Canton | |
| 2015/0052009 A1 | 2/2015 | Ketchell, III | |
| 2015/0178808 A1 | 6/2015 | Grossman et al. | |
| 2015/0250271 A1 | 9/2015 | Ogilvie | |
| 2015/0294338 A1 | 10/2015 | Ketchel, III et al. | |
| 2015/0332283 A1 | 11/2015 | Witchey | |
| 2015/0356663 A1 | 12/2015 | Ketchel, III et al. | |
| 2016/0027085 A1 | 1/2016 | Ketchel, III et al. | |
| 2016/0253731 A1 | 9/2016 | Ketchel, III et al. | |
| 2018/0240191 A1 | 8/2018 | Aronson | |
| 2019/0266597 A1 | 8/2019 | Mohtar | |
| 2019/0333033 A1 | 10/2019 | Finlow-Bates | |
| 2019/0340946 A1 | 11/2019 | Elmessiry et al. | |
| 2019/0378121 A1 | 12/2019 | Marshall | |
| 2019/0378227 A1 | 12/2019 | Vanzetta | |
| 2020/0076884 A1 | 3/2020 | Li et al. | |
| 2020/0111092 A1 | 4/2020 | Wood et al. | |
| 2020/0134612 A1 | 4/2020 | Fostiropulo et al. | |
| 2020/0175506 A1 | 6/2020 | Snow | |
| 2020/0193764 A1 | 6/2020 | Ovalle | |
| 2020/0219089 A1 | 7/2020 | Crumb et al. | |
| 2020/0294038 A1 | 9/2020 | Kreiser et al. | |
| 2020/0294128 A1* | 9/2020 | Celia | H04L 9/0637 |
| 2020/0304518 A1 | 9/2020 | Thekadath et al. | |
| 2021/0065267 A1 | 3/2021 | Smith | |
| 2021/0082044 A1* | 3/2021 | Sliwka | G06Q 40/025 |
| 2021/0097484 A1 | 4/2021 | Ramos et al. | |
| 2021/0099313 A1 | 4/2021 | Kondrashov et al. | |
| 2021/0124722 A1 | 4/2021 | Srivastava | |
| 2021/0133735 A1 | 5/2021 | Maim | |
| 2021/0150653 A1 | 5/2021 | Hjertstedt | |
| 2021/0158441 A1 | 5/2021 | Celia | |
| 2021/0303519 A1* | 9/2021 | Periyagaram | G06F 16/119 |

OTHER PUBLICATIONS

ProQuest, "Medical Instruments & Supplies; MedAssets Addresses Payment Reform with Bundled Reimbursement Solution", Obesity, Fitness & Wellness Week, retrieved from <http://search.proquest.com/docview/732996687?1:Accountid=14753>, Aug. 7, 2010, 2 pages.

International Search Report and Written Opinion received for PCT Patent Application No. PCT/US2015/03/751, dated Sep. 17, 2015, 15 pages.

Extended European Search Report received for European Patent Application No. 14836898.8, dated Dec. 22, 2016, 9 pages.

Office Action (Communication pursuant to Article 94(3) EPC) received for EP Patent Application No. 14836898.8, dated Oct. 31, 2017, 10 pages.

Miller, Julie. Nimble Payment Models; Managed Healthcare Executive; Monmouth Junction vol. 20, Iss. 4, (Apr. 2010): 12-16. (Year: 2010).

Credit Management Tools.com: Credit Tools: Discount and Prepayment, 2009, pp. 1-3 (Year: 2009).

(56) References Cited

OTHER PUBLICATIONS

Zimmerman, John C, CPA. When Does Prepaying Expenses Accelerate Tax Deductions? Practical Tax Strategies; Boston vol. 79, Iss. 5, (Nov. 2007): 260-262,264-266. (Year: 2007).

* cited by examiner

| DHA Lifecycle State | State Description |
|---|---|
| Minting | New Digital Health Asset (DHA) Created |
| Issued | Created DHA Available for Trading |
| Trading | DHA Available for Purchase via Exchange |
| Sold | DHA Ownership Changed via Exchange |
| Redeemed | DHA Product Delivered or Service Provided |
| Burned | DHA Destroyed, Asset Liquidated Without Sale |

FIG. 1AD

| Action | State | Next State | Actor |
|---|---|---|---|
| Create | None | Minting | Asset Creator |
| Destroy | Minting | Burned | Asset Creator |
| Assign | Minting | Issued | Provider or Owner |
| Offer | Issued | Trading | Provider or Owner |
| Destroy | Issued | Burned | Asset Creator |
| Destroy | Trading | Burned | Asset Creator |
| Modify | Trading | Issued | Asset Creator |
| Sell | Trading | Sold | Asset Owner |
| Re-sell | Sold | Trading | Asset Owner |
| Redeem | Sold | Redeemed | Asset Owner, Provider |

| Asset ID |
| --- |
| Asset Class |
| Asset Creation Time |
| Asset Status Sequence ID |
| Issuer Public Key |
| Owner Public Key |
| Provider Public Key |
| DHA Header Hash |
| Owner-signed Header Hash |
| Issuer ID |
| Owner ID |
| Provider ID |
| Bundle ID |
| DHA Payload Hash |

| |
|---|
| Bundle ID |
| Product or Service ID |
| Provider ID |
| Location ID |
| Facility ID |
| Earliest Availability Time |
| Expiration Time |
| Contract Service Time |
| Contract |
| Sub-Bundle ID |

32

34

Patient Information

| Name | DOB | Phone Number | Email address |
|---|---|---|---|
| Sarah Doe | 08/23/1989 | 619-915-8150 | sample@sample.com |

Purchase Information

| Procedure | Provider | Phone Number |
|---|---|---|
| 29877 - Surgical arthroscopy of knee with chodroplasty (1) | John Smith | 1-877-461-2491 |
| 1382 Anesthesia for diagnostic arthroscopic procedure on knee (1) | David Jackson | 1-877-461-2491 |
| Facility Fee | Brentwood Surgery Center | 615-915-9330 |

Total Pre-Paid Price: $1554.1

How to use your MDSave Medical Voucher:
You have three different options to present this voucher to the receptionist at the time of your appointment.
1. Pull up your MDSave email receipt on your smart phone.
2. Write down the Confirmation Number and the Voucher Number.
3. Or Simply print this page and take the copy with you.

Pre-Paid Medical Voucher
Confirmation Number: 979110096
Voucher Number: 17605096
Order Date: 08/15/2013

PAYOUT RATES LISTED ARE SUGGESTED RATES ONLY. ALL RATES ARE TO BE DETERMINED BY THE HOSPITAL SYSTEM

| SPECIFIC LOCALITY | | | RECOMMENDED RATE | |
|---|---|---|---|---|
| FACILITY | ABILENE MEDICAL CENTER | 0.773 | FACILITY | 130% |
| PHYSICIAN | REST OF TEXAS | 0.97 | PHYSICIAN | 130% |

○ ANESTHESIA ● SEDACIAN ☐ PATHOLOGY          717    ✓ EXPAND ALL  ▲ COLLAPSE ALL  ☐ EXPORT TO EXCEL    ADVANCED

| PROCEDURE | REC. FACILITY PRICE | REC. PHYS. PRICE | PATHOLOGY PRICE | MDSAVE FEE | TOTAL AMOUNT |
|---|---|---|---|---|---|
| GI | | | | | |
| › COLONOSCOPY | $877.89 | $334.01 | $130.00 | $125.00 | $1,466.70 |
| › FLEXIBLE SIGNOIDOSCOPY | $704.39 | $143.19 | $130.00 | $125.00 | $1,102.58 |
| ⌄ TRANSNASAL ESOPHAGOSCOPY (TNE) | $837.38 | $119.03 | $0.00 | $125.00 | $1,081.41 |

| DESCRIPTION | CPT CODE | CMS FACILITY | CMS PHYSICIAN | FACILITY REC. RATE 130% | PHYSICIAN REC. RATE 130% | PATHOLOGY REC. RATE |
|---|---|---|---|---|---|---|
| ESOPHAGOSCOPY FLEX DOC BRUSH | 43197 | $745.60 | $85.81 | $837.38 | $108.21 | $0.00 |
| ESOPHAGOSCOPY FLEX TMSN BIOPY | 43198 | $745.60 | $102.97 | $837.38 | $129.03 | $0.00 |
| | | | AVERAGES $ | 837.38 | 119.03 | 0.00 |
| | | | | | $125.00 | 711d |

| PROCEDURE | REC. FACILITY PRICE | REC. PHYS. PRICE | PATHOLOGY PRICE | MDSAVE FEE | TOTAL AMOUNT |
|---|---|---|---|---|---|
| › ESOPHAGEAL MANOMETRY | $369.20 | $91.98 | $0.00 | $125.00 | $586.18 |
| › HEMORRHOID BANDING | $496.98 | $249.32 | $0.00 | $125.00 | $871.30 |
| › BRAVO 48 HOUR PH MONITOR | $369.20 | $107.31 | $0.00 | $125.00 | $601.51 |
| › ABDOMINAL PARACENTESIS | $549.59 | $120.15 | $130.00 | $125.00 | $924.74 |
| › HEMONHOIDECTOMY | $2,180.41 | $513.44 | $0.00 | $125.00 | $2,818.85 |
| › FEEDING TUBE PLACEMENT | $219.23 | $62.22 | $0.00 | $125.00 | $406.45 |
| › CAPSULE ENCLOSCOPY | $957.36 | $246.17 | $0.00 | $125.00 | $1,328.53 |
| › FEEDING TUBE PLACEMENT (PEG) | $1,195.94 | $275.48 | $0.00 | $125.00 | $1,596.42 |
| › UPPER ENDOSCOPY (EGD) | $892.54 | $224.78 | $0.00 | $125.00 | $1,242.32 |
| › EGD WITH COLONOSCOPY | $1,203.96 | $736.42 | $0.00 | $125.00 | $2,065.38 |

[EMAIL PRICES]  [SAVE CHANGES]  [TAKE LIVE]

FIG. 7C

CREATING DIGITAL HEALTH ASSETS

CROSS REFERENCE TO RELATED APPLICATIONS

This application is a continuation-in-part of pending U.S. application Ser. No. 17/209,117 filed Mar. 22, 2021, which is a continuation of U.S. application Ser. No. 16/913,662 filed Jun. 26, 2020, issued as U.S. Pat. No. 10,991,021 on Apr. 27, 2021, which is a continuation-in-part of U.S. application Ser. No. 16/685,888 filed Nov. 15, 2019, issued as U.S. Pat. No. 11,030,666 on Jun. 8, 2021, which is a continuation-in-part of U.S. application Ser. No. 16/520,906 filed Jul. 24, 2019, issued as U.S. Pat. No. 11,030,665 on Jun. 8, 2021, which is a continuation-in-part of U.S. application Ser. No. 15/055,076 filed Feb. 26, 2016, which is a continuation-in-part of U.S. application Ser. No. 14/874,004 filed Oct. 2, 2015, which is a continuation of U.S. application Ser. No. 14/827,026 filed Aug. 14, 2015, which is a continuation-in-part of U.S. application Ser. No. 14/461,209 filed Aug. 15, 2014, issued as U.S. Pat. No. 9,123,072 on Sep. 1, 2015, which claims the benefit of Provisional Appl. 61/866,922 filed Aug. 16, 2013, the contents of which are all incorporated herein in their entirety by reference thereto.

TECHNICAL FIELD

Various embodiments relate generally to medical care.

BACKGROUND

Medical services are services provided to a medical patient. Some medical services may help improve or maintain a patient's health, based on disease prevention, diagnosis, or treatment. A medical service may be provided by a doctor licensed to practice medicine. The practice of medicine encompasses medical procedures performed for a patient, which may include both preventive care and treatment. A medical doctor may provide preventive care and treatment through a medical practice provisioned with diagnostic and treatment facilities. For example, a medical practice may provide preventive care and treatment services through the work of trained or licensed medical professionals in a medical facility.

Medical service providers include doctors, hospitals, and health insurers. A provider may offer medical services to patients by provisioning medical resources such as, for example, laboratory, imaging, treatment, or surgical facilities, to provide the services. Some medical services may require specially trained or licensed medical professionals. For example, a medical practice providing diagnosis and treatment for joint pain may provide medical services through the work of an orthopedic specialist. In some scenarios, patient access to a specialized professional or facility may be limited by cost, or availability. Some specialized medical professionals and related facilities may be scarce.

A medical practice may limit the medical procedures offered to patients based on the availability of specialized professionals and facilities at a given time or location. For example, the services offered to a patient may be determined based on allocating surgeons to various surgical facility locations at specific times. Services supplied to patients may be limited to the allocated medical professionals and facilities, even when medical service demand exceeds supply at a given location or time. A medical practice providing many types of medical services may expend significant resources adapting the offered services to demand as cost and demand change. Some medical practices may fail to capture potential revenue lost when resources to provide medical services are underutilized relative to medical service demand.

The price of healthcare services varies depending on specialty, procedure, and physician practice. In the United States, many patients do not have access to a simple way to shop and compare the price of common medical procedures. Due to the current managed care-based payor system in the US, the cost of treatment is often determined by managed care organizations.

These managed care organizations have specific formularies for drugs and procedures designed specifically to patients' individual health plans, which restrict the drugs and procedures available to patients in their particular plans. Patients have historically had no access to these price lists or formularies and have had very few tools to assist them in finding and comparing health care services or predetermining the cost of a procedure. Currently prospective patients who chose to compare medical costs are forced to conduct extensive, often inefficient, and time-consuming research to compare medical procedures prior to treatment.

The rising cost of healthcare is having a dramatic effect on the U.S. healthcare system. Healthcare costs continue to outpace pace inflationary growth, provider reimbursement rates continue to fall, and the cost of patient insurance premiums are increasing. To lower monthly premium costs, many patients are choosing to purchase (and employers are choosing to offer) high deductible health plans as an alternative to traditional higher premium PPO health plans.

These high deductible plans require patients to pay cash payments for medical services until the high deductible is satisfied, and once this deductible has been met, the insurance carrier begins to cover medical costs. As a result, many patients are seeing exponential increases in out-of-pocket expenses for medical procedures and services. In addition to more patients selecting high deductible plans, many patients cannot afford increased payments and are becoming uninsured or underinsured. As the number of patients who are uninsured, underinsured, or on high deductible plans grows, the need for a mechanism that allows patients to find discounted medical services increases and an efficient payment system.

SUMMARY

Apparatus and associated methods relate to encoding a digital asset representing a service bundle, with parameters uniquely identifying the bundle, based on the bundle definition, and with a value and availability determined as a function of asset state. The bundle may include a health service. The encoded asset may be a digital asset token, configured in computing device memory, or transported via network, to transfer possession, transfer ownership, verify ownership, change state, or access a bundled service. The asset token may include individually manageable sub-tokens. The bundle definition may include a unique combination of facility, location, time, or professional resources allocated to provide a service. The bundle may be certified, based on verified funding or confirmed resource allocation. Asset class may be based on certification. The asset may be non-fungible based on the unique resource combination's inherently limited supply, permitting the bundle to have intrinsic value with a demand-based price.

In an aspect, an apparatus is disclosed, comprising: a processor; and, a memory, operably coupled with the processor, wherein the memory encodes processor executable program instructions and data to program and configure the processor to cause the apparatus to perform operations comprising: receive an electronic message comprising a service definition; determine a resource available to provide a service, based on the service definition; create an asset comprising the resource and the service; and, encode the asset in a digital asset token.

The operations performed by the apparatus may further comprise broadcast the digital asset token to a DL (Distributed Ledger).

The service definition may further comprise a service type.

The service definition may further comprise a location and time.

Determining the resource available to provide the service may further comprise determining if a smart contract obligating the resource to provide the service exists.

Creating the asset may further comprise creating a smart contract obligating the resource to provide the service.

The operations performed by the apparatus may further comprise broadcasting to a DL the created asset degree of certification determined as a function of the smart contract.

The service may further comprise a healthcare service.

The service may further comprise a service bundle including a plurality of services.

In another aspect, an apparatus is disclosed, comprising: a processor; and, a memory, operably coupled with the processor, wherein the memory encodes processor executable program instructions and data to program and configure the processor to cause the apparatus to perform operations comprising: receive an electronic message comprising a request to create a service bundle digital asset, wherein the request comprises a service bundle definition, wherein the service bundle definition comprises a plurality of definitions for requested services, and wherein each definition of the plurality of definitions for requested services comprises a service type, a requested resource to perform the service, and a location and time associated with the service; determine for each requested resource if a smart contract exists obligating the resource to perform the service; in response to determining a smart contract exists obligating every one of the requested resources to each perform their respective service, send an electronic message comprising a rejection of the request to create the service bundle digital asset; in response to determining a smart contract exists obligating at least one but not all of the requested resources to each perform their respective service, send an electronic message comprising a rejection of the request to create the service bundle digital asset and an offer comprising an alternative service bundle; in response to determining no smart contract exists obligating any requested resource to perform the service: create an asset comprising the resources and the services; create a smart contract obligating each resource to provide their respective service; encode the asset and contracts in a digital asset token; broadcast the digital asset token to a DL; and, broadcast to a DL the created asset degree of certification determined as a function of the smart contracts.

The service bundle may further comprise a healthcare service.

The resource may further comprise a doctor.

The smart contract may be configured to pay the doctor when the doctor performs the service.

The smart contract may be configured to pay the doctor before the doctor performs the service.

The asset degree of certification may be determined as a function of the fraction of smart contracts encoded by the asset that obligate a resource to provide the service.

The alternative service bundle may further comprise a service selected as a function of the published contract status of the resources required to provide the service.

In another aspect, an apparatus is disclosed, comprising: a processor; and, a memory, operably coupled with the processor, wherein the memory encodes processor executable program instructions and data to program and configure the processor to cause the apparatus to perform operations comprising: receive an electronic message comprising a request to create a health service bundle digital asset, wherein the request comprises a health service bundle definition, wherein the service bundle definition comprises a plurality of definitions for requested healthcare services, and wherein each definition of the plurality of definitions for requested services comprises a service type, a requested resource to perform the service, and a location and time associated with the service; determine for each requested resource required to provide the service if a smart contract exists obligating the resource to perform the service, wherein the resource is determined required based on a non-fungible property definition received in an electronic message for the service bundle; in response to determining a smart contract exists obligating every one of the required resources to each perform their respective service, send an electronic message comprising a rejection of the request to create the service bundle digital asset; in response to determining a smart contract exists obligating at least one but not all of the required resources to each perform their respective service, send an electronic message comprising a rejection of the request to create the service bundle digital asset and an offer comprising an alternative service bundle; in response to determining no smart contract exists obligating any required resource to perform the service: create an asset comprising the resources and the services; create a smart contract for each resource obligating each resource to provide their respective service, wherein the smart contract is configured to pay the resource when the resource performs the service; encode the asset and contracts in a digital asset token; broadcast the digital asset token to a DL; and, broadcast to a DL the created asset degree of certification determined as a function of the smart contracts.

The created asset may further comprise an asset class value determined as a function of the asset degree of certification.

The request to create the health service bundle digital asset may further comprise the alternative service bundle definition sent with the electronic message comprising a rejection of the request.

The created asset may encode the alternative service bundle.

Various digital assets may achieve one or more advantages. For example, some digital assets may improve a user's access to affordable health services. This facilitation may be a result of increasing competition among providers to offer bundled health services represented by a digital asset token priced based on market demand. In some digital assets, custom service bundles may be configured based on sub-tokens that are individually manageable. Such individual management of customized service bundle assets based on sub-tokens may reduce transaction costs and increase availability of customized services. Some digital assets may have an intrinsic value derived from the unique physical resources allocated to provide a service represented by the asset. Such a unique asset having an intrinsic value derived from tangible resources may be a non-fungible asset, with a value based on the asset's inherently limited supply. For example, an asset with intrinsic value initially derived from the cost of allocating a doctor to provide a service during a facility time slot may be subsequently sold or traded for a price based on demand.

In some digital assets, the effort required by a user to manage their healthcare may be reduced. Such reduced healthcare management effort may be a result of a digital health asset that may be transferred, permitting users to buy, sell, and trade individual services as the user's needs change. Some digital assets may improve geographic portability of healthcare. Such improved geographic health care portability may be a result of a digital asset having an intrinsic value that can be the basis for exchanging assets to a obtain a different service, even in a geographic region having different service cost. Some digital assets may represent services certified based on verified funding or confirmed allocation of resources to provide the service at a specific location or time. Such a certified digital asset may trade at a valuation higher than an asset that is not certified, as a result of the allocated capability to provide the service.

Apparatus and associated methods relate to a digital token encoding an asset, based on a header uniquely identifying the asset and an asset payload encoding asset parameters including a unique reference to the header. In an illustrative example, the asset may be a healthcare service. The parameters may include, for example, service type, and a facility or professional to provide the service at a location or time. The header may be stored or transmitted separately from the payload, permitting efficient token storage and communication. In some examples, the header may include a mutable asset state value in an otherwise immutable header, permitting an efficient test to determine if an asset has been redeemed. Some tokens may encode a contract that may bind a party to provide an asset bundle. Various tokens may advantageously provide efficient verification of asset state, asset bundle status, and asset class determination based on contract status.

In an aspect, a digital asset token is disclosed, comprising: a header, encoding: an immutable asset identifier; an immutable exchange identifier; an immutable asset creation time; and, a mutable asset state value.

The asset identifier may be unique within a predetermined namespace.

The exchange identifier may be unique within a predetermined namespace.

The asset state value may be selected from the group consisting of minting, issued, trading, sold, redeemed, and burned.

The digital asset token may further comprise a payload encoding a unique reference to the header.

The unique reference to the header may further comprise: a copy of the asset identifier encoded by the header; the hash of the header; and, a nonce.

The payload may further comprise a reference to an asset.

The payload may further comprise a reference to a contract related to the asset.

The payload may further comprise an asset class value determined as a function of the contract status.

In another aspect, a digital asset token is disclosed, comprising: a header, encoding: an immutable asset identifier, wherein the asset identifier is unique within a predetermined namespace; an immutable exchange identifier, wherein the exchange identifier is unique within a predetermined namespace; an immutable asset creation time; and, a mutable asset state value selected from the group consisting of minting, issued, trading, sold, redeemed, and burned; and, a payload, encoding: a copy of the asset identifier encoded by the header; the hash of the header; a reference to an asset bundle; a reference to a contract defining asset bundle provision terms; an asset class determined as a function of the contract status; and, a nonce.

The asset bundle may further comprise a healthcare service.

The contract may encode a location and time associated with the healthcare service.

The healthcare service may be a primary healthcare service.

The asset bundle may further comprise a secondary healthcare service related to the primary healthcare service.

The asset bundle may further comprise a plurality of related asset bundles.

Each asset bundle of the plurality of related asset bundles may further comprise a subcontract encoding a location, time, facility, and professional resource allocated to provide the asset bundle.

In another aspect, a digital asset token is disclosed, comprising: a header, encoding: an immutable asset identifier, wherein the asset identifier is unique within a predetermined namespace; an immutable exchange identifier, wherein the exchange identifier is unique within a predetermined namespace; an immutable asset creation time; and, a mutable asset state value selected from the group consisting of minting, issued, trading, sold, redeemed, and burned; and, a payload, encoding: a copy of the asset identifier encoded by the header; the hash of the header; a reference to a plurality of related asset bundles, wherein each asset bundle of the plurality of related asset bundles comprises at least one healthcare asset; a reference to a contract defining provision terms of the related asset bundles, wherein the contract comprises one or more subcontract encoding a location, time, facility, and professional resource allocated to provide each of the at least one healthcare asset of the related asset bundles; an asset class determined as a function of contract status; and, a nonce.

The header and payload may be stored separately.

The asset class may be based on the fraction of subcontracts binding a party to provide an asset.

The contract may comprise a smart contract.

In an aspect, an apparatus may comprise: a processor; and a memory configured to be operably coupled to the processor, wherein the memory comprises encoded data and processor executable program instructions, wherein the data and instructions jointly configure and program the apparatus that the instructions when executed by the processor cause the apparatus to perform operations comprising: receive a service offer from a service provider; and construct in the memory a digital asset token for the service offer, the digital asset token comprising: a header, encoding: an immutable asset identifier representing the service offer; an immutable asset exchange identifier; an immutable asset creation time representing the time at which the digital asset token was constructed; a mutable asset state value representing the minting state; a payload, encoding; the service offer; a copy of the asset identifier encoded by the header; the hash of the header; a nonce; send the header without the payload to a first application server; and send the payload without the header to a second application server.

The asset identifier may be unique within a predetermined namespace.

The exchange identifier may be unique within a predetermined namespace.

The operations performed by the apparatus may further comprise: in response to receiving payment for the digital asset, set the state value to sold.

The service offer may further comprise the service offer encoding a plurality of references to a respective plurality of smart contracts, and wherein the operations performed by the apparatus may further comprise broadcast to a Distributed Ledger (DL) the asset degree of certification determined as a function of the fraction of the smart contracts that obligate at least one resource to provide at least one service associated with the service offer.

The service offer may further comprise a price.

The service offer may further comprise identification of a named healthcare service provider such as a named physician, group, practice, facility, or hospital system.

The payload may further comprise a reference to a contract related to the named healthcare service provider such as the named physician, group, practice, facility, or hospital system.

The payload may further comprise an asset class value determined as a function of the contract status.

The service offer may further comprise: a reference to a service bundle; a reference to a contract defining service bundle provision terms, and an asset class value determined as a function of the contract status.

The service bundle may further comprise a healthcare service.

The contract may encode a location and time at which the healthcare service will be performed.

The healthcare service may be a primary healthcare service.

The service bundle may further comprise a secondary healthcare service related to the primary healthcare service.

The service bundle may further comprise a plurality of related service bundles.

Each service bundle of the plurality of related service bundles may further comprise a subcontract encoding a location, time, facility, and professional resource allocated to provide the service bundle.

In another aspect, an apparatus may comprise: a processor; and a memory configured to be operably coupled to the processor, wherein the memory comprises encoded data and processor executable program instructions, wherein the data and instructions jointly configure and program the apparatus that the instructions when executed by the processor cause the apparatus to perform operations comprising: receive a service offer from a service provider; and construct in the memory a digital asset token for the service offer, the digital asset token comprising: a header, encoding: an immutable asset identifier representing the service offer, wherein the asset identifier is unique within a predetermined namespace; an immutable asset exchange identifier, wherein the exchange identifier is unique within a predetermined namespace; an immutable asset creation time representing the time at which the digital asset token was constructed; a mutable asset state value representing the trading state; a payload, encoding: the service offer; a copy of the asset identifier encoded by the header; the hash of the header; a reference to an asset bundle; a reference to at least one contract defining asset bundle provision terms; an asset class determined as a function of the contract status; a nonce; send the header without the payload to an asset exchange identified by the asset exchange identifier; and broadcast to a DL the asset degree of certification determined as a function of the fraction of the at least one contract that obligates at least one resource to provide at least one service associated with the service offer.

The asset bundle may further comprise a healthcare service.

The contract may encode a procedure, a location, and a time associated with the healthcare service.

The healthcare service may be a primary healthcare service.

The asset bundle may further comprise a secondary healthcare service related to the primary healthcare service.

The asset bundle may further comprise a plurality of related asset bundles.

Each asset bundle of the plurality of related asset bundles may further comprise a subcontract encoding a location, time, facility, and professional resource allocated to provide a service included with the asset bundle.

In another aspect, an apparatus may comprise: a processor; and a memory configured to be operably coupled to the processor, wherein the memory comprises encoded data and processor executable program instructions, wherein the data and instructions jointly configure and program the apparatus that the instructions when executed by the processor cause the apparatus to perform operations comprising: receive a service offer from a service provider; and construct in the memory a digital asset token for the service offer, the digital asset token comprising: a header, encoding: an immutable asset identifier representing the service offer, wherein the asset identifier is unique within a predetermined namespace; an immutable asset exchange identifier, wherein the exchange identifier is unique within a predetermined namespace; an immutable asset creation time representing the time at which the digital asset token was constructed; a mutable asset state value selected from the group consisting of minting, issued, trading, sold, redeemed, and burned; a payload, encoding: the service offer; a copy of the asset identifier encoded by the header; the hash of the header; a reference to a plurality of related asset bundles, wherein each asset bundle of the plurality of related asset bundles comprises at least one healthcare asset; a reference to at least one contract defining provision terms of the related asset bundles, wherein the at least one contract comprises one or more subcontract encoding a location, time, facility, and professional resource allocated to provide each of the at least one healthcare asset of the related asset bundles; an asset class determined as a function of contract status; a nonce; and send the header without the payload to an asset exchange identified by the asset exchange identifier, and send the payload without the header to an application server.

The operations performed by the apparatus may further comprise: receive a digital asset token representing a certified service bundle digital asset having a current degree of certification; determine if the status of at least one contract changed, based on contract status received in response to a contract status query comprising the asset identifier; in response to determining the status of the at least one contract changed, determine an updated asset degree of certification based on the fraction of the at least one contract that obligates at least one resource to provide at least one asset; and broadcast the updated asset degree of certification to a DL with the asset identifier.

The asset class determined as a function of contract status may further comprise the asset class based on the fraction of subcontracts binding a party to provide an asset, and wherein the contract comprises a smart contract.

In another aspect, an apparatus may comprise: a processor; and a memory configured to be operably coupled to the processor, wherein the memory comprises encoded data and processor executable program instructions, wherein the data and instructions jointly configure and program the apparatus that the instructions when executed by the processor cause the apparatus to perform operations comprising: receive a digital asset token representing a certified service bundle digital asset having a current asset degree of certification, wherein the received digital asset token encodes a reference to at least one contract of a plurality of contracts, and wherein the at least one contract obligates at least one resource to provide at least one service related to the service bundle digital asset; determine if the status of the at least one contract changed, based on updated contract status received in response to a query comprising a service bundle digital asset identifier that uniquely identifies the service bundle digital asset within a predetermined namespace; in response to determining the status of the at least one contract changed, determine an updated asset degree of certification that is distinct from the current degree of certification, wherein the updated asset degree of certification is based on the updated fraction of the at least one contract that obligates at least one resource to provide at least one service related to the service bundle; and broadcast to a DL the updated asset degree of certification and the asset identifier.

The query comprising the service bundle digital asset identifier may be sent to and received by an application server.

The application server receiving the query comprising the service bundle digital asset identifier may host one or more DL node.

The service bundle digital asset may further comprise an asset class value determined as a function of the updated fraction of the at least one contract that obligates at least one resource to provide at least one service related to the service bundle.

The updated asset degree of certification may represent an asset that is more fully certified than the current asset degree of certification.

The digital asset token may further comprise: a header; and a payload, wherein the payload comprises a copy of an identifier encoded by the header; and the operations performed by the apparatus to receive the digital asset token may further comprise: associate, based on the identifier, the header received without the payload from a first application server with the payload received without the header from a second application server.

The first application server may host at least one DL node.

The second application server may host at least one DL node.

Various digital asset tokens may achieve one or more advantages. For example, some digital asset tokens may improve a user's ease of access to health care services. This facilitation may be a result of reducing a service provider's effort to determine if an asset token has been redeemed, based on a mutable asset state encoded in an otherwise immutable token header. Some digital asset tokens may reduce health care transaction effort or cost. Such reduced transaction effort or cost may be a result of a digital asset token including a header that may be stored or transmitted separately from the payload, permitting efficient token header storage and communication. Various digital asset tokens may include related healthcare services in an asset bundle scheduled for delivery at a contracted location and time. Such bundled healthcare assets may reduce a user's exposure to inflation or lack of predictability related to healthcare service cost. Some digital asset tokens may improve a service provider's capability to offer more services. This facilitation may be a result of improving the healthcare market's flexibility to adjust more quickly to supply and demand, based on trading digital asset tokens.

Some digital asset tokens may improve asset trading efficiency. Such improved asset trading efficiency may be a result of an asset class variable dynamically determined as a function of asset bundle subcontract status, permitting the market to determine asset value as parties become contractually bound to provide services.

A Digital Health Asset (DHA) may be a digital token encoding an asset, based on a header uniquely identifying the asset and an asset payload encoding asset parameters including a unique reference to the header. A DHA may exist in various states during the DHA lifecycle. A DHA may be created, traded, sold, and resold. The DHA header encodes information uniquely identifying a DHA throughout the DHA lifecycle. The DHA payload includes information encoding identification of an asset bundle and a unique reference to the DHA header. Each asset bundle encoded by the DHA payload may include a sub-bundle of related assets and a contract to provide the assets. One or more contract may be a smart contract. Only the header needs to be stored, transmitted, or evaluated, to perform a DHA operation with reference to the associated DHA token payload, which may be stored separately, for example in one or more database.

Once created, all DHA token header data fields except the asset state are immutable. In the DHA token header, the asset state is mutable, permitting efficient verification that a particular DHA has not been redeemed. In an illustrative example, multiple copies of different DHA in various DHA lifecycle states may exist. DHA may be stored and transactions may be verified by consensus on a DL (Distributed Ledger) using techniques known in the DLT (Distributed Ledger Technology) arts. Each DHA may appear multiple times in one or more DL.

For example, to determine if any DL has a particular DHA in redeemed state, relevant DL could be configured with a Bloom filter adapted to predict if the hash of the redeemed DHA is present in the DL: the presented DHA could be copied and the DHA copy's state set to redeemed, and the modified DHA copy hashed; then, the relevant DL Bloom filters could be queried to predict the presence of the DHA in the redeemed state, providing an efficient prediction of the DHA redemption status to permit rapid provider or purchaser validation before the provider delivers a product or service represented by the DHA. In some cases, the Bloom filter may be regenerated as the number of DHA or DHA transactions increase, to maintain effectiveness of DHA redemption status prediction.

A complete DHA encoded by a DHA token may be formed from a combination of the DHA token header and DHA token payload. The complete DHA formed from the header and payload may be stored on a user's computing device, or encoded in a physical token such as a chip card configured to authenticate write access to the DHA encoded in the card. For example, a provider could authenticate to obtain write access to modify a user's DHA, or to mark the DHA as redeemed when service is provided.

A DHA encodes asset parameters including a service or product, and asset state. Bid or ask prices associated with trading DHA may not be encoded by DHA, but instead such bid or ask prices may be encoded in a stream of transaction records which may be accessible through an exchange configured to facilitate trading DHA. A DHA may be sold multiple times.

A DHA may be created by an issuer. The issuer may be a provider, such as a doctor, hospital, or clinic. The issuer may create a DHA representing a procedure, service, or product to be provided. At creation time, the DHA is encoded with the creation time, a globally unique asset identifier, and a globally unique exchange identifier. At creation time, the DHA is encoded with an asset class that may conditionally permit various operations on a DHA or define various terms or conditions associated with the DHA, for example, some DHA asset classes may have different redemption, fulfillment guarantee, or expiration policies.

Upon DHA creation, the issuer or creator signs the DHA token header hash. DHA user registration includes uploading a public key to a key server accessible to participants. An issued DHA may be traded. DHA trading may include a sequence of transactions comprising a DHA transaction stream of transactions on DHA headers. DHA trading stream observers may obtain the asset data underlying the DHA from a DL accessible to all participants, based on the asset identifier. The DHA trading stream DL may be accessible through an exchange.

When a DHA is modified, the participant modifying the DHA increments the payload nonce sequence number, hashes the DHA token header, signs the DHA token header hash with their private key, and stores a copy of the DHA token payload including the signed DHA token header hash on the trading stream DL.

To record a DHA transaction, the buyer imports from a key server the public key of the purported owner, verifies the owner signature, updates the payload nonce sequence number, hashes the DHA token header, signs the DHA token header hash, stores the signed DHA token header hash and the buyer's public key in the token payload, and stores a copy of the token payload on the trading stream DL.

DHA transactions may be verified based on hashing each token header in a DHA trading stream and verifying the owner signature and nonce sequence number for that copy of the DHA at that point in time. In an illustrative example, the DHA payload having the greatest verified nonce sequence number and greatest modified time stamp will be the consensus current DHA. When consensus as to the owner and DHA state are determined between participants and an exchange, smart contracts encoded by the exchange may be enabled to execute if appropriate conditions are satisfied.

A service bundle digital asset (also referred to as a DHA) may be encoded by a digital asset token implementation complying with the EIP-721/ERC-721 Non-Fungible Token Standard. The digital asset token may encode a contract governing the asset. For example, the contract governing the asset may define terms, conditions, or actions controlling asset ownership, transfer, or delivery. The contract governing the asset may be a smart contract as would be known to one of ordinary skill in the arts related to DL technology.

DL and related technologies may be known to one of ordinary skill as blockchain. A DL implementation may include one or more computer-implemented node configured to process digital asset tokens, related smart contracts, and transactions associated with the tokens and contracts. An exemplary DL system may include more than one DL providing access to the historical record of tokens, transactions, and contracts, permitting multiple entities to reach consensus in matters concerning token and contract status. The smart contract governing the asset may include more than one smart contract. One or more smart contract governing the asset may be configured to execute at various times. One or more smart contract governing the asset may be configured to execute in response to various conditions. The multiple smart contracts governing the asset may include a smart contract configured to trigger or invoke the evaluation or execution of another smart contract if predetermined conditions are satisfied. For example, a smart contract may be configured to execute operations including completing a purchase by transferring funds, confirming a predetermined fund balance is available, determining the state of a contract, or confirming the availability of a contracted resource.

A digital asset token is the fundamental unit of DHA representation. A digital asset token may encode a contract, service, transaction, status, signature, or certification related by unique asset ID to a specific service bundle digital asset. A digital asset token encoding a contract, service, transaction, or status related to a service bundle digital asset may be broadcast to one or more DL, permitting multiple entities to confirm digital asset token status by consensus. A digital asset token may encode an updated DHA status, based on creating a digital asset token encoding updated information related to a primary asset by the primary asset's unique ID. The digital asset token may encode an updated DHA status based on adding, deleting, or modifying a token, sub-token, or contract to the DHA. The digital asset token adding, deleting, or modifying a token, sub-token, or contract may be broadcast to one or more DL, permitting multiple marketplace participants to reach consensus determination of the updated DHA status.

A service bundle digital asset may be encoded by multiple digital asset tokens related by unique asset ID to a primary asset. Each digital asset token encoding a service bundle digital asset may encode various service bundle features. A service bundle digital asset may be created, with a digital asset token encoding a unique asset id, a service type, location, and time. The service encoded by a digital asset token may be a primary service. The tokens and sub-tokens collectively representing the asset may be broadcast to a DL for access by market participants including providers, consumers, administrators, or insurers.

A digital asset token may be created to encode a sub-token related to the primary service asset token. The sub-token may encode a secondary service. The secondary service sub-token may be linked to the primary service asset by encoding the primary service asset unique ID in the secondary digital asset sub-token. The sub-token linked to the primary service asset may be broadcast to one or more DL, permitting market participants to reach consensus status determination for the asset including related contract, secondary service, or sub-tokens, based on processing the related tokens encoded by one or more DL. The sub-token may include a sub-token, related by the asset unique ID.

A digital asset token may be created to encode a contract governing the primary service asset. The contract may be linked to the primary service asset by encoding the primary service asset unique ID in the contract digital asset token. The contract linked to the primary service asset may be broadcast to one or more DL, permitting market participants to reach consensus status determination for the contract and the related asset by processing the tokens encoded by one or more DL. The contract digital asset token may include a sub-contract, related by the asset unique ID.

Each service included in a service bundle may be encoded in a token or sub-token, with parameter values assigned to represent each resource required to deliver each service. Such a digital asset token may be constructed to represent complex medical procedures or episodes of care, based on combining a series of distinct sub-procedures and services represented as tokens and sub-tokens encoding contracts governing provider service delivery. The provider services may be performed using provider assets, including, for example, facility locations, time slots allocated or assigned for facility or professional engagement, equipment, or other resources. The provider resources may be bound by contract, for example in the case of a professional services smart contract obligating a professional to provide a particular service at a predetermined location and time. The provider resource may be bound by funding, for example, in the case of a pre-paid professional service. In some cases, a resource may be bound by funds to pay for the services offered by the provider. The funds to pay for the services may be deposited in a sub-account controlled by the provider and linked to the resource, permitting the resource to access the funds when the service by the resource is complete. In any case, each service offered by a provider may be bound by contract or funding. In an illustrative example, a smart contract encoded by a token or sub-token may encode an agreement governing how a single payment is apportioned among a group, permitting easier coordination among groups of otherwise unaffiliated providers.

A contract or smart contract encoded by a digital asset token or sub-token may exist in various states based on agreement of various parties. For example, the contract or smart contract may be signed by a provider and sub-provider agreeing to the terms of service offered to a consumer. The contract may be signed by a consumer when the consumer purchases the contracted service, obligating the provider and sub-provider to perform the service. The provider may be a medical practice, and a sub-provider may be a medical doctor contractually obligated to provide service. Some contracts encoded by a digital asset token may be finalized outside of a DL with the resulting contract status update broadcast to a DL, permitting consensus contract status verification.

A service bundle digital asset may be a non-fungible asset defined by a unique non-reproducible physical element combination. The non-fungible property of a service bundle digital asset may be enforced during asset creation, such that an attempt to replicate the asset's unique physical element combination will fail. For example, a non-fungible service bundle digital asset may be uniquely defined by a combination of physical elements such as service type, service provider, professional resource, location, and time. In an illustrative example, such a particular combination of specific elements may be unique, permitting the service bundle digital asset to be non-fungible as a result of uniqueness. The non-fungible property of such a service bundle digital asset may be enforced during asset creation based on verifying the contract status for each resource needed to provide the service.

A service provider may determine the set of elements defining the non-fungible property of a service bundle digital asset. For example, a service provider may identify the set of elements defining a service bundle digital asset's non-fungible property. The service provider may publish a digital asset token encoding the asset's non-fungible definition to a DL. The digital asset token encoding the asset's non-fungible definition may include the asset's unique ID. The published non-fungible definition may permit marketplace participants to reach consensus concerning the asset value, based on the non-fungibility of the asset's required elements. The service provider may create and broadcast to one or more DL a digital asset token encoding a reference to each sub-token that encodes a sub-service required to perform the primary service, permitting marketplace participants to determine by consensus the smart contract status of the resources required to provide a service.

In an illustrative example, market participants with access to the published smart contract status of the resources required to provide a service may assess the value of an asset based on the value of the required services allocated to or obligated to perform the service. For example, each required sub-service may be supported by a contract or smart contract obligating one or more provider or sub-provider to perform a service required by the primary service. A required service may be a doctor, technician, equipment, facility, or support staff, obligated by contract to provide service at a specific location and time. In an illustrative example, each required resource associated with a contract agreed to by all parties will have been verified as obligated to perform the service. The non-fungible property of such a service bundle digital asset may be enforced during asset creation by verifying the contract status of each resource required to deliver a service bundle. For example, asset creation may include determining if the unique asset already exists, based on recursively evaluating the status of all contracts or subcontracts related to an asset. In an illustrative example, if all required resources are already obligated by contract to deliver a service bundle that conflicts by location or time with a requested service bundle, asset creation for the requested service bundle may fail. For example, a provider may define as required a particular facility, procedure, and time, leaving the attending doctor as a variable, and permitting a creation of a non-fungible asset defined by the facility, procedure, and time parameters. Asset creation may include negotiation procedures designed to permit creation of alternative assets, in the case when asset creation fails as a result of an attempt to replicate a non-fungible asset. Enforcing the non-fungible property of a service bundle digital asset during an exemplary asset creation process may permit asset valuation based on the value of the underlying services obligated by contract to perform the service.

A service bundle digital asset may be certified, to support the asset value based on confirmed availability of the bundled services. A service bundle digital asset may be certified based on verifying a contracted obligation to perform or deliver each service or sub-service related to the asset. For example, certifying a service bundle may include recursively engaging or signing a contract obligating the provider of each service included in a service bundle to perform or deliver the service. An asset may be determined to be a certified asset if a contract obligates each sub-service or resource required to deliver the bundled services. The contract may encode a specific location, time, facility, or professional to provide the service. A service bundle digital asset may be certified at the sub-token, or sub-service level. A service bundle digital asset may be certified based on verifying funding allocated to pay a provider or sub-provider to perform a service. For example, a smart contract may be configured to monitor funding allocated to a sub-account, to verify funds are available to pay a sub-provider when the sub-provider performs a service. The smart contract monitoring funding allocated to the sub-account may be configured to revoke other contracts, notify asset owners, or update asset status to one or more DL if the monitored funds are withdrawn or are reduced below a predetermined funds balance.

Certification of a service underlying a service bundle digital asset may permit valuation of the asset based on the obligated resources or verified funding. In an illustrative example, a service bundle digital asset may be partially certified, based on verifying a contract exists that obligates a resource to provide a service. Contract verification may be determined for a resource at the sub-token level of a service bundle digital asset. For example, a service bundle digital asset may encode contracts agreed to for some, but not all services of a service bundle. A service bundle digital asset may encode contracts obligating a facility to perform a service at a contracted time, without a contract obligating a doctor to perform that particular service. Such a service bundle digital asset may be determined to be partially certified based on a degree of certification determined as a function of smart contract status. The service bundle digital asset degree of certification may be determined as a function of the fraction of the asset's sub-tokens or sub-services that are supported by a contract or smart contract obligating a resource to perform or deliver the service. A service provider may broadcast the certification status of each contract encoded by a service bundle digital asset to a DL, permitting marketplace participants to access the asset's certification status as the status changes. Providing marketplace participants with access to an asset's certification status as the status changes may permit the marketplace to value the asset based on the certification status. In some cases, the purchaser of a service bundle digital asset may be provided with a digital service bundle asset certificate proving the purchaser owns the service bundle and all certified sub-services and resources. For example, the digital service bundle asset certificate may be a digital asset token encoding the unique ID of the primary asset, with the signature of each provider, sub-provider, and resource required to provide the service associated with the asset. In some cases, the asset owner may present a digital service bundle asset certificate as evidence of ownership, to facilitate trading or selling the asset based on the value of the allocated or obligated resources underlying the asset.

In an illustrative example, a consumer without a preference for a particular doctor (for example a consumer shopping for healthcare in a geographic region distant from the consumer's primary region), may be incentivized to purchase a service bundle digital asset without a contracted doctor at a lower market price, assuming a doctor will eventually sign a contract to perform the service. A doctor in search of work performing such a service may sign the contract to perform the service, resulting in the service bundle asset becoming fully certified. In an illustrative example, the market value of the fully certified asset may be greater, as a result of consensus verification of the underlying contracts. The asset class of a service bundle digital asset may be determined as a function of the asset degree of certification. In an illustrative example, the asset class of a service bundle digital asset may encode an ordinal class value enumerated in a range from a lowest class with no contracts in place, to a highest class with a contract in place for all asset sub-services. Intermediate asset classes may be defined in the range between the lowest and highest classes, where the intermediate asset classes represent the degree of certification varying from asset class to asset class. The market may determine a higher value for an asset having a higher asset class than a lower asset class, based on supply and demand in view of asset state, availability, and perceived quality. In an illustrative example, an asset class value may be represented or encoded in alphabetic, numeric, or symbolic elements. An asset class value may be represented or encoded as a sequence or combination of such alphabetic, numeric, or symbolic elements. For example, an asset may be defined to have an asset class value range A, B, C, D, and E. In this example, an asset having asset class A may be defined to be fully certified, class B may be defined to be 75% certified, class C may be defined to be 50% certified, class D may be defined to be 25% certified, and class E may be defined to be fully uncertified (0% certified). The asset class definition may be determined by the asset creator, based on an agreement with one or more asset exchange.

In another aspect, an apparatus may comprise: a processor (604); a data store (114) operably coupled with the processor (604); a user interface operably coupled with the processor (604); and a memory (606) operably coupled with the processor (604), wherein the memory (606) comprises encoded processor executable program instructions and data, wherein said instructions and data program and configure the processor (604) that when executed by the processor (604) the program instructions cause the apparatus to perform operations comprising: create in the data store (114) a healthcare service bundle database record representing a healthcare service bundle comprising a plurality of healthcare services to be performed separately by multiple providers, wherein at least one service of the plurality of healthcare services comprises: a procedure, a provider to perform the procedure, and a location where the procedure will be performed; present via the user interface the healthcare service bundle for selection as a function of procedure, provider, and location, based on the healthcare service bundle database record; and in response to receiving an indication via the user interface the healthcare service bundle has been purchased pre-paid: generate a unique confirmation number (408) for the purchased pre-paid healthcare service bundle; store the unique confirmation number (408) to the healthcare service bundle database record in the data store (114); generate in the user interface a voucher (400) with the unique confirmation number (408) for the pre-paid healthcare service bundle; set voucher (400) redemption status for each service of the plurality of healthcare services in the healthcare service bundle database record in the data store (114) to indicate the voucher (400) has not been redeemed; in response to receiving with the unique confirmation number (408) for the pre-paid healthcare service bundle an indication to redeem at least one service of the plurality of healthcare services: determine the voucher (400) redemption status for the at least one service to redeem, based on the healthcare service bundle database record in the data store (114); in response to determining the voucher (400) has not been redeemed for the least one service to redeem based on the voucher (400) redemption status: in response to verifying the at least one service to redeem has been performed: update the voucher (400) redemption status based on updating in the data store (114) the healthcare service bundle database record having the unique confirmation number (408) to indicate the at least one service has been redeemed.

The user interface may further comprise a smart phone.

The user interface may further comprise a personal computer.

The user interface may further comprise a web browser.

The healthcare service bundle may further comprise a primary service.

The healthcare service bundle may further comprise a secondary service associated with the primary service.

The operations performed by the apparatus in response to receiving the unique confirmation number (408) for the pre-paid healthcare service bundle with the indication to redeem at least one service of the plurality of healthcare services may further comprise: disburse funds.

The operations performed by the apparatus may further comprise receive payment for the healthcare service bundle.

The operations performed by the apparatus may further comprise disburse funds based on the payment received for the healthcare service bundle.

Disburse funds may further comprise disburse funds to more than one provider.

The at least one service of the plurality of healthcare services may further comprise providing a product.

The product may further comprise a drug.

The product may require a prescription.

The operations performed by the apparatus may further comprise render in the user interface a form to receive prescription information.

The operations performed by the apparatus may further comprise render in the user interface voucher history including healthcare service bundle voucher redemption status.

In an aspect, a method may comprise: creating by a processor (604) in a data store (114) a healthcare service bundle database record representing a healthcare service bundle comprising a plurality of healthcare services to be performed separately by multiple providers, wherein at least one service of the plurality of healthcare services comprises: a procedure, a provider to perform the procedure, and a location where the procedure will be performed; presenting by the processor (604) via a user interface the healthcare service bundle for selection as a function of procedure, provider, and location, based on the healthcare service bundle database record; and in response to receiving by the processor (604) an indication via the user interface the healthcare service bundle has been purchased pre-paid: generating by the processor (604) a unique confirmation number (408) for the purchased pre-paid healthcare service bundle; storing by the processor (604) the unique confirmation number (408) to the healthcare service bundle database record in the data store (114); generating by the processor (604) in the user interface a voucher (400) with the unique confirmation number (408) for the pre-paid healthcare service bundle; setting by the processor (604) voucher (400) redemption status for each service of the plurality of healthcare services in the healthcare service bundle database record in the data store (114) to indicate the voucher (400) has not been redeemed; and in response to the processor (604) receiving with the unique confirmation number (408) for the pre-paid healthcare service bundle an indication to redeem at least one service of the plurality of healthcare services: determining by the processor (604) the voucher (400) redemption status for the at least one service to redeem, based on the healthcare service bundle database record in the data store (114): in response to the processor (604) determining the voucher (400) has not been redeemed for the least one service to redeem based on the voucher (400) redemption status: in response to the processor (604) verifying the at least one service to redeem has been performed: updating by the processor (604) the voucher (400) redemption status based on updating in the data store (114) the healthcare service bundle database record having the unique confirmation number (408) to indicate the at least one service has been redeemed.

The user interface may further comprise a smart phone.

The user interface may further comprise a personal computer.

The user interface may further comprise a web browser.

The healthcare service bundle may further comprise a primary service.

The healthcare service bundle may further comprise a secondary service associated with the primary service.

The steps performed by the method in response to the processor (604) receiving with the unique confirmation number (408) for the pre-paid healthcare service bundle the indication to redeem at least one service of the plurality of healthcare services may further comprise: disbursing funds.

The steps performed by the method may further comprise receiving payment for the healthcare service bundle.

The steps performed by the method may further comprise disbursing funds based on the payment received for the healthcare service bundle.

Disbursing funds may further comprise disbursing funds to more than one provider.

The at least one service of the plurality of healthcare services may further comprise providing a product.

The product may further comprise a drug.

The product may require a prescription.

The steps performed by the method may further comprise rendering in the user interface a form to receive prescription information.

The steps performed by the method may further comprise rendering in the user interface voucher history including healthcare service bundle voucher redemption status.

In an aspect, an apparatus may comprise a system characterized in that the system comprises: a client system (140) comprising: a processor (604); a user interface coupled with the processor; a central server system (110) comprising: a processor (604); a data store (114) operably coupled with the processor (604); and a memory (606) operably coupled with the processor (604); wherein the processor of the central server system (110) is configured to: create in the data store (114) a transaction information database record of a bundled set of healthcare services representing a bundled set of healthcare services comprising a plurality of healthcare services to be performed separately by multiple providers, wherein at least one service of the plurality of healthcare services comprises: a procedure, a provider to perform the procedure, and a location where the procedure will be performed; wherein the processor of the client system is configured to: present, via the user interface, the bundled set of healthcare services for selection as a function of procedure, provider, and location, based on the transaction information database record of the bundled set of healthcare services; wherein the processor of the central server system (110), in response to receiving an indication, via the user interface of the client system (140), that the bundled set of healthcare services has been purchased pre-paid, is configured to: generate a unique confirmation number (408) for the purchased pre-paid bundled set of healthcare services; store the unique confirmation number (408) to the transaction information record of the bundled set of healthcare services in the data store (114); generate, in the user interface of the client system, a voucher (400) with the unique confirmation number (408) for the pre-paid bundled set of healthcare services; set a voucher (400) redemption status for each service of the plurality of healthcare services in the transaction information database record of the bundled set of healthcare services in the data store (114) to indicate the voucher (400) has not been redeemed; wherein the processor of the central server system (110), in response to receiving with the unique confirmation number (408) for the pre-paid bundled set of healthcare services an indication to redeem at least one service of the plurality of healthcare services is configured to: determine the voucher (400) redemption status for the at least one service to redeem, based on the transaction information database record of the bundled set of healthcare services in the data store (114); in response to determining the voucher (400) has not been redeemed for the least one service to redeem based on the voucher (400) redemption status: in response to verifying the at least one service to redeem has been performed: update the voucher (400) redemption status based on updating in the data store (114) the transaction information database record of the bundled set of healthcare services having the unique confirmation number (408) to indicate the at least one service has been redeemed.

The client system (140) may be a smart phone.

The client system (140) may be a personal computer.

The client system (140) may further comprise a web browser.

The bundled set of healthcare services may further comprise a primary service.

The bundled set of healthcare services may further comprise a secondary service associated with the primary service.

The operations performed by the system in response to receiving the unique confirmation number (408) for the pre-paid bundled set of healthcare services with the indication to redeem at least one service of the plurality of healthcare services may further comprise: disburse funds.

The operations performed by the system may further comprise receive a payment for the at least one service of the bundled set of healthcare services.

The operations performed by the system may further comprise disburse funds based on the payment received for the at least one service of the bundled set of healthcare services.

Disburse funds may further comprise disburse funds to more than one provider.

At least one service of the plurality of healthcare services may further comprise providing a product.

The product may further comprise a drug.

The product may require a prescription.

The operations performed by the system may further comprise render in the user interface of the client system (140) a form to receive prescription information.

The operations performed by the system may further comprise render, in the user interface of the client system, a voucher history including the bundled set of healthcare services voucher redemption status.

Apparatus and associated methods relate to determining medical services appropriate to a patient in response to a patient lifecycle event, presenting the medical services to the patient for selection, scheduling the selected medical services, and, automatically presenting the selected services for prepayment. The patient lifecycle event may be, for example, a doctor's order, diagnosis, condition change, payment, admission, or discharge. The services presented to the patient may be determined in response to, and as a function of, the lifecycle event. For example, the services presented may include procedures determined after the lifecycle event, in view of patient medical history. In an illustrative example, the services presented may be based on medical indication, contraindication, provider or facility availability, or patient scheduling preference, advantageously permitting more medically relevant, beneficial, convenient, or cost-effective services. Various examples may advantageously provide a discount for a service bundle provided at a particular time or facility.

In an aspect, a process is provided, comprising: in response to detecting a patient lifecycle event, offering medical services to the patient, comprising: determining medical services appropriate to the patient; presenting the medical services to the patient for selection; scheduling the selected medical services; and, automatically presenting the selected services for prepayment.

Detecting the patient lifecycle event may further comprise receiving an electronic message comprising an EHR (Electronic Health Record).

Determining medical services appropriate to the patient may further comprise determining optional medical services that are not contraindicated for the patient based on the lifecycle event and the patient medical history determined as a function of the EHR.

Detecting the patient lifecycle event may further comprise comparing a historical patient lifecycle state with the current patient lifecycle state.

Detecting the patient lifecycle event may further comprise determining if the patient lifecycle state changed, based on comparing the previous patient lifecycle state with the current patient lifecycle state.

Detecting the patient lifecycle event may further comprise determining the current patient lifecycle state based on medical evaluation of the patient condition.

The historical patient lifecycle state may be one of: new patient, well patient, acute care patient, chronic care patient, or recovering patient.

The current patient lifecycle state may be one of: new patient, well patient, acute care patient, chronic care patient, or recovering patient.

The patient lifecycle event may be one of: doctor's order issued, patient service scheduled, patient admitted, patient discharged, patient diagnosed, patient diagnosis changed, patient medical condition changed, patient age threshold reached, patient life expectancy changed, patient account balance due changed, or patient insurance changed.

Presenting the selected services for prepayment may further comprise presenting the selected services to a health insurance provider.

Presenting the selected services for prepayment may further comprise presenting the selected services to the patient.

The process may further comprise accepting payment.

Scheduling the selected medical services may further comprise sending the selected medical services to a hospital to be scheduled by the hospital.

The selected services may be sent to the hospital after the selected services are scheduled, in response to a scheduling event.

In an aspect, an apparatus is provided, comprising: a processor; a user interface, operably coupled with the processor; and, a memory, operably coupled with the processor, wherein the memory encodes processor executable program instructions and data to program and configure the processor to cause the apparatus to perform operations comprising: receive an electronic message comprising an EHR; determine the current patient lifecycle state based on the EHR; determine if a patient lifecycle event occurred, based on comparing a historical patient lifecycle state with the current patient lifecycle state; in response to determining a patient lifecycle event occurred: determine medical services to be offered to the patient, wherein the medical services are not contraindicated for the patient based on the lifecycle event and the patient medical history determined as a function of the EHR; present the medical services to be offered to the patient in the user interface for selection as a function of available service location and available service time; and, automatically present the selected services to the patient in the user interface for prepayment.

The operations performed by the apparatus may further comprise schedule the selected medical services based on associating an available service location and an available service time with a patient selected service location and a patient selected service time.

Schedule the selected medical services may further comprise send the selected medical services to a hospital to be scheduled by the hospital based on associating an available service location and an available service time with a patient selected service location and a patient selected service time.

The patient lifecycle event may further comprise patient service scheduled.

The patient lifecycle event may further comprise doctor's order issued.

The medical services appropriate to the patient may further comprise a medical service determined as a function of the patient lifecycle event.

The medical services to be offered to the patient may further comprise a medical service bundle based on medical facility utilization determined as a function of time.

The operations performed by the apparatus may further comprise sending the medical service bundle to the patient in a shopping cart format rendered in an email or text message.

The process may further comprise offering the patient a discount for prepayment.

In an aspect, an apparatus is provided, comprising: a processor; and, a memory, operably coupled with the processor, wherein the memory encodes processor executable program instructions and data to program and configure the processor to cause the apparatus to perform operations comprising: receive an electronic message comprising an EHR; determine the current patient lifecycle state based on the EHR: determine if a patient lifecycle event occurred, based on comparing a historical patient lifecycle state with the current patient lifecycle state; in response to determining a patient lifecycle event occurred, determine medical services to be offered to the patient, wherein the medical services are not contraindicated for the patient based on the lifecycle event and the patient medical history determined as a function of the EHR, wherein the medical services to be offered to the patient are determined as a function of the patient lifecycle event, and wherein the medical services to be offered to the patient further comprise a medical service bundle based on medical facility utilization determined as a function of time; present the medical services to be offered to the patient in a shopping cart format rendered in an email or text message to the patient for selection as a function of available service location and available service time; schedule the medical services selected by the patient based on associating an available service location and an available service time with a patient selected service location and a patient selected service time; and, automatically present the scheduled services to the patient with a discount offered for prepayment before a predetermined date.

The patient lifecycle event may be patient service scheduled, and the medical service bundle may further comprise a follow-up medical service medically indicated by the patient service scheduled.

The historical patient lifecycle state may be new patient, and the current patient lifecycle state may be well patient.

The historical patient lifecycle state may be new patient, and the current patient lifecycle state may be chronic care patient.

The historical patient lifecycle state may be acute care patient, and the current patient lifecycle state may be recovering patient.

The patient lifecycle event may be one of: doctor's order issued, patient service scheduled, patient admitted, patient discharged, patient diagnosed, patient diagnosis changed, patient medical condition changed, patient age threshold reached, patient life expectancy changed, patient account balance due changed, or patient insurance changed.

Schedule the medical services may further comprise send the selected medical services to a hospital to be scheduled by the hospital.

Various embodiments may achieve one or more advantages. For example, in some embodiments, medical practice profit may be improved. Such improved medical practice profit may be a result of reduced cost based on improved utilization of medical practice resources that may be otherwise spent sending bills, collecting payment, handling payment in-person, and the like. Various implementations may reduce the effort required by a medical practice to offer medically relevant or beneficial services to a patient. This facilitation may be a result of a patient lifecycle event triggering an offer for services related to the patient lifecycle event. For example, a patient lifecycle event or status change such as a doctor's order, patient registration for a primary service, diagnosis, or change in medical condition may automatically trigger other service offers medically indicated or beneficial with the primary service or change in lifecycle status. Some embodiments may improve the cost effectiveness of medical service offerings. Such improved medical service cost effectiveness may be a result of improved resource utilization based on offering additional medical services optionally available within the same service window as a primary service. For example, a primary service ordered by a doctor or scheduled by a patient may trigger an offer of optional services that are within the same or similar facility or time slot service window as the primary service. In an illustrative example, such an offer of optional services may enable a medical service provider to reduce cost and offer a discount to patients, as a result of improved resource utilization. Some examples may increase the quantity of medical services performed by a medical practice. This facilitation may be a result of increasing the chance of a patient scheduling an additional or optional procedure selected from offered procedures determined in response to a patient lifecycle event that has already occurred. For example, a medical practice may be able to offer more medically relevant or beneficial services, or offer more cost-effective service schedules, from the temporal perspective after a patient lifecycle event has occurred, in view of the patient's medical history. In addition, after a patient lifecycle event, there may be enhanced patient motivation to schedule additional procedures or respond to a discount offer, improving the chances for the medical practice to provide additional services to the patient.

Some embodiments may improve a patient's ease of access to medical services. This facilitation may be a result of reducing the patient's effort selecting, scheduling, and paying for medical services. Some examples may improve a patient's medical care experience. Such improved patient medical care experience may be a result of a medical practice offering a patient a bundle of multiple services that could be performed in fewer visits, thereby reducing the number of times a patient has to revisit a medical service facility. Some embodiments may improve a patient's benefit from medical services. This facilitation may be a result of a medical service provider offering the patient more medically beneficial services tailored to the patient's condition or status in the patient lifecycle. In some embodiments, a patient's cost for medical services may be reduced. Such reduced medical service cost to a patient may be a result of a medical practice passing on to the patient medical practice cost savings based on improved medical practice resource utilization from optional services available within the same service window as a primary service. In some designs, a patient's cost for medical services may be reduced as a result of a medical practice providing a prepayment discount to the patient.

Various implementations may construct a proposed medical service bundle for a patient in response to detecting a patient lifecycle event has occurred. A patient lifecycle event may be, for example, patient registration for a service, or, any patient lifecycle event, including, but not limited to, a doctor's order, scheduling, administrative updates to patient records, patient admission, patient discharge, overdue payment, change in payment account balance due, and the like. The medical service bundle proposed to the patient may include, for example, the services that were actually provided or scheduled, or any additional or related services the patient might be interested in.

An exemplary implementation may, for example, receive electronic notification from an EHR or other source, determine the appropriate procedure(s) to offer to the patient, based on the data or codes in that electronic notification, create a shopping cart including a proposed medical service bundle for the patient, and optionally email or text the shopping cart to the patient. The shopping cart may also be saved in a portal (for example, an exemplary MDsave Direct portal implementation). In an illustrative example, a provider using the portal where the shopping cart was saved may directly look up the shopping cart or service bundle to aid completing the purchase, either in person, online (for example by live chat), or on the phone with the patient.

Some example designs may include offered optional services that are chosen based on future procedures indicated for the patient, medical contraindication, provider or facility availability, or patient scheduling preference. Some embodiments may offer a discount for scheduling a particular bundle ("cart") of services at a particular date, time, or facility, or with a particular provider or doctor. In an illustrative example, some implementations may permit a patient to select from the offered services and prepay for the selected services. In an example illustrative of various implementations' usage, in addition to minimizing the number of times a patient has to revisit the facility, a medical practice may reduce resources spent on sending bills, collecting payment, dealing with payment in-person, and the like.

In an example illustrative of technical effect that may result from various implementations' usage, the trigger condition to construct a service offer using the time value of the temporal perspective after a patient lifecycle event may improve medical care and reduce cost. For example, a medical service bundle determined after a patient lifecycle event may be more closely customized to the patient's medical condition and medical history in view of the lifecycle event. Such a perspective view triggered in response to a patient lifecycle event may permit offering more medically relevant additional procedures, may increase the chance a patient may select an additional procedure, and may improve medical practice resource utilization, in contrast with offering the patient optional services before a patient lifecycle event (such as before the patient is registered for a procedure, or commits to a procedure schedule). In an illustrative example, a patient that has already scheduled a primary procedure on a given day may have already arranged their personal or professional schedule to accommodate the primary procedure. Such a patient may be more likely to schedule an additional procedure at the same facility on the same day in response to a discount offer if the additional procedure is not medically contraindicated by the primary procedure.

In some examples, a service may be scheduled by a hospital. For example, an embodiment process or apparatus may determine a service bundle, present the service bundle to a patient for selection of services the patient may be interested in, and then leave scheduling to a hospital. The services selected by the patient may be sent to a hospital for scheduling by the hospital. Some designs may send out a shopping cart of services after scheduling takes place, in response to the scheduling event: that is, using the scheduling event as a trigger to send out the shopping cart of services.

Various implementations may create a shopping cart in response to a trigger condition to offer services. The trigger condition to offer services may be a patient lifecycle event (for example, patient registration for a procedure, change in patient condition, diagnosis, doctor's order, admission, discharge, and the like). For example, patient registration for a primary service may trigger other service offers that are within the same service window (for example, time slot and/or facility) of the primary service, permitting a medical practice to enhance utilization of facility services and resources, reducing the number of times a patient may have to revisit the facility, and providing a cost saving to the patient through prepayment.

Exemplary embodiments of the present invention relate to the marketing and facilitating the sale of services and products. More specifically, exemplary embodiments relate to methods and apparatuses for providing a web-based mechanism allowing prospective patients to search for and compare healthcare services and products offered by local providers, including bundled sets of services, and facilitating prepaid purchases of such healthcare services and products by prospective patients at discounted rates.

Exemplary embodiments of the present invention are related to an apparatus for facilitating purchases of services offered by service providers. The apparatus includes an application server providing a network service that is accessible to a plurality of users through a plurality of client systems communicatively coupled to the application server via a network and a data storage system storing a service offer database that is maintained by the application server.

The service offer database comprises a plurality of service offer information records respectively associated with a plurality of service offers. The plurality of service offers includes at least one service offer for a bundled set of services. Each service offer information record comprises an indication of a primary service of the associated service offer, a purchase price for the associated service offer, a payment amount for the primary service, and compensation information for the primary service. Upon receiving purchase information for the user for purchasing the selected service offer from the client system, the network service is operable to issue a request to the funding source for funds corresponding to the purchase price included in the service offer information record associated with the selected service offer to process a purchase of the selected service offer by the user.

In exemplary embodiments, each service offer for a bundled set of services comprises a bundled set of healthcare services provided by corresponding healthcare service providers.

In exemplary embodiments, at least one service offer information record associated with a service offer for a bundled set of services further comprises an indication of a facility for performing the primary service, a facility fee for the facility, and compensation information for the facility fee.

In exemplary embodiments, at least one service offer information record associated with a service offer for a bundled set of services further comprises an indication that at least one of the secondary services associated with the primary service is an optional secondary service.

In exemplary embodiments, the data storage system stores a profile database that is maintained by the application server. The profile database comprises a respective account information record for each of a plurality of user accounts registered with the application server. The plurality of user accounts includes a plurality of customer accounts and a plurality of provider accounts. The account information record for each user account comprising information for authorizing a user accessing the network service from one of the client systems to access the network service in association with the user account.

In exemplary embodiments, the plurality of provider accounts includes a plurality of physician accounts and a plurality of practice group accounts, the account information record for each practice group account comprises an indication of one or more of the physician accounts being affiliated with the practice group account.

In exemplary embodiments, the data storage system stores a transaction information database that is maintained by the application server. The transaction information database comprises a respective purchase information record for each processed purchase, by a user accessing the network service from one of the client systems in association with a customer account, of a service offer that has been created by a user accessing the network service from one of the client systems in association with a provider account, the respective purchase information record for each processed purchase comprising an indication of the service offer information record associated with the purchased service offer and, for each of the primary service and any secondary service of the service offer, and an indication of whether the purchase has been redeemed with respect to the service.

In exemplary embodiments, the network service, upon being accessed by a user of one of the client systems to process a purchase of a service offer, generates a voucher for the user that specifies a unique confirmation number for the purchase and the corresponding service provider for each of the primary service and any secondary service of the purchased service offer, and, for each of the primary service and any secondary service of the purchased service offer, sets the purchase information record for the processed purchase to indicate that the purchase has not been redeemed with respect to the service.

Exemplary embodiments of the present invention that are related to computer-implemented processes and computer systems corresponding to the above-summarized exemplary embodiments directed to an apparatus are also described and claimed herein.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIG. 4B is an illustration of an example voucher that may be generated within a user interface by functions provided within a customer portal for a purchased service that is offered as a bundled set of services in accordance with exemplary embodiments of the present invention.

FIGS. 7A-7C are a number of screen shots illustrating examples of a graphical user interfaces that may be implemented by services provided within a provider portal in accordance with exemplary embodiments of the present invention.

Figure 1A:
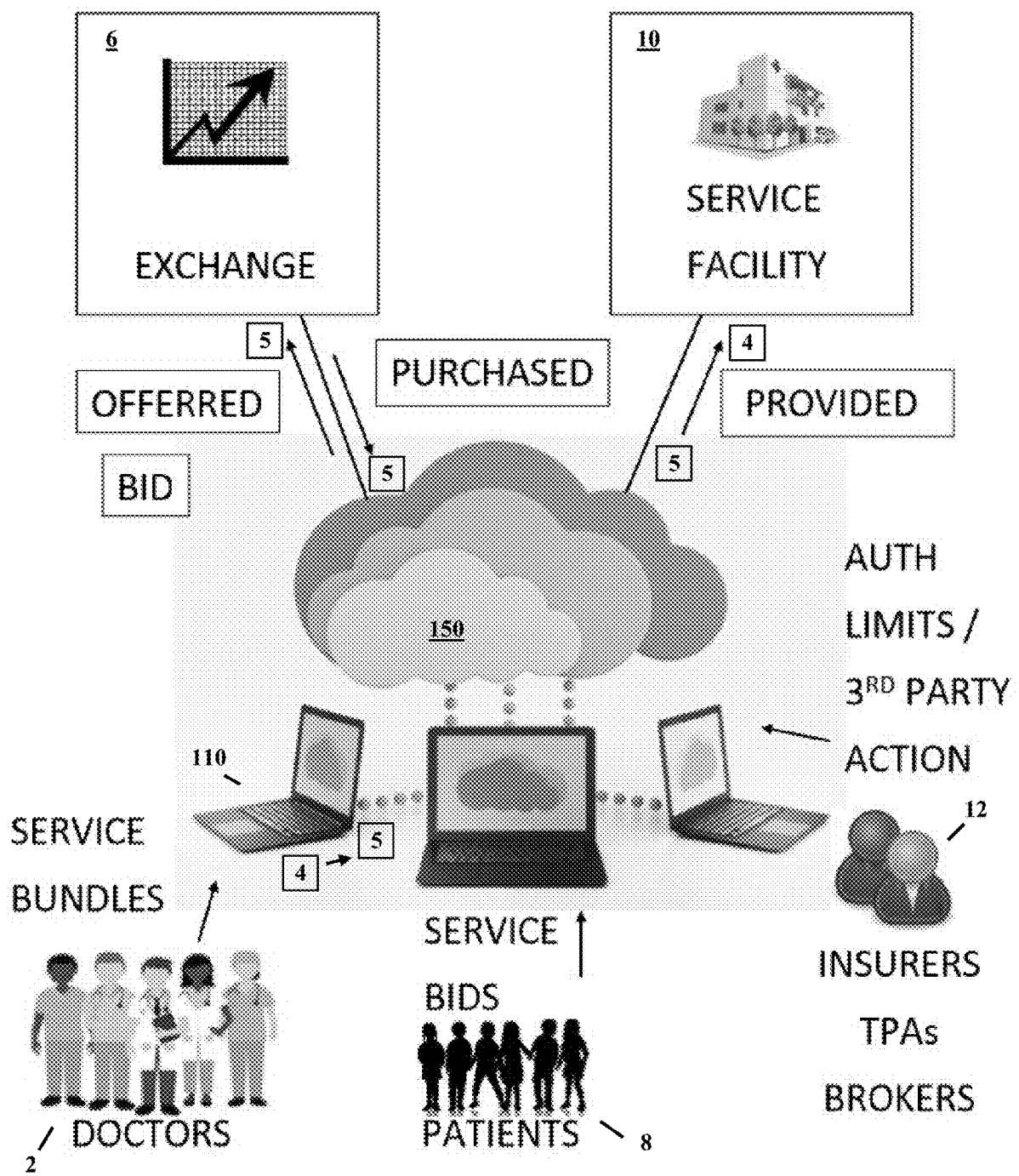
FIGS. 1AA-1AN depict various views illustrative of an example healthcare marketplace system that can be configured to implement exemplary embodiments of the present invention.
Figure 1A:
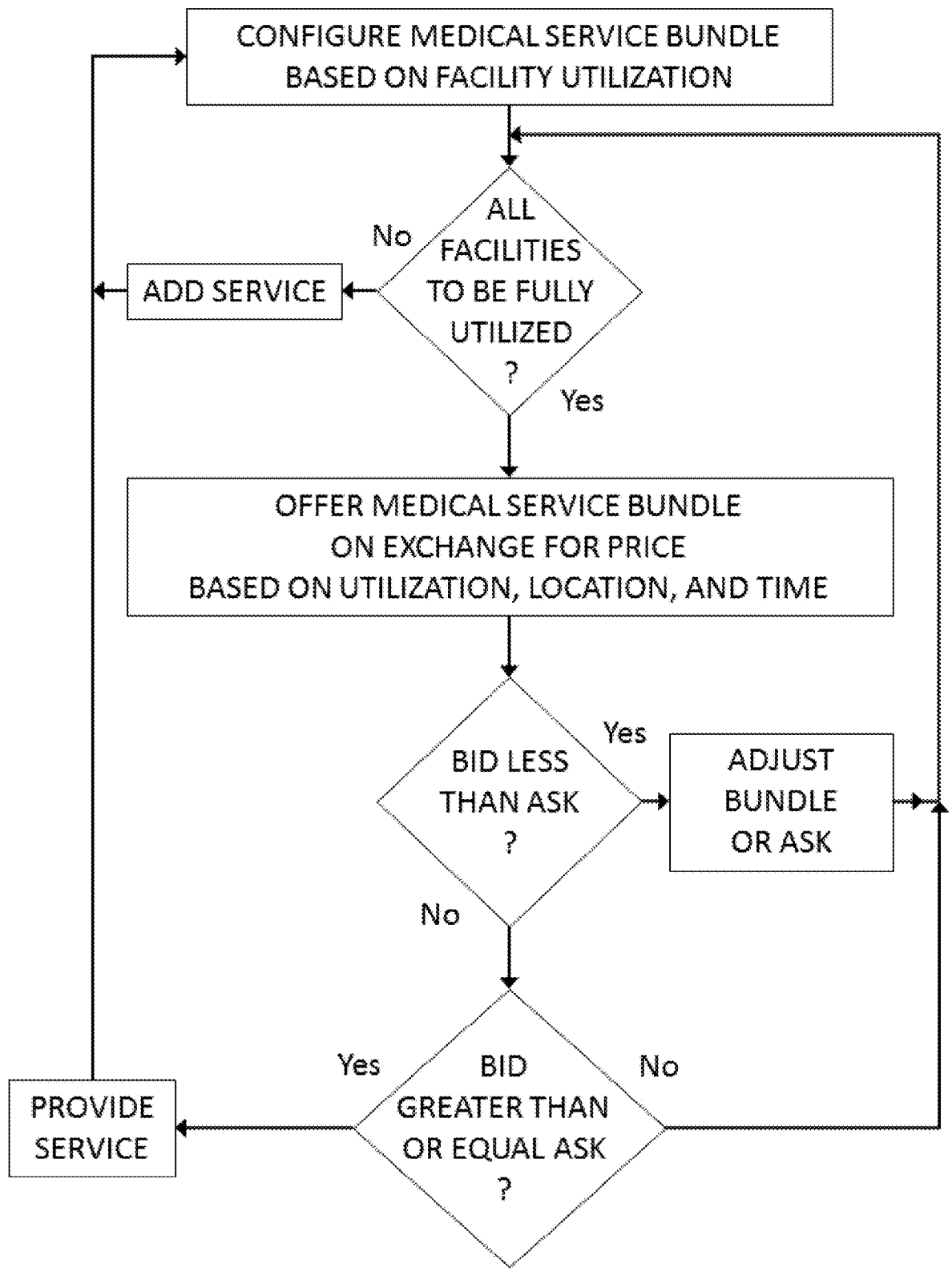
Figure 1A:
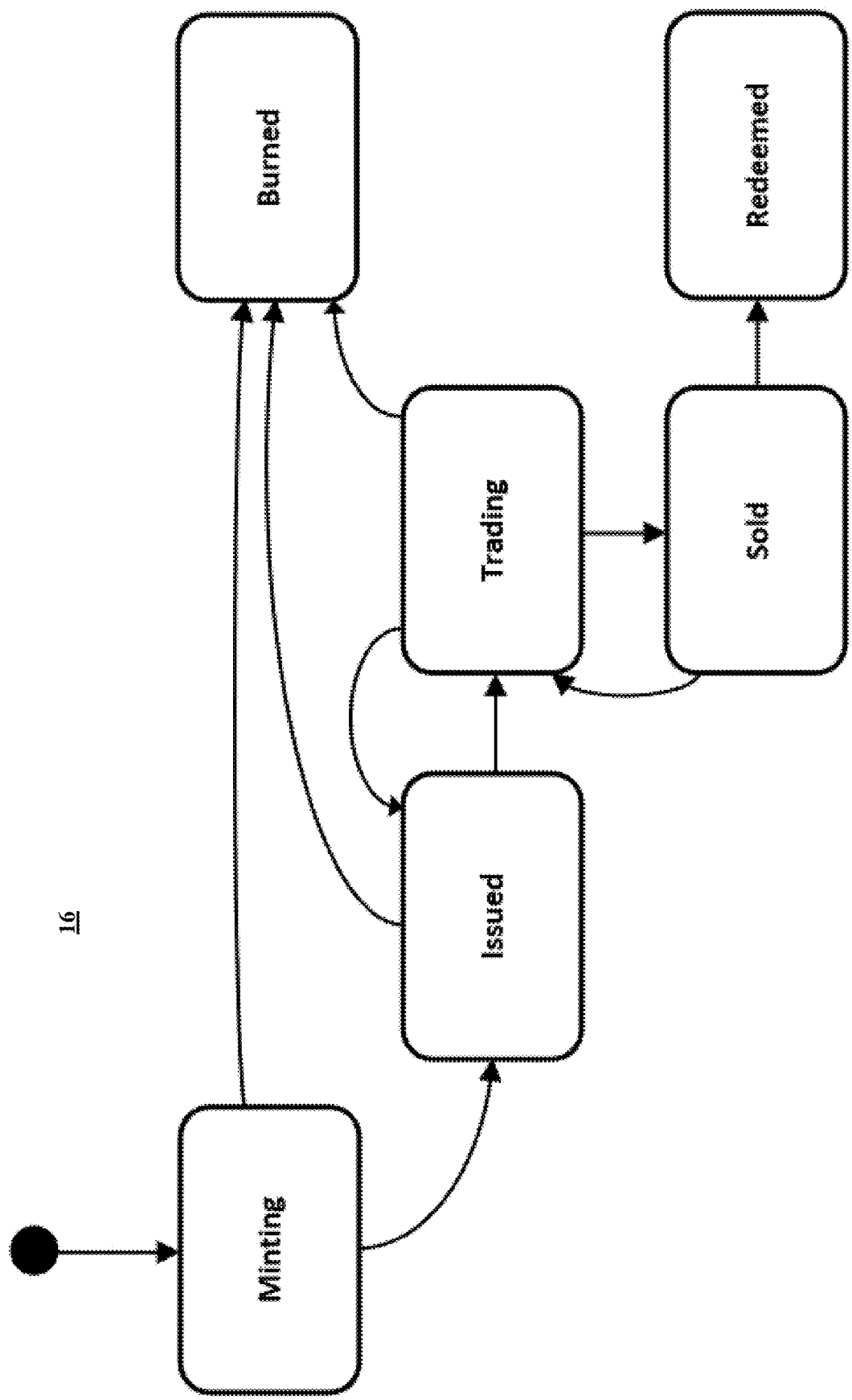
Figure 1A:
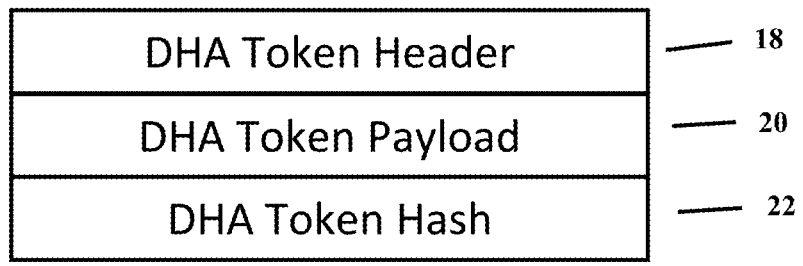
Figure 1A:
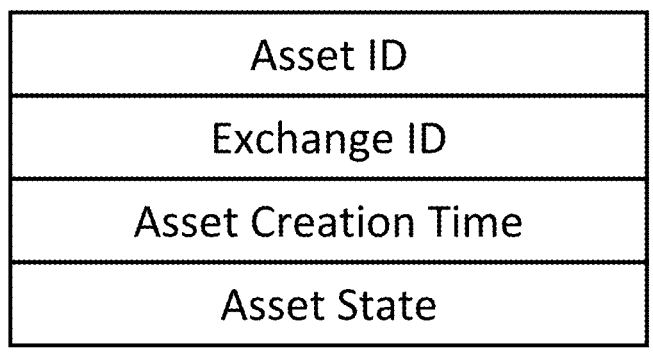
Figure 1A:
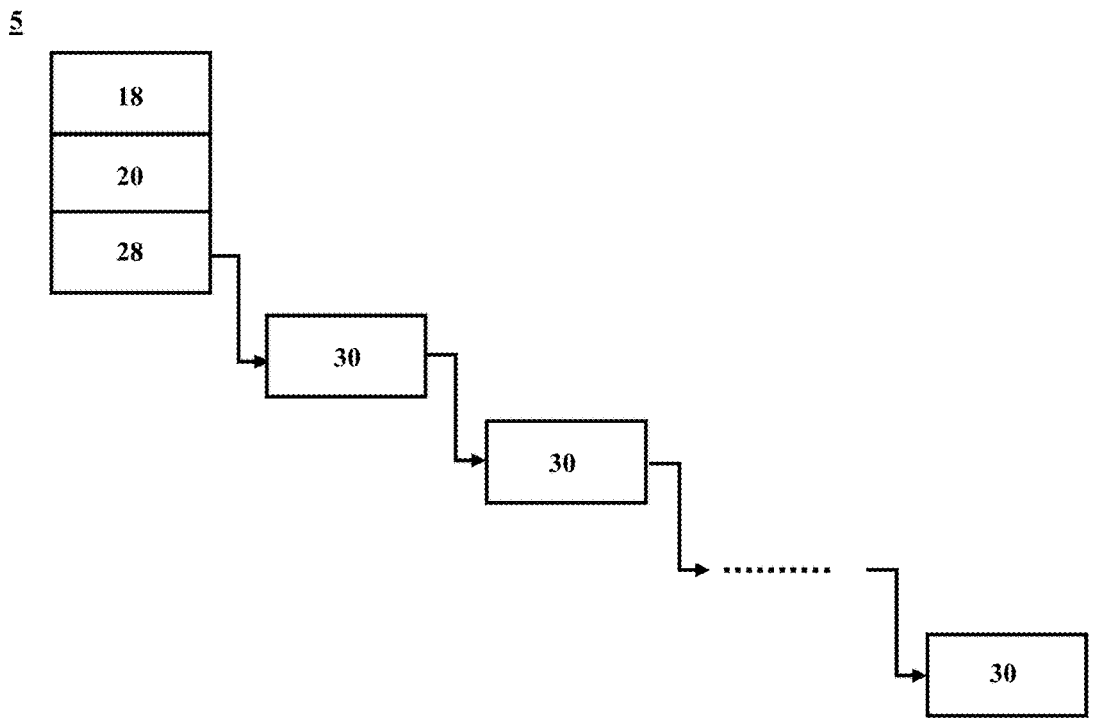
Figure 1A:
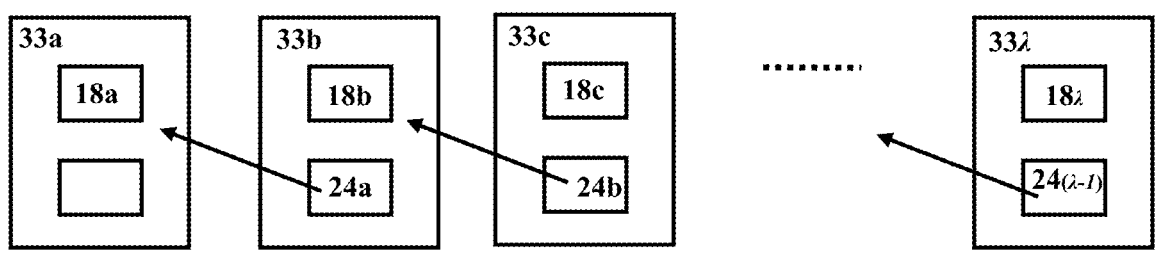
Figure 1A:
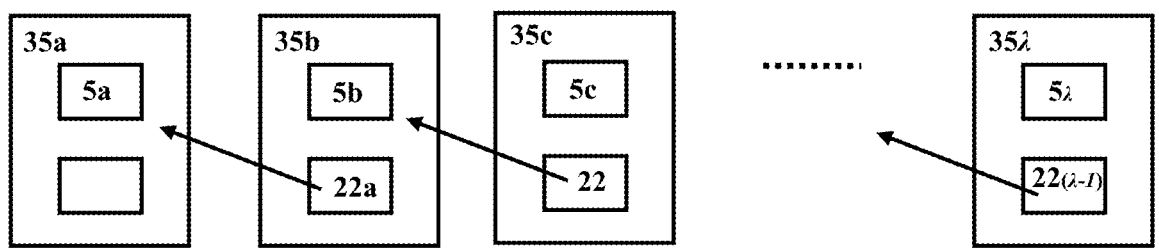
Figure 1A:
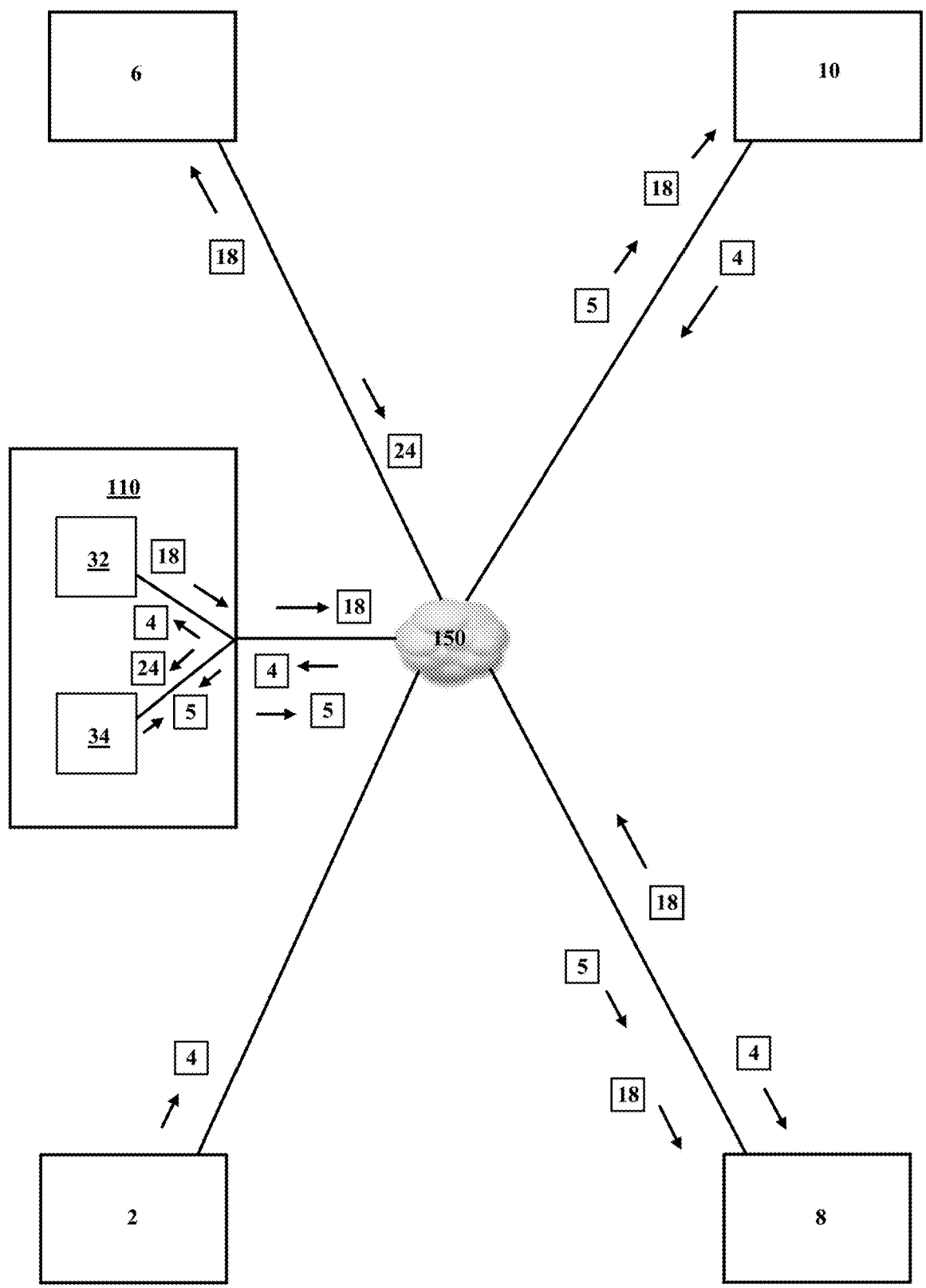
Figure 1A:
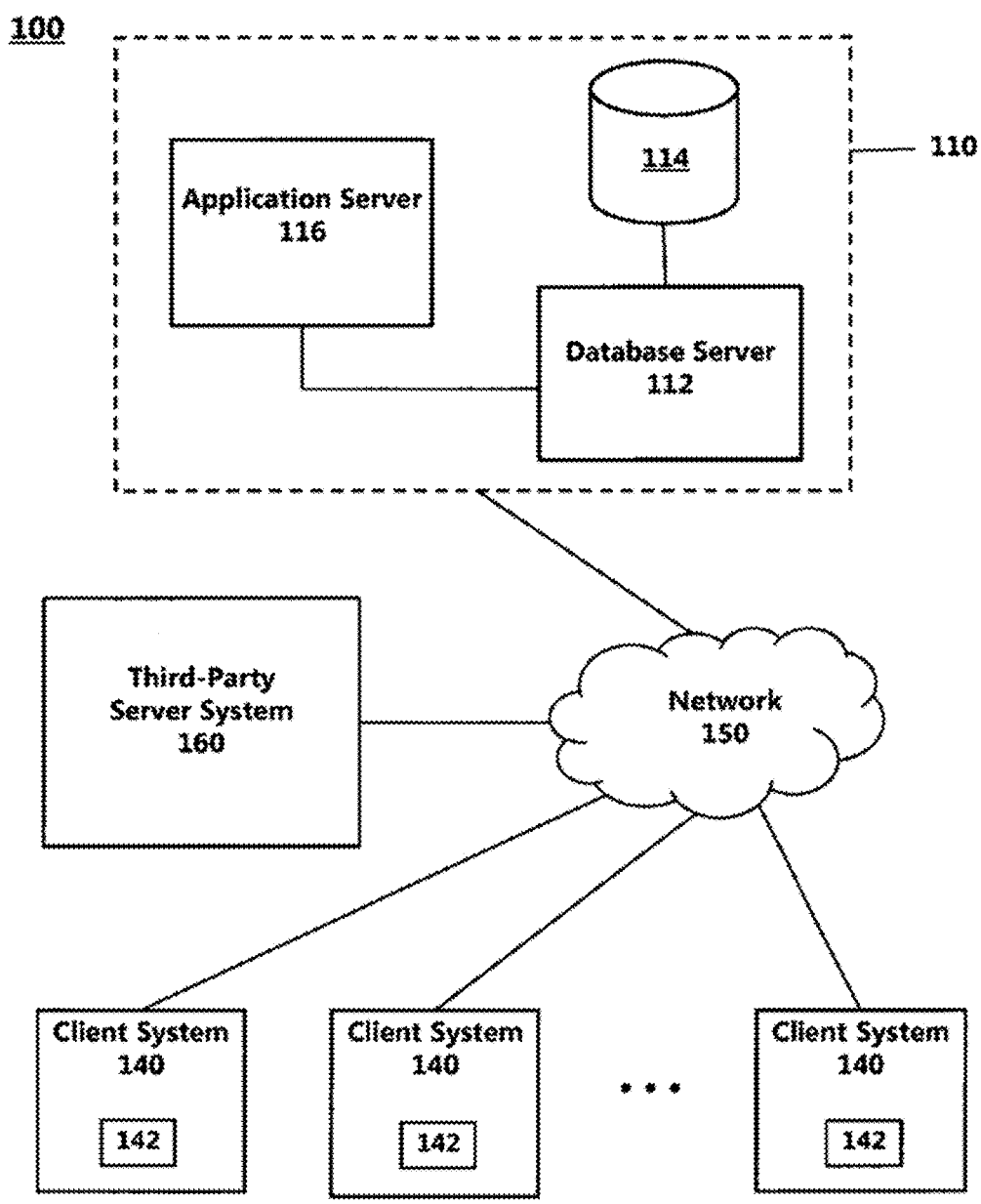

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered to be within the scope of the claimed invention.

Like reference symbols in the various drawings indicate like elements.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Exemplary embodiments of a transactional marketplace system in accordance with the present invention will now be described with reference to the drawings. Exemplary embodiments of the present invention may be implemented to provide healthcare service providers and pharmacies with a mechanism to remotely offer healthcare services and products to prospective patients at discounted rates in exchange for prepayment of the costs for the services and products via a network-based application (for example, a web-based application).

In this regard, exemplary embodiments may further be implemented to provide prospective patients with a mechanism to remotely search, compare, and make pre-paid purchases of such healthcare services and products offered by local medical service providers and pharmacies via a network-connected device configured to access the network-based application. Exemplary embodiments may be further implemented to provide healthcare service providers with the ability to remotely offer a bundled set of healthcare services that are performed separately by multiple providers to prospective patients through such a network-based mechanism in which the patient is provided the opportunity to make a prepaid purchase of such a bundled set of services in a single transaction via the network-connected device, whereby the network-based application facilitates a disbursed distribution of the payment among the multiple healthcare service providers that perform services included in the bundled set of services.

Exemplary embodiments may also be further implemented to provide a virtual payment system for facilitating and accounting for the exchange of payment for services and products purchased by (or otherwise on behalf of) patients and offered by healthcare providers via the transactional marketplace system in which a respective virtual money account is established and utilized for each participant in transactions conducted within the marketplace system to manage and track the process of exchanging actual currency and/or credits used to pay for the transactions through the use of corresponding virtual funds created within the virtual payment system.

In such exemplary embodiments, the virtual funds may be allocated and distributed to, exchanged among, and redeemed for corresponding amounts of actual currency by various participants to each transaction for which payment is facilitated through the virtual payment system, and the participants to transactions within the virtual payment system for which respective virtual money accounts are established and utilized may include, in addition to patients, healthcare providers, or other entities specified for receiving payments for services or products offered through the marketplace system, third party payers, and an entity that provides the transactional marketplace system.

Exemplary embodiments may be further implemented to provide various types of healthcare service providers, which may include individual physicians, practice groups, and hospital systems, with the ability to establish affiliations with one another through such a network-based mechanism and provide various options allowing the service providers to remotely offer healthcare services in association with these affiliations.

It should further be noted that various aspects of exemplary embodiments of the present invention described herein are not limited to healthcare services (also referred to herein as procedures) and products but, rather, may be implemented with respect to any suitable classes and types of services and products that may be offered by any suitable classes and types of service providers and retailers.

In FIG. 1AA, the doctor 2 creates the medical service asset bundle 4 using the exemplary healthcare marketplace 110. The healthcare marketplace 110 constructs the DHA 5 representing asset bundle 4. The healthcare marketplace 110 issues the DHA 5 to the exchange 6 via the network cloud 150. In the depicted example, the exchange 6 is an asset exchange configured to facilitate DHA exchange. The exchange 6 may be a commodity exchange. The DHA 5 may be purchased on the exchange 6 for a price determined as a function of supply and demand and bid activity on the exchange 6. The medical service asset bundle 4 may be automatically adjusted in response to bid activity on the exchange 6. In the depicted example, the patient 8 purchases the DHA 5 through the exchange 6. The service facility 10 provides the services included in the medical service asset bundle 4 when the patient 8 redeems the DHA 5 for the services. The insurers, TPAs (Third Party Administrators), or brokers 12 may participate in exchange 6 transactions, to provide payment authorization limits, or engage in various third-party actions such as, for example, bulk transactions, or brokered trades. In an illustrative example, offering bundled medical services through an exchange increases service facility utilization, and improves service availability and efficiency. The offered services may be bundled to take advantage of underutilized capacity, automatically matching supply to demand through an exchange facilitating adapting bundled service offers in response to bids received for service bundles. For example, an offered service bundle may be configured with services offered at a price, location and time selected in response to demand represented by bid activity and insurance authorization limits for the services.

FIG. 1 AB is a flowchart illustrating the process flow 14 of an exemplary healthcare marketplace system. In the depicted example, a provider may offer a service bundle selected based on optimizing facility or resource utilization. If optimum utilization cannot be achieved (for example, all facilities utilized), a service may be added to the bundle. The bundle may be converted to a DHA. The system offers the DHA through an exchange for an ask price determined based on utilization, location, and time. In response to exchange bid activity, the system adapts the services offered or the ask price, to automatically adapt supply to demand. Various implementations may include operations such as configuring a service bundle based on facility utilization, offering the service bundle for purchase through an exchange and, in response to exchange bid activity, providing the bundled services at a time and location based on the bid activity. Some example medical services may be offered by a provider for purchase by a consumer. The service bundle may be adjusted with additional optional services selected as a function of the bid activity. The offered time, location, and price for bundled services may be automatically adjusted, based on supply and demand reflecting bid activity. For example, the price for bundled services may be automatically increased, or decreased, based on supply and demand, determined as a function of bid activity. Some examples may include exchange contracts with a viability date before which the services may not be delivered, to facilitate pre-payment discounts due to market-timing through the exchange. Various designs may include resource locking to limit the possibility an essential resource, such as a medical specialist or facility, is not overallocated by the enactment of multiple contracts at a given time in the future. Some designs may facilitate trades of purchased service bundles between pairs of consumers, or pairs of providers.

FIG. 1AC is a state diagram illustrating an exemplary DHA lifecycle. The depicted DHA lifecycle 16 begins when the DHA is created in the minting state. New DHA may be held in the minting state, or the DHA may be modified to transition to the issued state. After issue, the DHA may be made available for purchase in the trading state, or the DHA may be destroyed to transition to the burned state. The DHA may be withdrawn from trading to the issued state, or the DHA may be destroyed to transition to the burned state. The DHA may make multiple transitions between trading and sold states as the DHA is purchased and resold. The DHA may be redeemed upon purchase in the sold state. The depicted DHA lifecycle is a non-limiting example, and other DHA lifecycle states, or sub-states, are possible.

FIG. 1AD is a table including exemplary DHA lifecycle state descriptions. In the minting state, a new DHA is created. A created DHA is available for trading in the issued state. In the trading state, an issued DHA is available for purchase via an exchange. In the sold state, DHA ownership changed. The DHA is in the redeemed state when the DHA product or service asset has been delivered or provided. Destroyed DHA that represented a liquidated asset are in the burned state. The depicted DHA lifecycle state descriptions are a non-limiting example, and other details characterizing DHA lifecycle states are possible.

FIG. 1AE is a table including exemplary DHA lifecycle state parameters. Specifically, example actions and next states pertaining to various DHA lifecycle states are described. A DHA creator may create a new DHA. The DHA enters the minting state when created. The DHA creator may destroy a DHA in the minting state. The DHA enters the burned state when destroyed. The DHA provider or owner may assign a DHA in the minting state to be issued. The owner may take ownership after DHA creation. The issued DHA may be bound to an underlying asset, though not yet traded. The DHA provider or owner may offer a DHA in the issued state for trading on an exchange. The DHA creator may destroy a DHA in the issued or trading states. The DHA enters the burned state when destroyed. The DHA creator may move a DHA in the trading state to the issued state, to modify the DHA. The DHA owner may sell a DHA in the trading state to accept a purchase bid. The DHA enters the sold state when sold. The DHA owner may re-sell a DHA in the sold state to move the DHA to the trading state. The DHA owner or provider may redeem the DHA in the sold state to obtain the asset underlying the DHA. The depicted DHA lifecycle state parameters are a non-limiting example, and other DHA lifecycle state parameters are possible.

In FIG. 1AF, the depicted DHA token 5 includes the DHA token header 18, the DHA token payload 20, and the DHA token hash 22. The DHA token hash 22 is the hash of the combined DHA token header 18 and the DHA token payload 20.

In FIG. 1AG, the depicted DHA token header 18 includes an Asset ID, Exchange ID, Asset Creation Time, and Asset State. The Asset ID and Exchange ID may be globally unique within a predetermined namespace. For example, the Asset ID or Exchange ID may be a UUID in accordance with RFC 4122, or the like. The Asset Creation Time may be given in seconds since the epoch, in accordance with POSIX, or UNIX time rationales. In the depicted DHA token header 18, once created, the Asset ID, Exchange ID, and Asset Creation Time are immutable. In the depicted DHA token header 18, the Asset State is mutable, having possible values of minting, issued, trading, sold, redeemed, and burned.

In FIG. 1AH, the depicted DHA token payload 20 includes the Asset ID and Asset Creation Time encoded by the DHA token header 18, depicted by FIG. 1AG. The depicted Asset Status Sequence ID is a nonce. The depicted DHA token payload 20 includes the DHA Header Hash 24 of the DHA token header 18, depicted by FIG. 1AG. The depicted DHA token payload 20 includes the Owner-signed Header Hash encoding the DHA owner signature of the DHA Header hash 24. The depicted DHA token payload 20 includes participant identification and public keys to facilitate transaction verification. The depicted DHA token payload 20 includes the Bundle ID 26 reference to an asset bundle determined according to techniques disclosed herein.

In FIG. 1AI, the depicted DHA token asset bundle 28 is the asset bundle referenced by the Bundle ID 26 encoded by the DHA token payload 20, depicted by FIG. 1AH. The depicted DHA token asset bundle 28 includes the Product or Service ID identifying a product or service determined according to techniques disclosed herein. The depicted Provider ID, Location ID, and Facility ID parameters may specify asset delivery by particular resources at a predetermined location and time. The DHA may not be available for redemption before the Earliest Availability Time. The DHA may be liquidated when the Expiration Time arrives. The depicted DHA token asset bundle 28 services may be delivered at the Contract Service Time according to terms agreed to under the Contract. The Contract may bind resources, such as medical professionals, equipment providers, facility operators, or support staff, to provide the service underlying the DHA. The Contract may be a smart contract. The depicted DHA token asset bundle 28 may be linked through the Sub-Bundle ID 30 to one or more asset bundle similarly structured to the depicted DHA token asset bundle 28.

In FIG. 1AJ, the depicted DHA token 5 includes the DHA token header 18, the DHA token payload 20, and a series of asset sub-bundles linked by their Sub-Bundle ID 30 to the DHA token asset bundle 28.

In FIG. 1AK, the depicted DHA token header stream 32 includes the series of DHA token header 18a, 18b, 18c, . . . , 18λ transactions 33a, 33b, 33c, . . . , 33λ. In the depicted example, each DHA token header 18b, 18c, . . . , 18λ transaction encodes the DHA token header hash 24a, 24b, . . . , 24(λ-1) of the previous transaction, to facilitate DHA token header verification.

In FIG. 1AL, the depicted DHA token stream 34 includes the series of DHA token 5a, 5b, 5c, . . . , 5λ transactions 35a, 35b, 35c, . . . , 35λ. In the depicted example, each DHA token 5b, 5c, . . . , 5λ transaction encodes the DHA token hash 22a, 22b, . . . , 22(λ-1) of the previous transaction, to facilitate DHA token verification.

In FIG. 1AM, the exemplary healthcare marketplace system 110 receives the medical service asset bundle 4 from the doctor 2. The healthcare marketplace system 110 converts the asset bundle to the DHA token 5 representing the asset bundle 4. The DHA 5 includes the DHA token header 18 and the DHA payload associated by the DHA token header hash 24. The healthcare marketplace system 110 maintains the depicted DHA token header stream 32 and DHA token stream 34. The healthcare marketplace system 110 provides the DHA token header 18 to the exchange 6. The DHA 5 may be purchased on the exchange 6 for a price determined as a function of supply and demand and bid activity on the exchange 6. The exchange 6 associates bid activity to the DHA 5 via the token header hash 24. The patient 8 may observe the bid activity on the exchange 6 related to the DHA token header 18. The patient 8 may use the token header 18 to retrieve the complete DHA 5 from the healthcare marketplace system 110, for example to evaluate the underlying asset bundle 4. The patient 8 may purchase the DHA 5 by submitting a bid for the asset bundle 4. The asset bundle 4 is represented on the exchange 6 by the token header 18. When the patient 8 completes the DHA 5 purchase, the complete DHA 5 may be delivered to the patient 8. The service facility 10 provides the services included in the medical service asset bundle 4 when the patient 8 redeems the DHA 5 for the services.

Referring now to FIG. 1AN, a schematic diagram illustrating an example network architecture for a healthcare marketplace system 100 that can be configured to implement exemplary embodiments of the present invention is provided. It should of course be understood that FIG. 1AN is intended as an example, not as an architectural limitation for different embodiments of the present invention, and therefore, the particular elements depicted in FIG. 1AN should not be considered limiting with regard to the environments within which exemplary embodiments of the present invention may be implemented.

In the example illustrated in FIG. 1AN, healthcare marketplace system 100 is implemented as a client/server system that includes a central server system 110 that is commonly accessed by each user of the system through operation of any of a plurality of client systems 140 that are operatively coupled to the central server system via a communication network 150. Central server system 110 further includes a database server 112 that is coupled to a data store 114 and an application server 116, and each client system 140 is a user terminal or other client device implementing software for and running a respective client application 142 for accessing services provided via a network-based application (also referred to herein as a network service) implemented by application server 116.

As further illustrated, exemplary marketplace system 100 may also include at least one third-party server system 160 to enable other functionality that may be accessed and utilized by server system 110 to provide and/or enhance the network service discussed herein. In exemplary embodiments, marketplace system 100 can include additional servers, clients, and other devices not shown in FIG. 1AN. The particular architecture depicted in FIG. 1AN is provided as an example for illustrative purposes and, in exemplary embodiments, any number of client systems 140 may be connected to server system 110 at any given time via network 150, and server system 110 can comprise multiple server components and databases located within a single server system or within multiple server systems, where the multiple server systems are integrated with or accessible by users of client systems 140 as a distributed server system via network 150.

In exemplary embodiments, network 150 can be configured to facilitate communications between server system 110 and client systems 140, as well as communications with and between other devices and computers connected together within marketplace system 100, by any suitable wired (including optical fiber), wireless technology, or any suitable combination thereof, including, but not limited to, personal area networks (PANs), local area networks (LANs), wireless networks, wide-area networks (WAN), the Internet (a network of heterogeneous networks using the Internet Protocol, IP), and virtual private networks, and the network may also utilize any suitable hardware, software, and firmware technology to connect devices such as, for example, optical fiber, Ethernet, ISDN (Integrated Services Digital Network), T-1 or T-3 link, FDDI (Fiber Distributed Data Network), cable or wireless LMDS network, Wireless LAN, Wireless PAN (for example, IrDA, Bluetooth, Wireless USB, Z-Wave and ZigBee), HomePNA, Power line communication, or telephone line network. Such a network connection can include intranets, extranets, and the Internet, may contain any number of network infrastructure elements including routers, switches, gateways, etc., can comprise a circuit switched network, such as the Public Service Telephone Network (PSTN), a packet switched network, such as the global Internet, a private WAN or LAN, a telecommunications network, a broadcast network, or a point-to-point network, and may utilize a variety of networking protocols now available or later developed including, but not limited to the Transmission Control Protocol/Internet Protocol (TCP/IP) suite of protocols for communication.

In exemplary embodiments, application server 116, database server 112, and any other servers employed within server system 110 and third-party servers utilized within marketplace system 100 can be implemented within any suitable computing system or systems such as a workstation computer, a mainframe computer, a server system (for example, SUN ULTRA workstations running the SUN operating system, IBM RS/6000 workstations and servers running the AIX operating system, or an IBM zSeries eServer running z/OS, zNM, or LINUX OS), a server cluster, a distributed computing system, a cloud based computing system, or the like, as well as any of the various types of computing systems and devices described below with reference to the client systems 140. Server system 110 may be implemented using any of a variety of architectures. For example, application server 116 and database server 112 may also be implemented independently or as a single, integrated device. While the exemplary embodiment illustrated in FIG. 1AN depicts application server 116 and database server 112 as individual components, the applications provided by these servers, or various combinations of these applications, may actually be server applications running on separate physical devices. In this regard, server system 110 may comprise a number of computers connected together via a network and, therefore, may exist as multiple separate logical and/or physical units, and/or as multiple servers acting in concert or independently, wherein each server may be comprised of multiple separate logical and/or physical units. In exemplary embodiments, server system 110 can be connected to network 150 through a collection of suitable security appliances, which may be implemented in hardware, software, or a combination of hardware and software.

As illustrated in FIG. 1AN, application server 116 is communicatively coupled to database server 112. Database server 112 is connected to data store 114, which comprises a plurality of databases that are maintained by database server 112, accessed by application server 116 via database services provided at a front end by database server 112, and store information on a variety of matters that is utilized in providing the services offered via the network service provided by the application server, as described below in greater detail.

The machine learning algorithm 15 instructs the service offer database 114h to store each healthcare service provider service corresponding to the user selection and displays the bundled set of service offers via the graphical user interface/provider portal 130 that matches the users' selection.

Any machine-learning algorithm 15 can be employed, such as neural networks, expert systems, Bayesian belief networks, fuzzy logic, data fusion engines and the like. The system may also employ combinations of various artificial intelligence techniques to the service offer database 114h.

The machine learning algorithm 15 takes into account of each and every parameter of user inputs such as type of disease, location, expertise, procedures, hospitals, pricing etc. Thus, the machine learning algorithm 15 displays the best results/hits based on the inputs and preferences of the user.

As used herein, the term "data store," "data storage unit," storage device", and the like can to any suitable memory device that may be used for storing data, including manual files, machine-readable files, and databases. In exemplary embodiments, application server 116, database server 112, and data store 114 may have implemented together a single computing device, implemented within a plurality of computing devices locally coupled to each other via a suitable communication medium, such as a serial port cable, telephone line or wireless frequency transceiver, implemented within a plurality of computing devices remotely coupled to each other via network 150, or any suitable combination thereof.

Client systems 140 are computer devices to which one or more users, which may be healthcare providers offering services or products or patients seeking to purchase healthcare services or products, or their human agents (for example, personal representatives or assistants), have access. It should be noted that the term "user" is used herein to refer to one who uses a computer system, such as one of client systems 140. As described in greater detail below, client systems 140 are each operable by such users to access server system 110 via network 150 and act as clients to access services offered by the network service provided by the server system within exemplary marketplace system 100. For this purpose, each client system includes a respective client application 142 that executes on the client system and allows a user to interact with server system 110 via application server 116.

In exemplary embodiments, the computer systems of client systems 140 can be any of a wide range of suitable computing devices such as one or more workstations, desktop computers, laptops, or other personal computers (PCs) (for example, IBM or compatible PC workstations running the MICROSOFT WINDOWS operating system or LINUX OS, MACINTOSH computers running the MAC OSX operating system, or equivalent), non-traditional-computer digital devices such as Personal Digital Assistants (PDAs) and other handheld or portable electronic devices, smart phones and other mobile handsets, tablet computers, netbook computers, game consoles, home theater PCs, desktop replacement computers, and the like, or any other suitable information processing devices. An exemplary computer system for client systems 140 is described in greater detail below with reference to FIG. 5.

In general, during operation of exemplary marketplace system 100, a client system 140 first establishes a connection to server system 110 via network 150. Once the connection has been established, the connected client system may directly or indirectly transmit data to and access content from the application server 116. A user accessing application server 116 through the connected client system can thereby to use a client application 142 to access services provided by the application server, which are described in greater detail below, via a user interface implemented by the client application within which the client application renders the information served by the application server.

In exemplary embodiments, application server 116 can implement network service as a non-web client application (such as a mobile application), a web client application, or both to provide the services accessed by client systems 140 within server system 110, and client applications 142 can correspondingly be implemented as non-web client applications, web client applications, or both for operation by users of the client systems to interact with application server 116 and access the services provided thereby. For example, application server 116 can comprise a web server configured to provide a web application for the respective client applications implemented on client systems 140 that are configured to provide web-based user interfaces for utilizing the services provided by the web server. For instance, the user interfaces of client applications implemented on client systems 140 can be configured to provide various options corresponding to the functionality offered in exemplary embodiments described herein through suitable user interface controls (for example, by way of menu selection, point-and-click, dialog box, or keyboard command). In one general example, the user interfaces may provide "send" or "submit" buttons that allow users of client applications to transmit requested information to application server 116. The user interfaces can be implemented, for example, as a graphical user interface (GUI) that renders a common display structure to represent the network service provided by application server 116 for a user of a client platform.

More specifically, in such an example, application server 116 can, for example, be configured to provide services via a web-based software application hosting a corresponding website that includes a number of web pages (e.g., screens), and client applications 142 can comprise a web browser executing on client systems 140, such that the services provided by application server 116 are accessible to client systems 114 using the Internet or an intranet. Users of client systems 140 may thereby access the website provided by application server 116 by, for example, inputting or following a link to the uniform resource locator (URL) for the website in the web browser, which then enable users to display and interact with information, media, and other content embedded within the web pages of the website provided by application server 116. The web-based software application can transmit information that can be processed by the web browsers to render a user interface using, for example, a browser-supported programming languages such as JavaScript, HTML, HTML5, and CSS, or the like, and can communicate with the web browsers using, for example, HTTPS, POST and/or GET requests. Client applications 142 and application server 16 may be configured so that information transmitted between client systems 140 and server system 110 can be encrypted and sent over a secure network connection to protect, for example, patient privacy.

Figure 2:
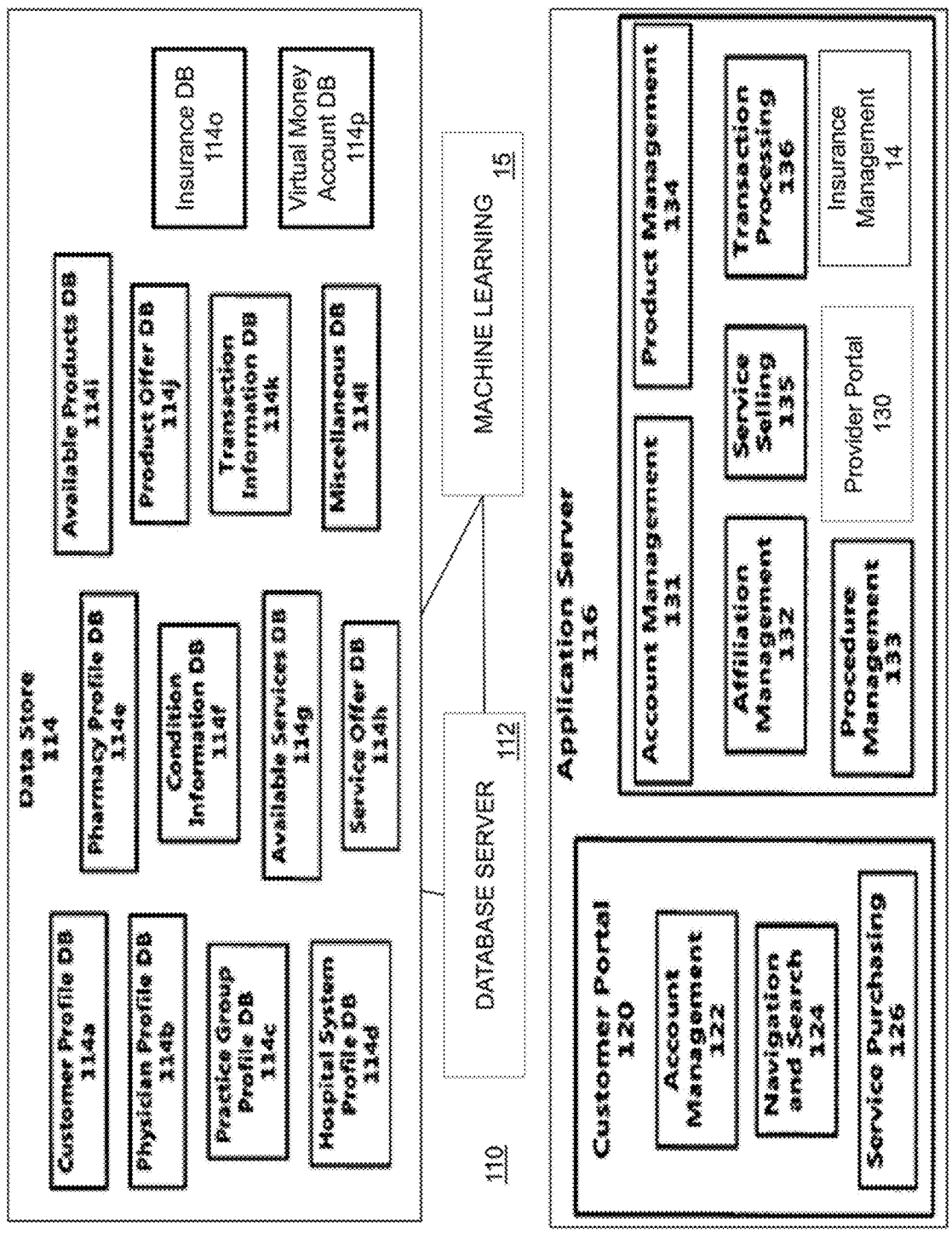
FIG. 2 is a block diagram illustrating a server system in accordance with an exemplary embodiment of the present invention.

Referring now to FIG. 2, a block diagram illustrating an exemplary embodiment of server system 110 is provided. As illustrated in FIG. 2, application server 116 is implemented to provide a plurality of services via a customer portal 120 and a plurality of services via a provider portal 130. As described herein, application server 116 can be implemented to provide a respective set services for each of various types of users (for example, unregistered guests, customers, individual physicians, nurses, office staff, practice group administrators, hospital system administrators, pharmacy administrators, and the like), and some of the services offered by application server 116 can be commonly applicable to and accessible by all types of users, while other services can be applicable to and accessible only by specific types of users.

For purposes of description, the terms "providers" and "provider users" are used herein to refer to the general class of users that register with the system offer healthcare services or products for purchase by customer users registered with the system, which can include individual physician users, practice group administrators, hospital system administrators, pharmacy administrators, and the like. In addition, a user account for a particular provider can have any number of authorized users. As an example, an account established for a physician can have the physician as one of its users. It can also have nurses or office staff working for the physician as other authorized users. The other authorized users can log into the account and perform various actions with the permission and under the supervision of the physician.

A single hospital system account may be established and shared by multiple staff member's hospital system. For purpose of illustration, there can be a designated user (for example, an account administrator) who is responsible for managing the account. The administrator can be provided with greater access rights within server system 110 with respect to the account. In exemplary embodiments, the particular client applications 142 or the particular client systems 140 that are utilized for accessing application server 116 can be respective to and customized for each type of user account. For example, the particular client application that is utilized for each type of account can be implemented to a provide virtual computing platform that is specific to the services offered for that type of account.

As further illustrated in exemplary embodiment of FIG. 2, and as will also be described in greater detail below, data store 114 comprises a plurality of databases that are maintained and accessible by application server 116 via database server 112, including a customer profile database 114a, a physician profile database 114b, a practice group profile database 114c, a hospital system profile database 114d, a pharmacy profile database 114e, a condition information database 114f, an available services database 114g, a service offer database 114h, an available products database 114i, a product offer database 114j, a transaction information database 114k, and one or more additional databases 114l that may be used for storing any other suitable information that may be utilized by server system 110 (for example, system usage data, audit trail data, data used internally within the system by application server 116, and the like).

The customer profile database 114a is configured to register users thereby providing user's personal information for purchasing healthcare services. The physician profile database 114b is configured to register and maintain records of individual physician offering healthcare services. The condition information database 114f is configured to register and maintain information records for various health conditions and diseases for which corresponding healthcare services are offered.

Physician profile database 114b is used to maintain account information records for individual physician users that register with server system 110 to offer healthcare services for purchase by customer users registered with the system, as well as account information records for individual physicians that are registered with the system in association with a practice group or hospital system (as described in greater detail below). For each physician for which an account is registered with server system 110, various items of information relevant to the physician, such as name, practice specialty, office location(s) and hours, a profile picture, contact information, biographical information (such as awards, honors, publications, patient testimonials, and other information that can be helpful for marketing the physician to customers accessing the system), URLs or references to websites and social media profiles, group practice and hospital affiliation(s), outside facilities that are used for particular procedures performed by the physician (for example, particular hospitals or clinics), compensation information (indicating a financial account for receiving payment for purchases of services offered by the physician via the system), and any other suitable identifying information, as well as a unique user name and password associated with the account that can be used to log into the account, may be included in the respective account information record for the physician that is maintained within physician profile database 114b. The account information record for each physician can also be associated with an account status and a unique physician account identifier within physician profile database 114b that is used by application server 116 for performing various operations.

Practice group profile database 114c is used to maintain account information records for practice group administrator users that register with server system 110 to offer healthcare services provided by physicians affiliated with a practice group for purchase by customer users registered with the system. For each practice group for which an account is registered with server system 110, various items of information relevant to the practice, such as practice group name, location and hours, contact information, URLs or references to websites and social media profiles for the practice group, physician and hospital affiliation(s), outside facilities that are used for particular procedures performed by physicians affiliated with the practice group, compensation information (indicating a financial account for receiving payment for purchases of services offered by affiliated physicians via the system), and any other suitable identifying information, as well as a unique user name and password associated with the account that can be used by the practice group administrator to log into the account, may be included in the respective account information record for the practice group that is maintained within practice group profile database 114c. The account information record for each practice group can also be associated with an account status and a unique practice group account identifier within practice group profile database 114c that may be used by physician users registered with the system for affiliating with the practice group and used by application server 116 for performing various operations.

The hospital system profile database 114d is configured to register and maintain account information records for hospital system administrators providing pre-paid healthcare services. Hospital system profile database 114d is used to maintain account information records for hospital system administrator users that register with server system 110 to make on-site, in-person sales of pre-paid healthcare services provided by physicians affiliated with a hospital system for purchase by patients operating client systems within marketplace system 100. For each hospital system for which an account is registered with server system 110, various items of information relevant to the hospital system, such as practice group and physician affiliation(s), facilities that are used for particular procedures performed by physicians affiliated with the hospital system, compensation information (indicating a financial account for receiving payment for purchases of services offered by affiliated physicians via the system), and any other suitable identifying information, as well as a unique user name and password associated with the account that can be used by the hospital system administrator to log into the account, may be included in the respective account information record for the hospital system that is maintained within hospital system profile database 114d. The respective account information record for the hospital system may further include a plurality of unique user names and passwords associated with the account that can be respectively used by hospital system staff members to log into the account The account information record for each hospital system can also be associated with an account status and a unique hospital system account identifier within hospital system profile database 114d that may be used by physician users registered with the system for affiliating with the hospital system and used by application server 116 for performing various operations.

Pharmacy profile database 114e is used to maintain account information records for pharmacy administrators that register with server system 110 to offer healthcare products, such as prescription drugs and medical supplies, for purchase by customer users registered with the system. For each pharmacy for which an account is registered with server system 110, various items of information relevant to the pharmacy, such as name, location(s) and hours, contact information, URLs or references to websites and social media profiles, compensation information (indicating a financial account for receiving payment for purchases of products offered by the pharmacy via the system), and any other suitable identifying information, as well as a unique user name and password associated with the account that can be used to log into the account, may be included in the respective account information record for the pharmacy that is maintained within pharmacy profile database 114e. The account information record for each pharmacy can also be associated with an account status and a unique pharmacy account identifier within pharmacy profile database 114e that is used by application server 116 for performing various operations.

Condition information database 114f is used to maintain information records for various health conditions and diseases for which corresponding healthcare services (for example, test and treatments) that can be offered by providers registered with server system 110 for purchase by customer users registered with the system. In exemplary embodiments, the various conditions, and diseases for which respective information records are maintained in condition information database 114f and the information that populates the respective information record for each condition or disease can be created and maintained by a back-end administrator of server system 110. For each condition or disease for which an information record is created, various items of information relevant to the condition or disease, such as name, description, causes, risk factors, symptoms, common treatments, corresponding healthcare services that can be offered by providers registered with server system 110 (for example, each associated healthcare service may be identified within the information record using a unique procedure identifier that is used to identify an information record for the service within available services database 114g as discussed below), and any other suitable information may be included in the respective information record for the condition or disease that is maintained within condition information database 114f.

The available service database 114g is configured to register and maintain records of various healthcare services offered by at least one of: a physician; and a hospital. Available services database 114g is used to maintain information records for various healthcare services (for example, test and treatments) that can be offered by providers registered with server system 110 for purchase by customer users registered with the server system. In exemplary embodiments, the respective information records for healthcare services that are maintained in available services database 114g and the information that populates the respective information record for each service can be created and maintained by a back-end administrator of server system 110. For each service for which an information record is created, various items of information relevant to the service, such as name, procedure detail, one or more medical specialties with which the procedure is commonly associated, cost information (for example, average prices for the service for patients that are uninsured and/or have a high deductible insurance plan and an average price for purchasing the service that is offered by providers registered with server system 110), a medical code number identifying the service according to the nomenclature used by a formal medical classification system (for example, a code that is used to identify the service according to the Current Procedural Terminology (CPT) code set), a procedure identifier that is used by application server 116 to uniquely identify the particular service, and any other suitable information may be included in the respective information record for the service that is maintained within available services database 114g.

Additionally, in exemplary embodiments, the information record for each service that is maintained within available services database 114g may further include an indication of the whether the service can be offered by providers within marketplace system 100 as an individual primary service or as a primary service of a bundled set of a plurality of services (for which a single payment for the bundled set of services will be disbursed to different provider for each of the services in the bundled set). In such embodiments, for each service for which the information record includes an indication that the service is offered as a primary service of a bundled set of services, various items of additional information relevant to the bundled set of services associated with the service that is indicated to be a primary service may be included in the respective information record for the primary service that is maintained within available services database 114g. Such items of information relevant to the bundled set of services included in the respective information record for a primary service may include, for example, items of information describing one or more secondary services associated with the primary service (such as name, a medical code number such as a CPT code identifying the service according to the nomenclature used by a formal medical classification system, and a secondary procedure identifier that is used by application server 116 to uniquely identify the particular secondary service in association with the unique procedure identifier for the primary service), one or more procedure identifiers for other services for which an information record is maintained within available services database 114g that are considered to be secondary services associated with the primary service, an indication of whether performance of each of the one or more secondary services (for which a single customer payment for the bundled set of services will be disbursed among different respective providers for the services in the bundled set) is optional or required in association with performance of the primary service, and an indication of whether the primary service is required to be performed at an outside facility. In addition, in such embodiments, for each service for which the information record includes an indication that the service is offered as a primary service of a bundled set of services, the cost information that is included in the respective information record for the primary service that is maintained within available services database 114g can include respective cost information for each of the primary service, the one or secondary services, and, if required, the use of an outside facility for the primary service individually (for example, average prices for each service and facility of the bundled set of services for patients that are uninsured and/or have a high deductible insurance plan) in addition to an average price for purchasing the bundled set of services that is offered by providers registered with server system 110.

Service offer database 114h is used to maintain information records for healthcare services that are being offered by providers registered with the system for purchase by customer users registered with the system. In this regard, it should be noted that the same service may be separately offered by multiple different providers registered with the system and, thus, service offer database 114h can include multiple information records for the same service that are each associated with a different provider. For each offered service for which a respective information record is maintained within service offer database 114h, various items of information relevant to the service being offered, such as the unique procedure identifier for the information record within available services database 114g for the service, the unique account identifier for the account information record (within physician profile database 114b, practice group profile database 114c, or hospital system profile database 114d) of the provider that is offering the service through the system, the unique physician account identifier for the account information record within physician profile database 114b of the physician user that will perform the service, a location at which the service will be performed, a discounted price for purchasing the service within marketplace system 100, a regular price for the service when the service is purchased outside of the system, the unique account identifier for the account information record (within physician profile database 114b, practice group profile database 114c, or hospital system profile database 114d) of the provider for which payment for the service when purchased through the system is to be directed, a payment amount to be transferred to the provider for which payment for performing the service is to be directed, additional descriptive information that may be provided by the provider offering the service, a procedure offer identifier that is used by application server 116 to uniquely identify the offering of the particular service by the provider within the system, and any other suitable information may be included in the respective information record for the offered service that is maintained within service offer database 114h.

Additionally, in exemplary embodiments, the information records for offered services that are maintained within service offer database 114h can include information records that include additional information for services that are offered by providers registered with the system as a bundled set of services. In this regard, the information record for each offered service that is maintained within service offer database 114h may further include an indication of the whether the offered service is being offered as an individual primary service or as a primary service of a bundled set of a plurality of services (for which a single customer payment for the bundled set of services will be disbursed among different respective providers for the services in the bundled set). In such embodiments, for each offered service for which the information record includes an indication that the service is being offered by a provider as a primary service of a bundled set of services, various items of additional information relevant to the bundled set of services associated with the offered service that is indicated to be a primary service may be included in the respective information record for the offered service that is maintained within service offer database 114h. Such items of information relevant to the bundled set of services included in the respective information record for an offered service within service offer database 114h that is indicated to be a primary service of a bundled set of services may include, for example, items of information for each secondary service such as the unique procedure identifier for the information record within available services database 114g for the secondary service (or the secondary procedure identifier that is included in the available services database 114g to uniquely identify the particular secondary service in association with the unique procedure identifier for the offered primary service where the information record for the primary service being offered in the available services database 114g includes an indication that the service is offered as a primary service of a bundled set of services), the unique physician account identifier for the account information record within physician profile database 114b of the physician user that will perform the secondary service, a location at which the service will be performed, a discounted price for purchasing the secondary service within marketplace system 100, a regular price for the secondary service when the service is purchased outside of the system, the unique account identifier for the account information record (within physician profile database 114b, practice group profile database 114c, or hospital system profile database 114d) of the provider for which payment for the secondary service when purchased through the system is to be directed, a payment amount to be transferred to the provider for which payment for performing the secondary service is to be directed, and an indication of whether performance of the secondary service is optional or required in association with performance of the primary service. The items of information relevant to the bundled set of services included in the respective information record for an offered service within service offer database 114h that is indicated to be a primary service of a bundled set of services may further include, for example, an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee.

Available products database 114i is used to maintain information records for various healthcare products (for example, prescription drugs and medical supplies) that can be offered by pharmacies registered with server system 110 (that is, pharmacies for which an account information record is maintained within pharmacy profile database 114e) for purchase by customer users registered with the system. In exemplary embodiments, the respective information records for the healthcare products that are maintained in available products database 114i and the information that populates the respective information record for each product can be created and maintained by a back-end administrator of server system 110. For each product for which an information record is created, various items of information relevant to the product, such as name(s), a list of dosage level options (for prescription drugs), size options (for certain medical supplies), and the like, a description of the product, an indication of whether a prescription is required to purchase the product, information for rendering a respective pre-defined fillable form for submitting prescription information for the product within a user interface, cost information (for example, average prices for the product for patients that are uninsured and/or have a high deductible insurance plan and a lowest price for purchasing the product that is offered for the service by pharmacies registered with server system 110), a product identifier that is used by application server 116 to uniquely identify the particular product, and any other suitable information may be included in the respective information record for the product that is maintained within available products database 114i.

Product offer database 114j is used to maintain information records for healthcare products that are being offered by pharmacies registered with the system for purchase by customer users registered with the system. In this regard, it should be noted that the same product may be separately offered by multiple different pharmacies registered with the system and, thus, product offer database 114j can include multiple information records for the same product that are each associated with a different provider. For each product offered by a pharmacy for which a respective information record is maintained within product offer database 114j, various items of information relevant to the product being offered, such as the unique product identifier for the information record within available products database 114i for the product, the unique pharmacy account identifier for the account information record within pharmacy profile database 114e of the pharmacy that is offering the product, a discounted price for purchasing the product from the identified pharmacy within marketplace system 100, a regular price for the product when the service is purchased outside of the system from the identified pharmacy, a payment amount to be transferred to the pharmacy that is offering the product, additional descriptive information that may be provided by the pharmacy offering the product, a product offer identifier that is used by application server 116 to uniquely identify the information record for the offering of the particular product by the pharmacy within the system, and any other suitable information may be included in the respective information record for the offered product that is maintained within product offer database 114j.

The transaction information database 114k is configured to maintain records of purchases made by registered users. Transaction information database 114k is used to maintain information records for purchases that have been made via the system by registered customer users of healthcare services and products being offered by registered providers. For each purchase of a service or product that has been made using the system, various items of information relevant to the purchase may be included in the respective information record for the purchase that is maintained within transaction information database 114k. In general, the items of information relevant to each purchase that is included in the respective information record for the purchase that is maintained within transaction information database 114k can include, for example, the unique customer account identifier of the account information record for the purchasing customer within customer profile database 114a, the unique procedure offer identifier of the information record for a purchased service within service offer database 114h or the unique product offer identifier of the information record for a purchased product within product offer database 114j, a purchase date, and a unique transaction identifier that is used by application server 116 to uniquely identify the information record for the purchase of the service or product within the system. For each purchase of a service that has been made using the system, the items of information relevant to the purchase included in the respective information record for the purchase that is maintained within transaction information database 114k may further include the unique physician account identifier for the account information record within physician profile database 114b of the physician user that is designated as performing the purchased service in the information record for the purchased service within service offer database 114h, an indication of whether the purchase has been redeemed and, if the purchase has been redeemed, a redemption date.

Additionally, in exemplary embodiments, the information records for purchased services that are maintained within transaction information database 114k can include information records that include additional information for purchases and services that are offered by providers registered with the system as a bundled set of services. In this regard, the information record for each purchased bundled set of services that is maintained within transaction information database 114k may include an indication of a particular outside facility that has been selected for performing the primary service of the bundled set of services and, for each service of the bundled set of services that is included within the purchase (for example, each required secondary service or each optional secondary service selected by the customer user to be included within the purchase, as well as the primary service), the unique physician account identifier for the account information record within physician profile database 114b of the physician user that is designated as performing the service in the information record for the purchased service within service offer database 114h, an indication of whether the purchase has been redeemed with respect to that particular service, and, if the purchase has been redeemed with respect to that particular service, a redemption date for that particular service.

Figure 3A:
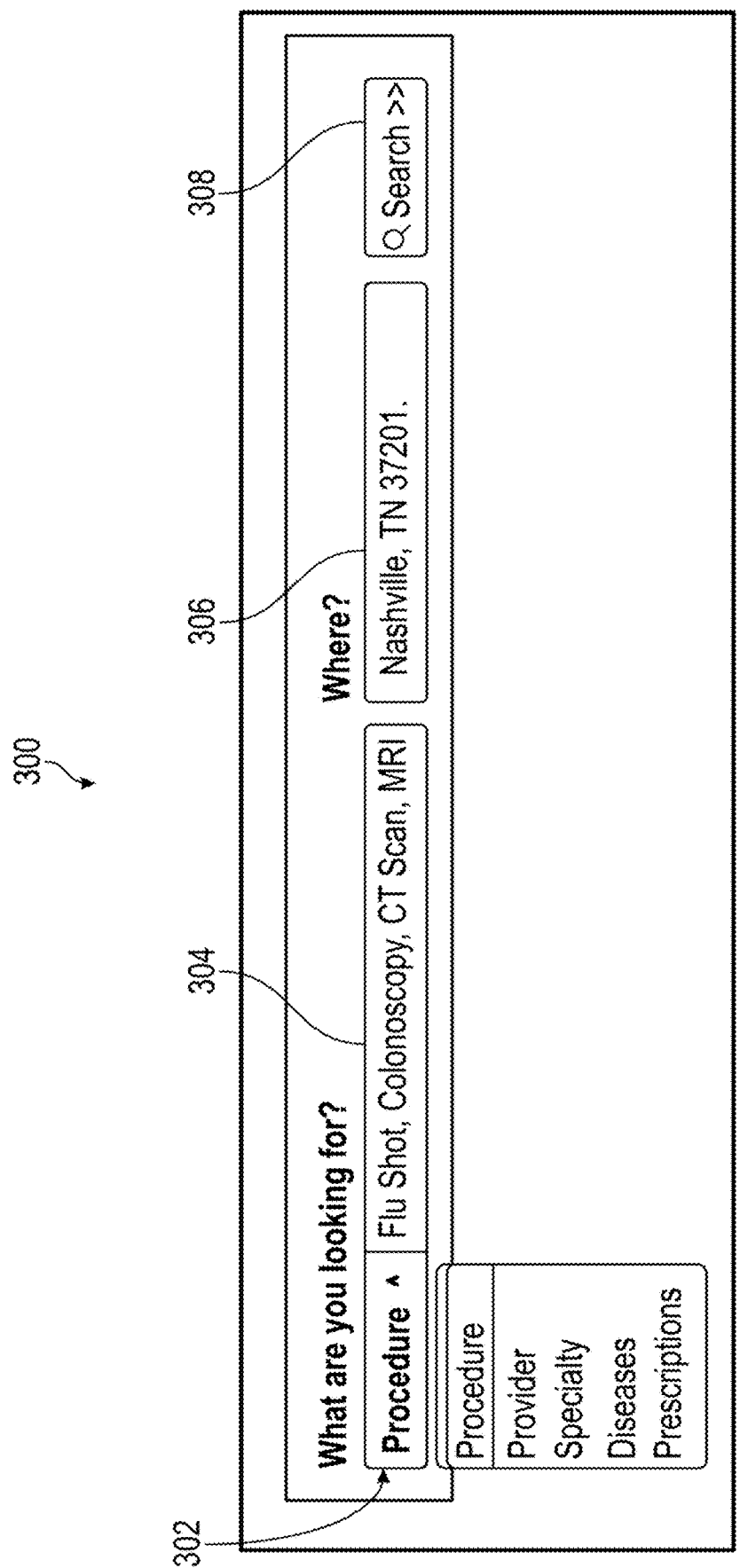
FIGS. 3A-3D are a number of screen shots illustrating examples of a graphical user interfaces that may be implemented by services provided within a customer portal in accordance with exemplary embodiments of the present invention.

FIG. 3A is a screen shot illustrating an example of a graphical user interface provided by such a home page 300 for customer portal 120. In the illustrated example, the search interface provided at home page 300 can include a drop-down menu 302, a search entry field 304, a location entry field 306, and a search button 308. Drop-down menu 302 provides a set of selectable options that allow the user to search for particular procedures offered by provider users registered with the system, particular products offered by pharmacy users registered with the system, information on providers registered with the system, and information on health conditions that is maintained within system. In exemplary embodiments, navigation, and search service 124 can be configured to use location information that may be gathered by any suitable location determining functionality implemented on the client system to provide a default location entry (for instance, city name and/or zip code) within location entry field 306. In such embodiments, navigation, and search service 124 may be further configured to request permission from the user via the user interface to be able to access and utilize such location information for this purpose.

In one example, when the user selects the option within drop-down menu 302 to search for a particular service offered by provider users registered with the system, the user can then proceed to enter the name of the service within search entry field 304 In conjunction with selecting the particular service, the user can also enter a city name and/or zip code or opt to utilize a default location entry within location entry field 306 to localize a search radius for providers offering the selected service for purchase via marketplace system 100.

Once the appropriate search information is entered, the user can then select the search button to direct navigation and search service 124 to conduct a search of local providers registered with server system 110 and offering the inputted healthcare service for purchase via marketplace system 100. Navigation and search service 124 can conduct such a location-based search by accessing, for example, service offer database 114*h* in conjunction with physician profile database 114*b*, practice group profile database 114*c*, hospital system profile database 114*d*, and/or any other suitable information and databases to which the application server has access to filter the information records included within available services database 114*g* for healthcare services that match the specified search criteria, and then present the results of the search to user within a search result listing page.

In exemplary embodiments, whenever navigation and search service 124 is directed to conduct a location-based search by a user (for example, for local providers offering the inputted healthcare service or, as discussed below, for local providers generally or for local pharmacy providers offering healthcare products), the navigation and search service can be configured to maintain the location specified within location entry field 306 for search within a data object for a session with application server 116 that is maintained for the user.

Figure 3B:
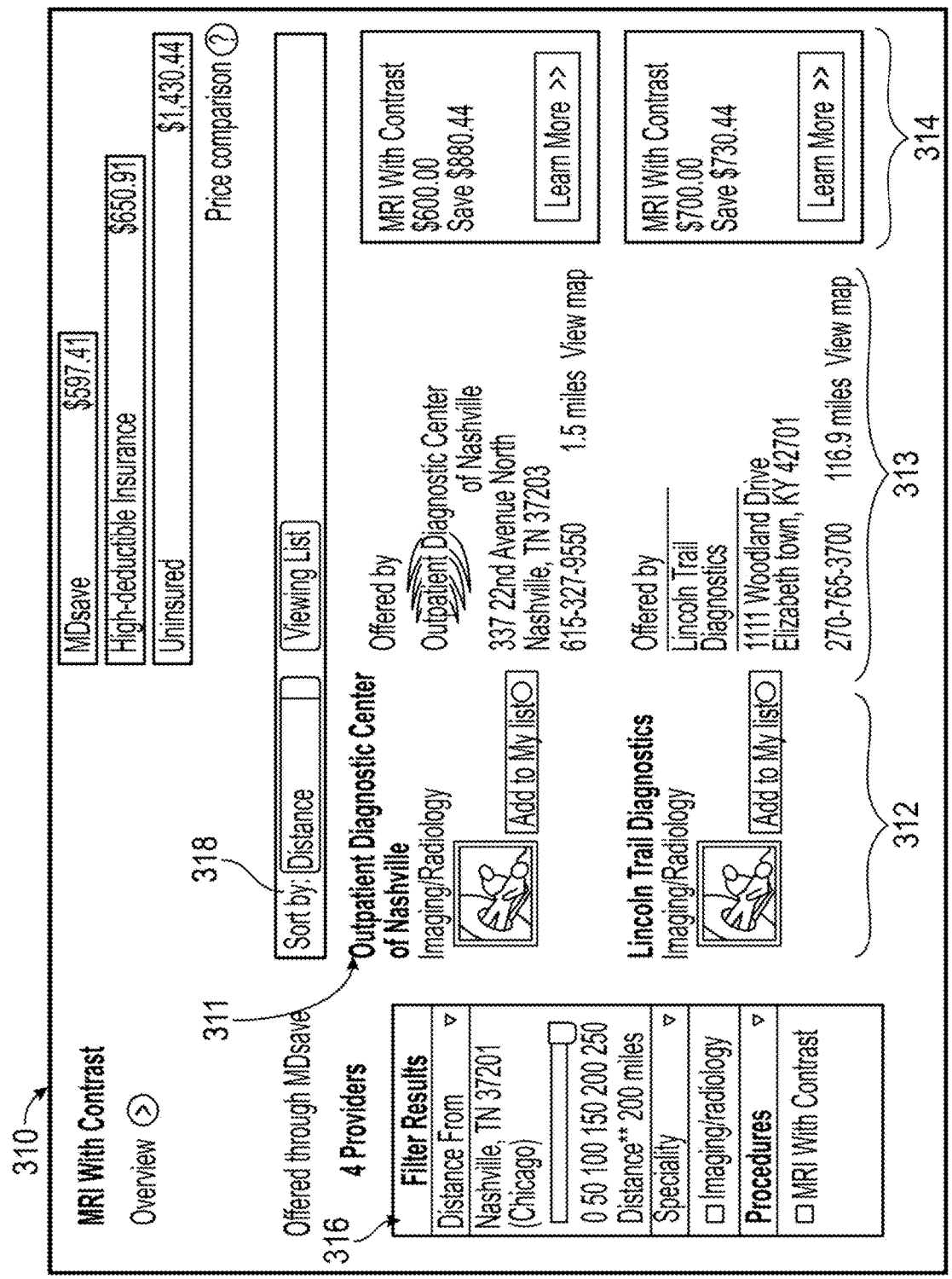

FIG. 3B is a screen shot illustrating an example of a GUI provided by a search result listing page 310 for customer portal 120 that presents a list of providers offering the service specified within search entry field 304 within a default search radius (for example, 50 miles) of the location specified within location entry field 306 returned in the search conducted by navigation and search service 124. In the illustrated example, search result listing page 310 includes a result listing section 311, a result filtering section 316, and a result sorting section 318. Result filtering section 316 provides various user interface controls for refining the results of the search presented within result listing section 311 by modifying the search criteria or inputting additional search criteria. In the illustrated example, result filtering section.

In exemplary embodiments, such a search result listing page 310 can be implemented to present any other appropriate information relevant to the search criteria specified by the user, such as, for example, a graphic depicting the average cost information included in the information record for the particular product specified in the search criteria that is maintained in available products database 114*j* (for prescription drug products, the average cost information can be provided for a default quantity of the prescription drug or, alternatively, based on a calculation performed by navigation and search service 124 for the quantity specified by the user using the average cost information for a default quantity as a reference). Each entry for an offered product listed in the product search result listing page can include portions presenting information from the account information record of the pharmacy that is offering the product through the system (for example, pharmacy name, address, and contact information), cost information for purchasing the offered product through marketplace system 100 (for example, the discounted price for the product that is specified in the information record for the offered product within product offer database 114*j* or, for prescription drugs, a price that is calculated based on the specified discounted price in relation to the quantity specified by the user) and a cost savings difference between the discounted price and the regular price for the product when the product is purchased outside of the system as specified in the information record for the offered product), and an option to select to purchase the offered product listed in the entry (for example, via an "Add to Cart" button). When a user selects the option to purchase an offered product listed in the product search result listing page, navigation and search service 124 can be configured to update the session data object for the session with application server 116 that is presently being maintained for the user to include an indication that the user has selected the offered product for purchasing (for example, by including the product offer identifier that is maintained within product offer database 114*j* to uniquely identify the offering of the particular product by the pharmacy) in association with any other required information (for example, in the case of a prescription drug, the quantity that is specified by the user and the price that is calculated based on the discounted price for the product that is specified in the information record for the offered product within product offer database 114*j* in relation to the quantity specified by the user). Upon selecting one or more services and/or products for purchase in association with a session with application server 116, the user may then have an option to navigate to a customer purchase page (for example, a "Check-Out" page) to proceed with purchasing the selected item(s) with respect to an account information record maintained within customer profile database 114*a* for a registered customer user.

For each offered service for which a respective entry is included in the purchase information section, the entry may include, for example, information retrieved from physician profile database 114*b*, available services database 114*g*, service offer database 114*h*, and the session data object such as the name of the physician that will perform the service, a service name, and an indication of whether the service is being offered as a primary service of a bundled set of services. Each entry for an offered service that is included in the purchase information section may further include user interface controls accessible by the user to remove the offered service from the purchase information section (and correspondingly direct purchasing service 126 to remove the indication the offered service as having been selected in the session data object) and/or to adjust a service quantity to be purchased by the user, and a price for purchasing the offered service that is calculated based on the service quantity specified by the user and the discounted price for the service that is specified in the information record for the offered service within service offer database 114*h* in relation to the quantity specified by the user.

In addition, for each entry for an offered service included in the purchase information section that is being offered as a primary service of a bundled set of services, the entry may further include user interface controls accessible by the user to present additional information about the bundled set of services and make additional selections regarding the offered service. The additional information may include, for example, information retrieved from physician profile database 114*b*, available services database 114*g*, and service offer database 114*h*, such as the name of physician that will perform each secondary service, a service name for each secondary service, an indication of whether each secondary service is required or optional, and an indication of whether the primary service is required to be performed at an outside facility. In association with each secondary service for which an indication that the secondary service is optional is presented, the additional information may further include the discounted price for the secondary service that is specified in the information record for the offered service within service offer database 114*h*, and an associated user interface control may be provided that allows the user to select whether to purchase the optional secondary service in association with the offered service. In association with an indication that the primary service is required to be performed at an outside facility, the additional information may further include name and location information for each facility for which information is specified in the information record for the offered service within service offer database 114*h*, and, if information is specified for more than one facility in the information record for the offered service, the facility fee for each specified facility may be presented in association with a user interface control that is provided to allow the user to select one of the facilities at which to have the primary service performed. Purchasing service 126 can be configured to, based on any optional secondary service and facility selections that are made by the user with respect to an entry for an offered service included in the purchase information section that is being offered as a primary service of a bundled set of services, recalculate and update the price for purchasing the offered service that is presented in the entry for the offered service. In exemplary embodiments, the default initial settings for any optional secondary service and multiple facility selections for a service being offered as a primary service of a bundled set of services and, thereby, the default initial price for purchasing the offered service that is presented in the entry for the offered service, may be based on a selection to purchase each optional secondary service and a selection of the facility having the lowest facility fee.

In the example screen shot depicted in FIG. 3B, each entry for an offered service listed in result listing section 311 includes a first portion 312 presenting information from the account information record within physician profile database 114*b* of the physician that will perform the service as specified in the information record for the offered service within service offer database 114*h* (for example, the physician's name, specialty, and profile picture), a second portion 313 presenting information from the account information record of the provider that is offering the service through the system (for example, provider name) and the location at which the offered service will be performed (for example, address and telephone number), and a third portion 314 presenting cost information for purchasing the offered service through application server 116 (for example, the discounted price for the service that is specified in the information record for the offered service within service offer database 114*h* and a cost savings difference between the discounted price and the regular price for the service when the service is purchased outside of the system from the provider as specified in the information record for the offered service within service offer database 114*h*), and an option to select to purchase the offered service listed in the entry (for example, via an "Add to Cart" button included within third portion 314). When a user selects the option to purchase an offered service listed in result listing section 311, navigation and search service 124 can be configured to update the session data object for the session with application server 116 that is presently being maintained for the user to include an indication that the user has selected the offered service for purchasing (for example, by including the procedure offer identifier that is maintained within service offer database 114*h* to uniquely identify the offering of the particular service by the provider).

Figure 3C:
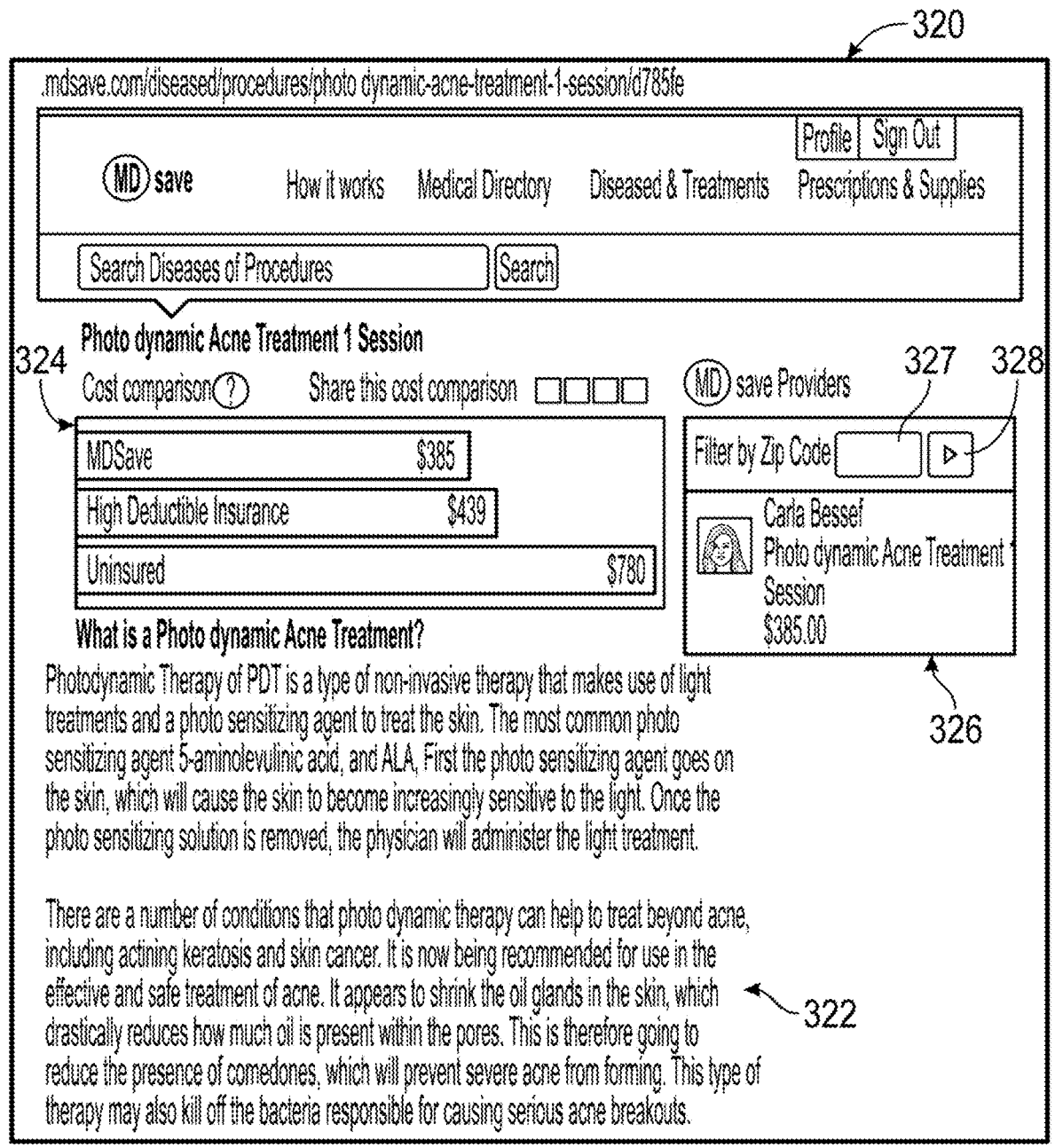

Referring now to FIG. 3C, a screen shot illustrating an example of a GUI provided by a healthcare service information page 320 implemented by navigation and search service 124 for a particular healthcare service is provided. In the illustrated example, healthcare service information page 320 includes a procedure overview section 322, a cost comparison graphic 324, and a provider listing section 326.

The information presented in provider listing section 326 can be generated in a manner similar to the information included in result listing section 311 of example search result listing page 310 depicted in FIG. 3B to present a list of providers offering the particular service within a default search radius (for example, 50 miles) of a location determined by navigation and search service 124. The particular location that is utilized for this purpose may be determined using, for example, a location that is stored within the session data object for the session with application server 116 that is presently being maintained for the user or location information that is gathered by any suitable location determining functionality implemented on the client system to provide a default location entry. In the present example, provider listing section 326 presents an entry for each offered service for which a respective information record is maintained within service offer database 114*h* that matches the particular service for which healthcare service information page 320 is generated and along with the determined location. Each entry for an offered service listed in provider listing section 326 presents information from the account information record within physician profile database 114*b* of the physician that will perform the service as specified in the information record for the offered service within service offer database 114*h* (for example, the physician's name and profile picture) and cost information for purchasing the offered service through application server 116 (for example, the discounted price for the service that is specified in the information record for the offered service within service offer database 114*h*). In the present example, provider listing section further includes a location entry field 327 that, in conjunction with a "submit" button 328, allows a user to specify a particular location (for example, a city name and/or zip code) and submit a request for navigation and search service 124 to conduct a search and update the information presented in provider listing section 326 to present a list of providers offering the particular service within the default search radius of the newly specified location. Navigation and search service 124 can also be configured to, in response to such a request, update the location that is maintained within the session data object for the session with application server 116 that is presently being maintained for the user.

Figure 3D:

In exemplary embodiments, as further illustrated in FIG. 3D, physician information section 332 can further include additional user interface elements such as a "Leave a review" button 333, a "Request an appointment" button 334, and a map element 335 depicting a mapped location of an office location included within respective account information record that is maintained for the particular physician user in physician profile database 114*b* (which navigation and search service 124 may be configured to generate by remotely accessing a third-party mapping service). In response to a user selecting "Leave a review" button 333, navigation and search service 124 can be configured to implement suitable user interface controls for allowing the user to post or submit a review of the particular physician to server system 110. In response to receiving such a review, navigation and search service 124 can be configured to, for example, include information pertaining to the review within the respective account information record that is maintained for the particular physician user in physician profile database 114*b* or send an electronic message to the physician user pertaining to the review, for example, by way of email utilizing the contact information specified in the respective account information record for the physician.

In response to a user selecting "Request an appointment" button 334, navigation and search service 124 can be configured to implement suitable user interface controls for allowing the user to submit a request for scheduling an appointment to the particular physician user (for example, by sending a notification to the physician user by utilizing the contact information specified in the respective account information record for the physician that includes contact information for the user). Navigation and search service 124 may also be configured to implement suitable user interface controls for allowing the user to schedule an appointment with the particular physician user. Navigation and search service 124 may provide this functionality by, for example, accessing a service with which the particular physician user is associated, which may be a service offered by application server 116 or offered by a third-party service provider.

In the present example, as illustrated in FIG. 3D, the information presented in offered procedures section 336 of physician profile page 330 can include a listing of healthcare services offered by the particular physician for purchase through marketplace system 100.

In the illustrated example, physician profile page 330 includes a physician information section 332 and an offered procedures section 336. The information presented in physician information section 332 can be generated based on the information that is included in the respective account information record that is maintained for the particular physician user in physician profile database 114*b* and may include various items of information relevant to the physician, such as name, practice specialty, office location(s) and hours, a profile picture, contact information, biographical information (such as awards, honors, publications, patient testimonials, and other information that may be of interest to prospective customers accessing the system), URLs or references to websites and social media profiles, and group practice and hospital affiliation(s).

In exemplary embodiments, the user interface implemented by account management service 122 may be further configured to provide user interface controls for requesting authorization for payment of a predetermined fee to gain access to the ability to make prepaid purchases of healthcare services and products offered within marketplace system 100. The payment information input by the user may be an instruction to use the billing information included within the respective account information record established for the user within customer profile database 114*a* or submission of alternative payment information such as, for example, bank account information, credit or debit card information, or other electronic payment information (such as information for utilizing an account the user has with PayPal or any another entity facilitating payments and money transfers to be made through the Internet), which may be for an account maintained for the user or an account maintained for another person or entity that the user is authorized to utilize for this purpose.

Account management service 122 can be configured to, upon the authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. In this regard, the respective account information record established for the user within customer profile database 114*a* can further include an account status that is managed by account management service 122 for the user indicating whether the user is presently provided with the ability to make prepaid purchases of healthcare services and products offered within marketplace system 100.

Upon a user registering a customer account with server system 110 to establish an account information record within customer profile database 114*a* and logging into his or her customer account (for example, by accessing a login user interface element or a login screen within the user interface implemented by customer portal 120 to provide the user name and password associated with the account), the user then proceeds with purchasing any offered service or product for which the session data object for the session with application server 116 that is being maintained for the user includes an indication that the user has selected for purchasing. For example, upon the user selecting an option within the user interface implemented by navigation and search services 124 to navigate to a customer purchase page and initiate a purchasing session with purchasing service 126 to purchase one or more of the offered items indicated as having been selected by the user in the session data object in association with the registered customer account for the user.

The purchase information section included within the user interface implemented for the payment page may further include a total price for the purchase that is equal to a sum of the respective price for purchasing the corresponding offered item included for each entry included in the purchasing information section. In exemplary embodiments, purchasing service 126 may be configured to adjust the total price based on any applicable state taxes or any discount codes submitted by the user. In this regard, purchasing service 126 may be further implemented to provide a user interface element allowing a user to submit any application discount codes to application server 116.

For this purpose, the user interface controls implemented within a payment section may include a button that is accessible by the user to provide authorization for the request to be issued to the specified funding source (for example, a "Submit" or "Purchase" button) along suitable user interface elements accessible by the user to input the purchase information specifying the funding source to use for the purchase. The purchase information input by the user may be an instruction to use the billing information included within the respective account information record for the customer account of the user within customer profile database 114*a* or submission of alternative purchase information such as, for example, bank account information, credit or debit card information, or other electronic payment information (such as information for utilizing an account the user has with PayPal or any another entity facilitating payments and money transfers to be made through the Internet). The purchase information may, for example, specify an account maintained for the user, an account maintained for another person or entity that the user is authorized to utilize for this purpose, or an entity that has arranged to be invoiced and provide reimbursement for purchases of healthcare services and products made by the user within marketplace system 100.

Figure 4A:
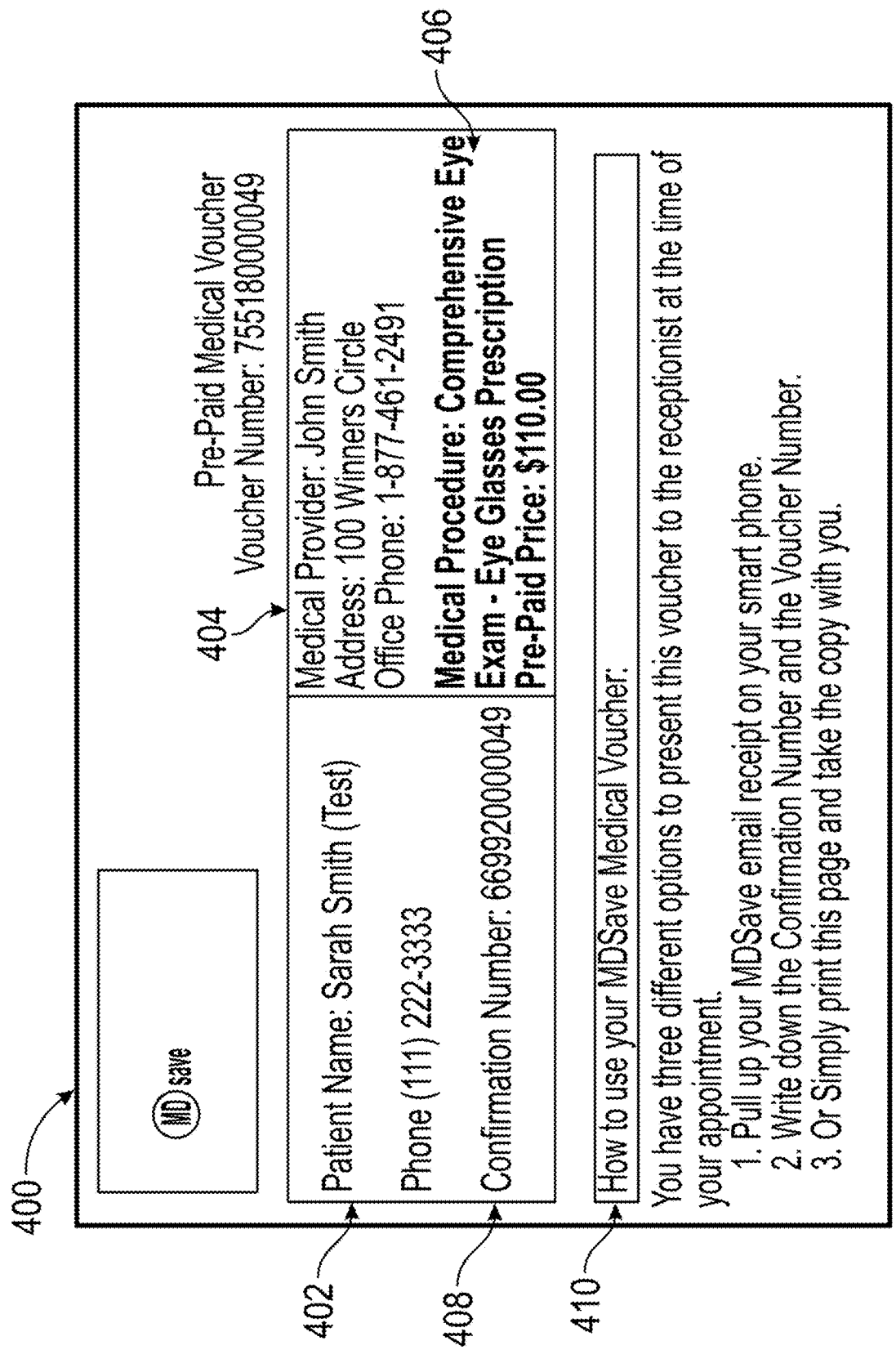
FIG. 4A is an illustration of an example voucher that may be generated within a user interface by functions provided within a customer portal for a purchased service in accordance with exemplary embodiments of the present invention.

Purchasing server 126 can also be configured to, upon processing the payment for the purchase of the offered service, generate a voucher for the customer user within the user interface for the purchased service that can be utilized by the customer user to redeem the purchase and receive the service from the physician specified for the offered service (the providers of marketplace system 100 can have pre-arranged agreements with providers registered with the system that the providers will agree to honor such vouchers generated by purchasing server 126 for purchased services). An example of such a voucher is illustrated in FIG. 4A. As depicted in the example, example voucher 400 can be generated to include identifying information for the customer user 402, identifying and contact information for the physician specified for the offered service 404, a description of the purchased service 406, a confirmation number 408 for the purchase, which may be generated by purchasing server 126 based on the unique transaction identifier that is included in the respective information record for the purchase that is maintained within transaction information database 114*k*, and instructions for redeeming the voucher 410. The confirmation number may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine readable form.

Purchasing server 126 can be configured to, upon processing the payment for the purchase of the offered service that is being offered as a primary service in conjunction with a bundled set of services, navigate the user interface to a purchase confirmation page and send an electronic confirmation message to the customer user and electronic notifications to each physician that will perform a service of the bundled set of services and the provider user for the offered service (as specified according to the information record for the offered service within service offer database 114*h*), for example, by way of email utilizing the contact information specified in the respective account information records for the customer, the physicians, and the provider for the offered service. Purchasing server 126 can also be configured to generate a respective information record for the completed purchase with corresponding information within transaction information database 114*k*, which initially indicates that the purchase has not yet been redeemed with respect to the primary service, each secondary service, and any facility specified for the purchased offered service.

Purchasing server 126 can also be configured to, upon processing the payment for the purchase of the offered service that is being offered as a primary service in conjunction with a bundled set of services, generate a voucher for the customer user within the user interface for the purchased service that can be utilized by the customer user to redeem the purchase and receive the service from the corresponding physician specified for each of the services of the bundled set of services (the providers of marketplace system 100 can have pre-arranged agreements with providers registered with the system that the providers will agree to honor such vouchers generated by purchasing server 126 for purchased services). An example of such a voucher for a bundled set of services is illustrated in FIG. 4B. As depicted in the example, example voucher 400 can be generated to include identifying information for the customer user 402, identifying and contact information for each physician specified for a service and any facility included in the offered service 404, a description of each service of the purchased service 406, a confirmation number 408 for the purchase, which may be generated by purchasing server 126 based on the unique transaction identifier that is included in the respective information record for the purchase that is maintained within transaction information database 114*k*, and instructions for redeeming the voucher 410. The confirmation number (or any other suitable redemption information such as a one or two dimensional bar code, a QR code, or any other form of machine readable information) may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine readable form.

Upon the user indicating an intention to register as a physician user, the user will be able to initiate a registration session with account management service 131 to register a physician account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within physician profile database 114*b* such as, for example, name, practice specialty, office location(s) and hours, a profile picture, contact information (such as an email address and/or a telephone number), biographical information (such as awards, honors, publications, patient testimonials, and other information that can be helpful for marketing the physician to customers accessing the system), URLs or references to websites and social media profiles, compensation information (indicating a financial account for receiving payment for purchases of services offered by the physician via the system), information pertaining to outside facilities that are used for particular services performed by the physician (for example, information pertaining to particular hospitals or clinics such as name, address, contact information, facility fee, and compensation information indicating a financial account that is used by the facility for receiving a facility fee), and any other suitable identifying or descriptive information. The user interface may also be implemented by account management service 131 to prompt the user for any group affiliation codes or hospital affiliation codes.

Procedure management service 133 may be configured, for example, to implement a user interface that includes a series of pages with user interface controls accessible by the user to guide the user through the service offering process and prompt the user to input various types of information to be maintained by database server 112 within a respective information record that is established in association with the unique physician account identifier for the physician within service offer database 114h. Upon the user indicating an intention to offer a healthcare service for purchase (for example, by selecting a "Offer Service" tab within the practice group account page implemented by provider portal 130), the user will be able to initiate a service offering with procedure management service 133 to offer a healthcare service performed by affiliated physicians for purchase via server system 110. For example, the user may be provided with a drop-down menu providing a list of selectable medical specialties and, upon selecting a particular medical specialty, the user can be presented with a list of selectable healthcare services for which an information record for the service is maintained within available services database 114g in association with the specialty.

Upon the user selecting a particular service from this list, procedure management service 133 can assist the user with offering the service for purchase and establish the respective information record for the offered service within service offer database 114h. In particular, procedure management service 133 can present the user with a selectable list of the physician users affiliated with the practice group from which the user can submit an indication one or more of the affiliated physicians with which to offer the service in conjunction with the practice group account. For each selected affiliated physician user, procedure management service 133 can establish a respective information record for the offered service within service offer database 114h by populating the information record with the unique procedure identifier for the information record within available services database 114g for the selected service, the unique account identifier for the account information record for the practice group within physician profile database 114b as the provider that is offering the service through the system, the unique account identifier for the account information record for the physician user within physician profile database 114b as the physician user will perform the service, a location at which the service will be performed, the unique account identifier for the account information record (within physician profile database 114b, practice group profile database 114c, or hospital system profile database 114d) of the provider for which payment for the service when purchased through the system is to be directed (or, alternatively, other financial account information) as indicated by user input received from the practice group administrator, a payment amount to be transferred to the provider or other financial account for which payment for the service is to be directed as specified by user input received from the practice group administrator, a discounted price for purchasing the service within marketplace system 100 (which may be calculated, for example, by adding a negotiated commission fee to the payment amount specified by the practice group administrator), a regular price for the service when the service is purchased outside of the system, additional descriptive information that may be provided via input received from the practice group administrator, a procedure offer identifier, and any other suitable information (such as an indication that the service is required to be performed at an outside facility and relevant facility information as specified by user input received from the practice group administrator).

In exemplary embodiments, procedure management service 133 can also assist the practice group administrator with offering services for purchase as a bundled set of services within marketplace system 100 and establishing the respective information record for the service offered as a bundled set of services within service offer database 114h. In particular, procedure management service 133 can present the user with an option to indicate that a particular service selected by the user should be offered as a primary service of a bundled set of services or, alternatively, the information record for a particular service selected by the user that is maintained within available services database 114g can include an indication that the service can be offered by providers within marketplace system 100 as a primary service of a bundled set of a plurality of services.

For a selected service for which such an indication is provided, procedure management service 133 may be configured, for example, to implement user interface controls accessible by the user to guide the user through the process for offering the selected service as a primary service of a bundled set of services and prompt the user to input various types of information to populate a respective information record that is established in association with the unique practice group account identifier for the practice group within service offer database 114h. Procedure management service 133 can first present the user with a selectable list of the physician users affiliated with the practice group from which the user can submit an indication of affiliated physicians with which to offer the primary service in conjunction with the practice group account and then populate the information pertaining to the primary service in the information record with the unique procedure identifier for the information record within available services database 114g for the selected service, the unique account identifier for the account information record for the practice group within physician profile database 114b as the provider that is offering the primary service through the system, the unique account identifier for the account information record for the physician user within physician profile database 114b as the physician user will perform the primary service, a location at which the primary service will be performed, the unique account identifier for the account information record (within physician profile database 114b, practice group profile database 114c, or hospital system profile database 114d) of the provider for which payment for the primary service when purchased through the system is to be directed (or, alternatively, other financial account information) as indicated by user input received from the practice group administrator, a payment amount to be transferred to the provider or other financial account for which payment for the primary service is to be directed as specified by user input received from the practice group administrator, a discounted price for purchasing the primary service within marketplace system 100 (which may be calculated, for example, by adding a negotiated commission fee to the payment amount for the primary service specified by the practice group administrator), a regular price for the primary service when the primary service is purchased outside of the system, additional descriptive information that may be provided via input received from the practice group administrator, a procedure offer identifier, and any other suitable information.

Procedure management service 133 can then receive an indication, either from the information record for a particular service selected by the user that is maintained within available services database 114g or through selections made by the user of services offered by affiliated physicians for which an information record for the service is maintained within available services database 114g, of one or more secondary services to be included in the bundled set of services. Procedure management service can then populate the information pertaining to each secondary service in the information record with the unique procedure identifier for the information record within available services database 114g for the secondary service (or the secondary procedure identifier that is included in the available services database 114g to uniquely identify the particular secondary service in association with the unique procedure identifier for the offered primary service where the information record for the primary service being offered in the available services database 114g includes an indication that the service is offered as a primary service of a bundled set of services), the unique physician account identifier for the account information record within physician profile database 114b of the physician user that will perform the secondary service, a location at which the service will be performed, the unique account identifier for the account information record (within physician profile database 114b, practice group profile database 114c, or hospital system profile database 114d) of the provider for which payment for the primary service when purchased through the system is to be directed (or, alternatively, other financial account information) as indicated by user input received from the practice group administrator, a payment amount to be transferred to the provider or other financial account for which payment for the secondary service is to be directed as specified by user input received from the practice group administrator, a discounted price for purchasing the secondary service within marketplace system 100 (which may be calculated, for example, by adding a negotiated commission fee to the payment amount for the secondary service specified by the practice group administrator), a regular price for the secondary service when the secondary service is purchased outside of the system, and an indication of whether performance of the secondary service is optional or required in association with performance of the primary service. Procedure management service can further populate the information in the information record with an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee (as specified by user input received from the practice group administrator).

Upon the user indicating an intention to request payment for a purchased service that have been performed (for example, by selecting a "Voucher Processing" tab within the physician account page implemented by provider portal 130), the user will be able to initiate a voucher processing session with transaction processing service 136. In particular, transaction processing service 136 may be configured, for example, to implement a voucher history page within the user interface that presents information relevant to the physician user for a list of purchases for which the respective information record for the purchase that is maintained within transaction information database 114k includes the unique physician account identifier for the physician user within physician profile database 114b as the physician user that is designated as performing a service included the purchase (for example, a primary or secondary service for a bundled set of services). The relevant information for each listed purchase may include, for example, the voucher confirmation number or redemption code, name and contact information for the customer user, a description of the service the physician user is designated as performing for the purchase, a purchase date, and a voucher redemption status. Such a voucher history page may also be accessed in association with the user account for the physician user to verify vouchers presented customers requesting to have a service performed in association with a voucher.

The voucher history page can also provide a user interface element in association with each of the listed purchases for which the voucher redemption status for the service the physician user is designated as performing indicates the service has not been performed that is accessible by the physician user to submit a verification to application server 116 that the physician user has performed the service for the customer user in accordance with the purchase.

Referring again to FIG. 2, in exemplary embodiments, when a user operating a client system to access application server 116 via a corresponding client application executing on the client system initiates a registration with server system 110 and specifies an intention to register as a practice group administrator (for example, via a user interface element on any page implemented by navigation and search service 124), the user will be able to initiate a registration session with account management service 131 to register a practice group account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within practice group profile database 114c such as, for example, practice group name, location and hours, contact information (such as an email address and/or a telephone number), URLs or references to websites and social media profiles for the practice group, information pertaining to outside facilities that are used for particular procedures by physicians affiliated with the practice group, (for example, information pertaining to particular hospitals or clinics such as name, address, contact information, facility fee, and compensation information indicating a financial account that is used by the facility for receiving a facility fee), compensation information (indicating a financial account for receiving payment for purchases of services that are performed by affiliated physicians via the system), and any other suitable identifying or descriptive information.

The voucher history page can also provide a user interface element in association with each of the listed purchases for which the voucher redemption status for the service indicates the service has not been performed that is accessible by the practice group user to submit a verification to application server 116 that the affiliated physician user specified as performing the service has performed the service for the customer user in accordance with the purchase.

In exemplary embodiments, when a user operating a client system to access application server 116 via a corresponding client application executing on the client system initiates a registration with server system 110 and specifies an intention to register as a hospital system administrator (for example, via a user interface element on any page implemented by navigation and search service 124), the user will be able to initiate a registration session with account management service 131 to register a hospital system account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within hospital system profile database 114*d* such as, for example, contact information (such as an email address and/or a telephone number), information pertaining to outside facilities that can be used for particular procedures by physicians affiliated with the hospital system (for example, information pertaining to particular hospitals or clinics such as name, address, contact information, facility fee, and compensation information indicating a financial account for that is used by the facility for receiving a facility fee), compensation information (indicating a financial account for receiving payment for purchases of services performed by affiliated physicians via the system), and any other suitable identifying or descriptive information.

In exemplary embodiments, the functionality that is provided within provider portal 130 for users of hospital system accounts can vary in certain respects from the functionality that may be provided within provider portal 130 for users of practice group accounts. For example, with respect to physicians that are affiliated with the hospital system account, users of hospital system accounts may only be provided with access rights (for example, to view, modify, and specify in a service being offered by the hospital system for purchase) to services offered for purchase by affiliated physician users that have been specified by the physician users as being hospital procedures with respect to the physician accounts. Hospital system users may also be provided with functionality to, as an alternative to selecting a service by accessing a list of selectable medical specialties when initiating a service offering with procedure management service 133 to offer a service performed by affiliated physicians for purchase via server system 110, submit a search query for a service by inputting descriptive terms or a medical code number that is used to identify the service (for example, according to the CPT code set) or access a list of affiliated physicians and, upon selecting a particular affiliated physician from the list, be presented with a list of selectable healthcare services for which an information record for the service is maintained within service offer database 114*h* that indicates the selected physician as the physician that will perform the service.

In addition, because a hospital system may be more likely to offer a higher quantity of services for purchase as a bundled set of services within marketplace system 100 than other types of provider users, the functionality implemented by provider portal 130 within the user interface for allowing a user of a hospital system account to manage information pertaining to services offered by the hospital system for purchase and to view a history of transactions performed for services offered for purchase by the hospital system within server system 110 may include an additional user interface element that is accessible by a user for the hospital system account manage and view information pertaining to only services that are offered by the hospital system as a bundled set of services.

Figure 5:
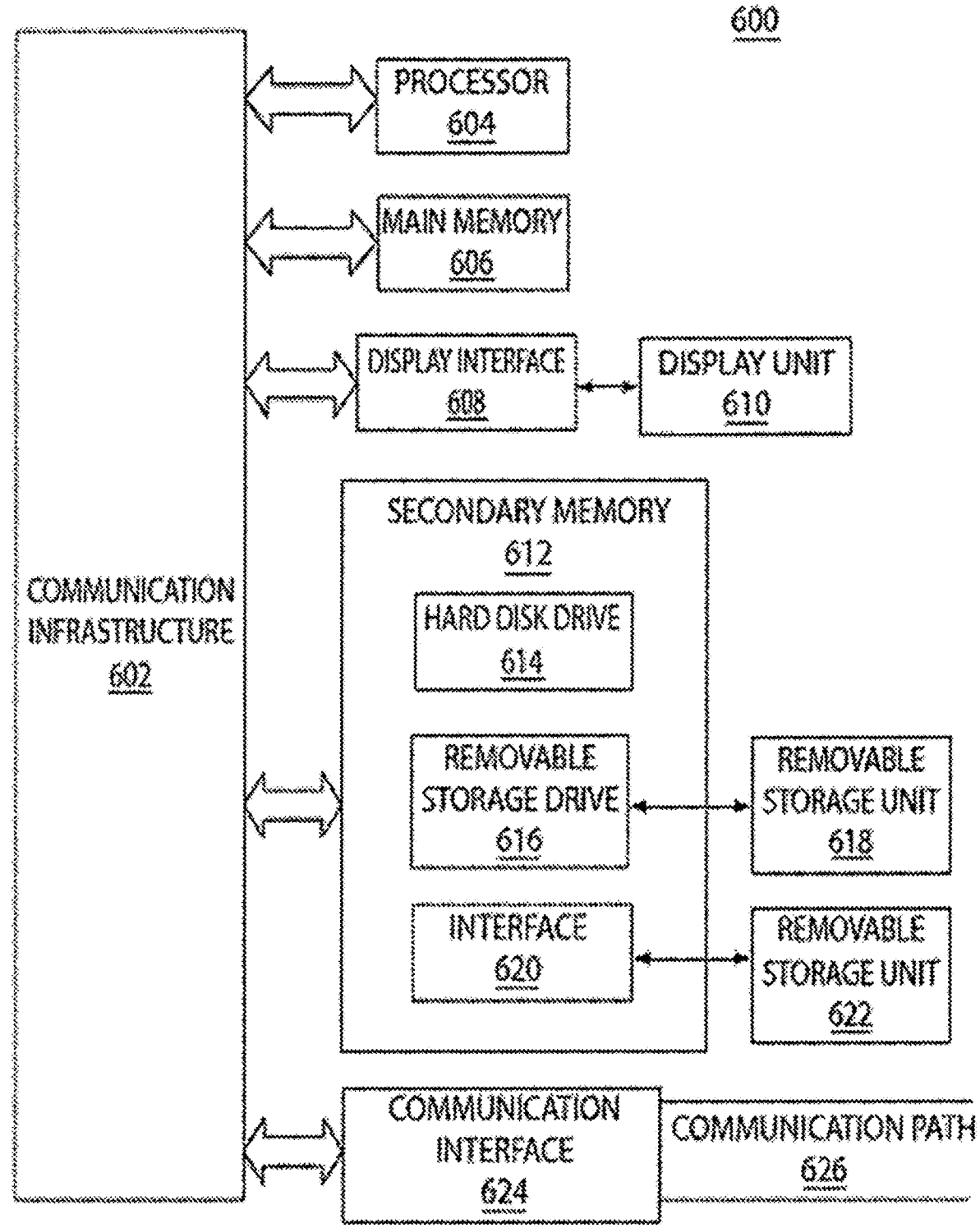
FIG. 5 is a block diagram of an exemplary computer system that can be used for implementing exemplary embodiments of the present invention.

FIG. 5 is a block diagram of an exemplary computer system 600 that can be used for implementing exemplary embodiments of the present invention. Computer system 600 includes one or more processors, such as processor 604. Processor 604 is connected to a communication infrastructure 602 (for example, a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

Exemplary computer system 600 can include a display interface 608 that forwards graphics, text, and other data from the communication infrastructure 602 (or from a frame buffer not shown) for display on a display unit 610. Computer system 600 also includes a main memory 606, which can be random access memory (RAM), and may also include a secondary memory 612. Secondary memory 612 may include, for example, a hard disk drive 614 and/or a removable storage drive 616, representing a floppy disk drive, a magnetic tape drive, an optical disk drive, etc. Removable storage drive 616 reads from and/or writes to a removable storage unit 618 in a manner well known to those having ordinary skill in the art. Removable storage unit 618, represents, for example, a floppy disk, magnetic tape, optical disk, etc. which is read by and written to by removable storage drive 616. As will be appreciated, removable storage unit 618 includes a computer usable storage medium having stored therein computer software and/or data.

In exemplary embodiments, secondary memory 612 may include other similar means for allowing computer programs or other instructions to be loaded into the computer system. Such means may include, for example, a removable storage unit 622 and an interface 620. Examples of such may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between the computer system and external devices. Examples of communications interface 624 may include a modem, a network interface (such as an Ethernet card), a communications port, a PCMCIA slot and card etc. Software and data transferred via communications interface 624 are in the form of signals which may be, for example, electronic, electromagnetic, optical, or other signals capable of being received by communications interface 624. These signals are provided to communications interface 624 via a communications path (that is, channel) 626. Channel 626 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 606 and secondary memory 612, removable storage drive 616, a hard disk installed in hard disk drive 614, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It can be used, for example, to transport information, such as data and computer instructions, between computer systems. Furthermore, the computer readable medium may comprise computer readable information in a transitory state medium such as a network link and/or a network interface including a wired network or a wireless network that allow a computer to read such computer readable information.

Computer programs (also called computer control logic) are stored in main memory 606 and/or secondary memory 612. Computer programs may also be received via communications interface 624. Such computer programs, when executed, can enable the computer system to perform the features of exemplary embodiments of the present invention as discussed herein. In particular, the computer programs, when executed, enable processor 604 to perform the features of computer system 600. Accordingly, such computer programs represent controllers of the computer system.

Figure 6:
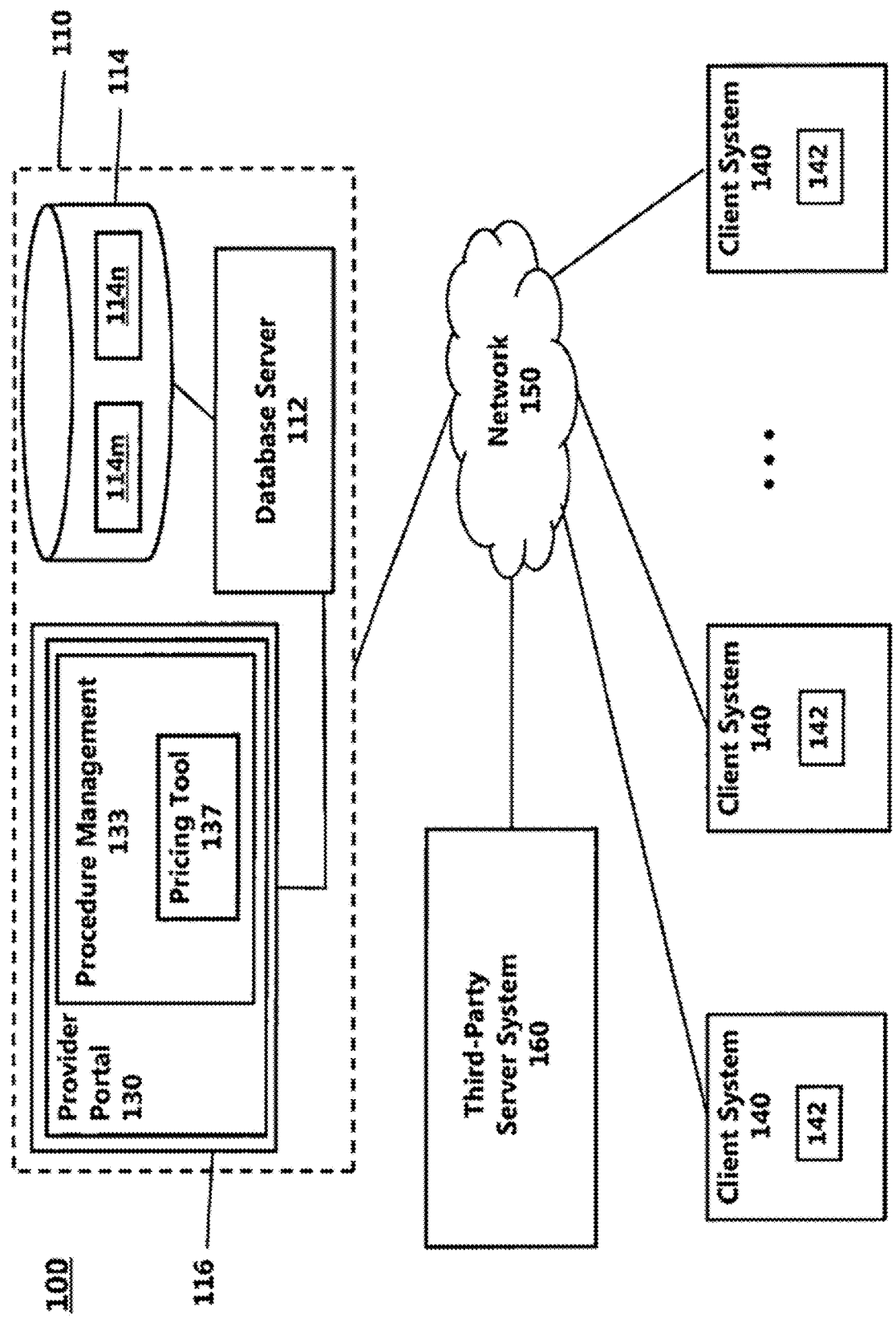
FIG. 6 is a schematic diagram illustrating a second example network architecture for a healthcare marketplace system that can be configured to implement exemplary embodiments of the present invention.

Referring now to FIG. 6, a schematic diagram illustrating an example network architecture for healthcare marketplace system 100 within which an exemplary embodiment of a provider pricing tool in accordance with the present invention is implemented. It should of course be understood that FIG. 6 is intended as an example, not as an architectural limitation for different embodiments of the present invention, and therefore, the particular elements depicted in FIG. 6 should not be considered limiting with regard to the environments within which exemplary embodiments of the present invention may be implemented.

In the example illustrated in FIG. 6, the particular components that are utilized for providing the provider pricing tool are integrated within system 100 in conjunction with the components of the system as described above with reference to the exemplary embodiments illustrated FIGS. 1 and 2. More specifically, the pricing tool 137 is shown in FIG. 6 as being implemented within procedure management service 133 included within provider portal 130, and data store 114 further comprises a service pricing information database 114*m* and a cost adjustment information database 114*n* that are maintained by database server 112, are accessed by application server 116 via database services provided at a front end by database server 112, and retain information collected from a variety of data sources that is utilized in providing the services offered via the provider pricing tool within the network service provided by the application server, as described below in greater detail.

In the present exemplary embodiments, for use in conjunction with the physician service pricing information within service pricing information database 114*m*, a corresponding set of cost adjustment data can be compiled and maintained within cost adjustment information database 114*n* that can be applied to account for geographical variances in physician costs. The cost adjustment data can, for instance, be compiled from and/or determined based upon the Geographic Practice Cost Indices (GPCIs), which is used along with RVUs in Medicare Physician Fee Schedule (PFS) provided by CMS to determine allowable payment amounts for medical procedures in a manner that reflects geographical variations in practice cost. GPCIs are used to help standardize the differences in resource costs incurred in operating a private medical practice across geographic areas when those costs are compared with the national average costs for the physician work, practice expense, and malpractice insurance components of the fee schedule.

More specifically, the CMS has established a GPCI for every Medicare payment locality for each of the three relative value unit components for a procedure (that is, the RVUs for work, practice expense, and malpractice), and the GPCIs are applied in the calculation of a fee schedule payment amount by multiplying the RVU for each component times the GPCI for that component. A listing of the current GPCI locality structure, including state, locality area (and when applicable, counties assigned to each locality area), and the corresponding GPCIs for each locality, can be obtained from the CMS website, and this information can be compiled and maintained within cost adjustment information database 114*n* by a back-end administrator of server system 110. In exemplary embodiments, a specific cost adjustment factor can be determined based on the GPCI information for each designated locality area and maintained within cost adjustment information database 114*n*. For example, a standard rate adjustment factor for each designated locality area can be determined by calculating an average (or any other suitable aggregate or composite-based) factor by which the corresponding GPCIs for the locality impact the standard national rate derived for each service. As another example, such a standard rate adjustment factor for each designated locality area can be derived directly from the Geographic Adjustment Factor (GAF) that is determined for the locality by CMS. The GAF for each designated locality area is calculated as the weighted average of the three GPCIs, where the weights are the percentage of RVUs nationally made up by the PW, PE, and MP RVUs.

In another example, for each service for which the information record within service pricing information database 114*m* includes an indication that the service is offered as a primary service of a bundled set of services along with an indication that the primary service is required to be performed at an outside facility, the respective pricing information that is included in the information record for the use of the outside facility can be determined by whether the use of the outside facility is classified as a facility outpatient service or a facility inpatient service. For instance, for each facility outpatient service, the respective pricing information that is included in the information record for the use of the outside facility can be obtained from the APC price data that is maintained in association with CPT or HCPCS procedure codes by CMS. CMS assigns individual services classified according to HCPCS codes to APCs based on similar clinical characteristics and similar costs. Thus, APCs are essentially line-level fee schedules in which each HCPCS code for a service is assigned to one of hundreds of individual APCs, and for almost every APC, the fee is determined by multiplying a prospectively established scaled relative weight for the service's clinical APC by a conversion factor (CF) to arrive at a national unadjusted payment rate for the APC.

Accordingly, in exemplary embodiments, for each service for which a respective information record is maintained within service pricing information database 114*m* and a corresponding APC is provided by CMS, the corresponding national unadjusted payment rate for the facility outpatient service can be included in the set of pricing information of the respective information record for the service within service pricing information database 114*m*.

In the present exemplary embodiment, for use in conjunction with the facility outpatient service pricing information within service pricing information database 114*m* discussed above, a corresponding set of cost adjustment data can be compiled and maintained within cost adjustment information database 114*n* that can be applied to account for geographic differences. The cost adjustment data for the facility outpatient service pricing information can, for instance, be compiled from and/or determined based upon the facility wage index that is maintained by the CMS.

In the present exemplary embodiment, for use in conjunction with the facility inpatient service pricing information within service pricing information database 114*m* discussed above, a corresponding set of cost adjustment data can be compiled and maintained within cost adjustment information database 114*n* that can be applied to account for geographic differences.

Similar to the example discussed above with regard to the cost adjustment data for the facility outpatient service pricing information, the cost adjustment data for the facility inpatient service pricing information can, for instance, be compiled from and/or determined based upon the facility wage index that is maintained by the CMS. As noted above, in exemplary embodiments, the facility wage index information can be obtained from CMS and maintained within cost adjustment information database 114*n*.

In this regard, it should be noted that certain services for which the respective information record within service pricing information database 114*m* includes an indication that the service is offered as a primary service of a bundled set of services along with an indication that the primary service is required to be performed at an outside facility may facilitate a mapping of the use of the outside facility to both facility outpatient service price data and facility inpatient service price data. In exemplary embodiments, for such services, a back-end administrator of server system 110 can make a determination of which set of facility price data is more suitable to include in the set of pricing information of the information record. For example, such a determination may be based upon whether the particular service is more typically performed as a facility outpatient service or a facility inpatient service. In alternative exemplary embodiments, for each service for which the respective information record within service pricing information database 114*m* includes an indication that the service is offered as a primary service of a bundled set of services along with an indication that the primary service is required to be performed at an outside facility for which the use of the outside facility can be mapped to both facility outpatient service price data and facility inpatient service price data, respective information records can be maintained for the service as an outpatient facility service and for the service as an inpatient facility service within service pricing information database 114*m*.

In this regard, anesthesia time is a continuous time period from the start of anesthesia to the end of an anesthesia service, and one-time unit corresponds to a 15-minute interval, or fraction thereof, starting from the time the physician begins to prepare the patient for induction and ending when the patient may safely be placed under post-operative supervision and the physician is no longer in personal attendance. The conversion factors are listed by the CMS according to locality. Thus, the conversion factor in the formula listed above will correspond to the locality of the performing provider.

In exemplary embodiments, to access the functionality provided by pricing tool 137, a provider user, upon registering a provider account with server system 110 (for example, a physician, practice group, or hospital system account) to establish an account information record within the corresponding profile database maintained within data store 114 and logging into his or her physician account, the user may be directed to a provider account page implemented by provider portal 130 that provides a set of user interface controls that can be accessed by the user to access functionality provided by procedure management service 133 to offer healthcare services for purchase by customer users registered with the system. As noted above, in the present exemplary embodiment, the accessible functionality provided by procedure management service 133 in this regard includes the functionality provided by pricing tool 137.

In particular, upon the provider user indicating an intention to utilize pricing tool in conjunction with offering healthcare services for purchase via server system 110 (for example, by selecting a "Service Pricing Tool" tab within the provider account page implemented by provider portal 130), the user will be directed to an interactive service pricing page with information that is generated based on the information maintained in the respective information record for the provider within the corresponding profile database maintained within data store 114 and the respective information records for healthcare services that are maintained in service pricing information database 114*m*. Price setting tool 137 may be configured, for example, to implement the interactive service pricing page to provide the provider user with detailed pricing information and recommended rates for services that may be offered by the provider for purchase via server system 110, as well as various user interface controls accessible by the user to perform adjustments to the recommended rates as desired.

Figure 7A:
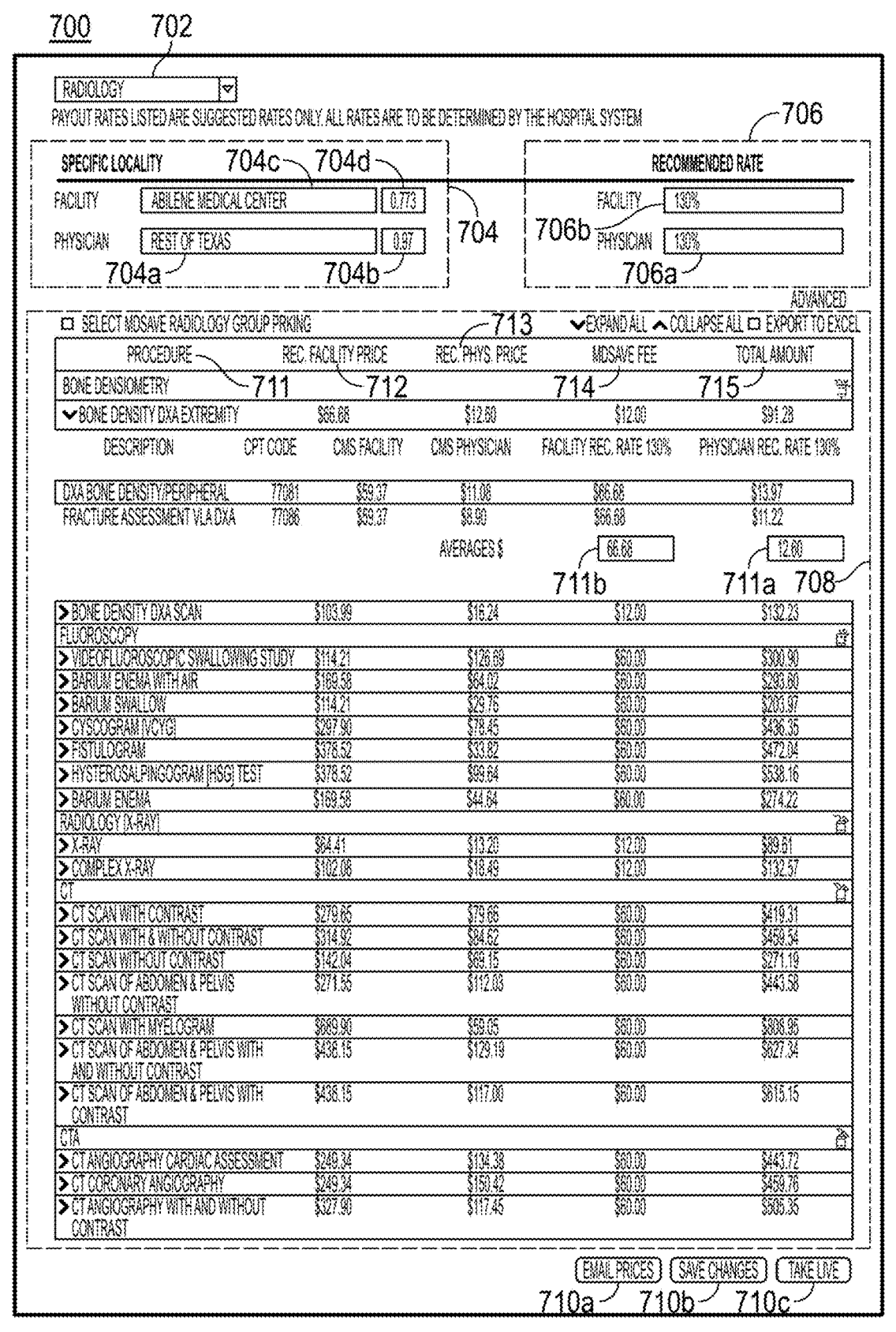

FIG. 7A is a screen shot illustrating a first example of a graphical user interface provided by such a service pricing page 700 for a user accessing provider portal 130 in association with a registered hospital system account. In the example illustrated in FIG. 7A, the user interface provided at service pricing page 700 includes a medical specialty drop-down menu 702, a locality adjustment section 704, a recommended rate adjustment section 706, a detailed pricing information section 708, and a set of selectable buttons 710*a* ("Email Prices"), 710*b* ("Save Changes"), and 710*c* ("Take Live"), the use of which will be described in greater detail below. Drop-down menu 702 provides a list of selectable medical specialties (for example, orthopedics, general surgery, cardiac imaging, etc.), and pricing tool is implemented to, in response to the user selecting a particular medical specialty using drop-down menu 702, configure the user interface options and populate the information displayed within locality adjustment section 704, recommended rate adjustment section 706, and detailed pricing information section 708 in accordance with the selected medical specialty and further based on information maintained in the respective information record for the provider that is maintained within hospital system profile database 114*d*, information that is maintained in the respective information records for each service indicated as being commonly associated with the selected medical specialty within service pricing information database 114*m*, and information maintained within cost adjustment information database 114*n*, which, as discussed above, can be accessed by pricing tool 137 via database services provided at a front end by database server 112.

For instance, in the example screen shot illustrated in FIG. 7A, the user has selected "Radiology" from medical specialty drop-down menu 702, and pricing tool 137 has, in response to this selection, configured the user interface options and populated the information displayed within locality adjustment section 704, recommended rate adjustment section 706, and detailed pricing information section 708 in accordance with the selection of "Radiology" from drop-down menu 702. More specifically, as shown in FIG. 7A, locality adjustment section 704 has been configured to include a physician locality section and a facility section in response to the selection of "Radiology" from drop-down menu 702. The physician locality section is provided for making pricing adjustments based on the locality of a physician that is affiliated with the hospital system and would be performing the radiology services being priced. The facility section is included within locality adjustment section 704 in response to pricing tool 137 recognizing that the respective information records for services indicated as being commonly associated with the selected medical specialty of radiology within service pricing information database 114m include information records having an indication that the service is a primary service of a bundled set of services that is required to be performed at an outside facility and is provided for making pricing adjustments based on the facility that is affiliated with the hospital system at which the radiology services being priced would be performed.

In the present example, the physician locality section includes a physician location field 704a and a physician location rate field 704b, and the facility section includes a facility field 704c and a facility rate field 704d. The physician location field 704a is for receiving and displaying an entry specifying the location of a physician that would be performing the services indicated as being commonly associated with the selected medical specialty of radiology within service pricing information database 114m, and the physician location rate field 704b is configured to provide a rate adjustment factor for the pricing information included in detailed pricing information section 708 for the services indicated as being commonly associated with radiology. In exemplary embodiments, pricing tool 137 can be configured to derive an initial physician location entry based on the location associated with physician affiliation(s) included in hospital system profile database 114d and include this derived physician location entry as a default value within physician location field 704a. Physician location rate field 704b is provided for receiving and displaying a geographic adjustment rate for physician services that, by default, is derived based on information maintained in cost adjustment information database 114n and provided by pricing tool 137 in correspondence with the physician location entry that is currently specified within physician location field 704a. More particularly, in exemplary embodiments, pricing tool 137 can be configured to access the physician rate cost adjustment data in cost adjustment information database 114n that corresponds to the physician location entry that is currently specified within physician location field 704a (for example, a standard rate adjustment factor determined for a designated locality area that encompasses the specified physician location entry) and derive a corresponding geographic adjustment rate that is displayed as a default value within physician location rate field 704b.

In the present example, pricing tool 137 is further configured to allow the provider user accessing service pricing page 700 to proceed to enter text corresponding to a desired location of the physician that would perform the services associated with the selected medical specialty within physician location field 704a. In this regard, pricing tool 137 may be configured to require that the text entered by the user in physician location field 704a correspond to a particular locality area for which corresponding physician rate adjustments are maintained in cost adjustment information database 114n.

The list of suggested physician locations provided by pricing tool 137 can further include an option for the user to select a standard, national physician rate rather than a particular geographic location. In response to a specification of a new physician location within physician location field 704a, pricing tool 137 can be configured to dynamically access the physician rate cost adjustment data in cost adjustment information database 114n that corresponds to the newly-specified physician location entry that is currently specified within physician location field 704a and derive a corresponding geographic adjustment rate that is displayed as the current value within physician location rate field 704b.

In exemplary embodiments, pricing tool 137 can be configured to derive an initial outside facility entry based on the facility affiliation(s) included the respective information record for the hospital system account in hospital system profile database 114d being used to access the pricing tool 137 functionality via provider portal 130 and include this derived facility entry as a default value within facility field 704c. Facility rate field 704d is provided for receiving and displaying an adjustment rate for facility services that, by default, is derived and provided by pricing tool 137 in correspondence with the characteristics of the facility that is currently specified as the entry within facility field 704c.

In the present example, pricing tool 137 is further configured to allow the provider user accessing service pricing page 700 to proceed to enter text corresponding to a name of a desired outside facility at which the services associated with the selected medical specialty would be performed within facility field 704c. In this regard, pricing tool 137 may be configured to require that the text entered by the user in facility field 704c correspond to the name of a particular facility specified in the facility affiliations included the respective information record for the hospital system account in hospital system profile database 114d being used to access the pricing tool 137 functionality via provider portal 130.

With continued reference to the example screen shot illustrated in FIG. 7A, pricing tool 137 has, in response to the user selection "Radiology" from medical specialty drop-down menu 702, configured the user interface options and populated the information displayed within rate adjustment section 706. More specifically, as shown in FIG. 7A, rate adjustment section 706 has been configured to include a physician rate adjustment field 706a and a facility rate adjustment field 706b in response to the selection of "Radiology" from drop-down menu 702. Physician rate adjustment field 706a is provided for making a general pricing adjustment to the pricing information included in detailed pricing information section 708 for physician fees for the services indicated as being commonly associated with radiology as desired by the provider user that may be based on any budgetary considerations specific to the provider and/or physician.

With continued reference to the example screen shot illustrated in FIG. 7A, as noted above, pricing tool 137 has, in response to the user selection "Radiology" from medical specialty drop-down menu 702, configured the user interface options and populated the information displayed within detailed pricing information section 708. In general, as shown in FIG. 7A, detailed pricing information section 708 is generated by pricing tool 137 as a table with various interactive user interface controls that includes a procedure column 711, a facility price column 712, a physician price column 713, an additional fee column 714, and a total amount column 715.

The information in procedure column 711 is generated by pricing tool 137 to include a row entry for each procedure category listed in the respective information records for services that are maintained in service pricing information database 114m and include an indication that the service is commonly associated with the medical specialty selected via drop-down menu 702, which is "Radiology" for the example screen shot depicted in FIG. 7A. For instance, the procedure categories listed in procedure column 711 in the present example include "Bone Density DXA Extremity" radiology procedures, "Bone Density DXA Scan" radiology procedures, and "Videofluoroscopic Swallowing Study" radiology procedures. As further illustrated in FIG. 7A for the example of the "Bone Density DXA Extremity" radiology procedures listing in in procedure column 711, detailed pricing information section 708 is implemented to include user interface elements that are accessible by the user.

In the present example, the expanded information for the "Bone Density DXA Extremity" radiology procedures listing includes row entries for a "Dxa bone density/peripheral" service and a "Fracture assessment via dxa" service. As further illustrated in FIG. 7A, the expanded information for a particular procedure category further includes, for each service categorized as a sub-procedure of the procedure category, a medical code number used to identify the service (for example, a CPT code), a base facility rate, a base physician rate, an adjusted facility rate, and an adjusted physician rate. The base physician rate for each service listed in the expanded display is obtained by pricing tool 137 from standard national physician rate derived for the service and the adjusted physician rate for each service listed in the expanded display is calculated by pricing tool 137 for display within detailed pricing information section 708 by multiplying the corresponding base physician rate by both the current value that is specified in physician location rate field 704b of locality adjustment section 704 and the current percentage value that is specified in physician rate adjustment field 706a of recommended rate adjustment section 706.

In the present example, as further illustrated in FIG. 7A, the expanded information for a particular procedure category further includes a physician price field 711a that specifies a price that will be set by the provider user for each of the services that have been categorized under the expanded procedure category and a facility price field 711b that specifies a price that will be applied by the provider user for the use of an outside facility for each of the services that have been categorized under the expanded procedure category.

In exemplary embodiments, pricing tool 137 can be configured to derive and include initial, default price values within physician price field 711a and physician price field 71l a. As further indicated in the example screen shot illustrated in FIG. 7A, the row entry for a particular procedure category will include a pricing value under physician price column 713 that corresponds to the pricing value that is specified within physician price field 711a in the expanded display for the procedure category, and, likewise, the row entry for a particular procedure category will include a pricing value under facility price column 712 that corresponds to the pricing value that is specified within facility price field 711b in the expanded display for the procedure category. In this regard, pricing tool 137 can be configured to dynamically update the pricing values provided under physician price column 713 and facility price column 712 in response to changes to the price values within physician price field 711a and facility price field 711b, respectively. As further illustrated in FIG. 7A, the row entry for a particular procedure category can include a pricing value under total amount column 715 that is provided as a sum of the price values listed under facility price column 712, physician price column 713, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130.

As noted above and further illustrated in FIG. 7A, the user interface provided at service pricing page 700 in the present example also includes a set of accessible user interface controls 710a ("Email Prices"), 710b ("Save Changes"), and 710c ("Take Live"). For purposes of the present example, these user interface controls are provided within service pricing page 700 as selectable buttons. In the present exemplary embodiment, pricing tool 137 can be configured to, in response to a provider user selecting "Save Changes" button 710b, generate an information record that includes indications of all of the information.

In the present exemplary embodiment, pricing tool 137 can be configured to, in response to a provider user selecting "Email Prices" button 710a, provide user interface controls for allowing the user to specify an email address and send an electronic document that includes indications of the pricing information.

Finally, with reference to the present example, pricing tool 137 can be configured to, in response to a provider user selecting "Take Live" button 710c, automatically initiate, on behalf of the provider user, a service offering with procedure management service 133 to offer each of the services currently included within detailed pricing information section 708 of service pricing page 700 for the particular medical specialty presented selected by the user from drop-down menu 702 for purchase via server system 110. In this manner, pricing tool 137 can provide a mechanism for a provider to offer a large number of services for purchase via marketplace system 100 by customer users registered with the system without having to perform full set of operations described above for accessing functionality provided by procedure management service 133 to offer each of the services individually.

Figure 7B:
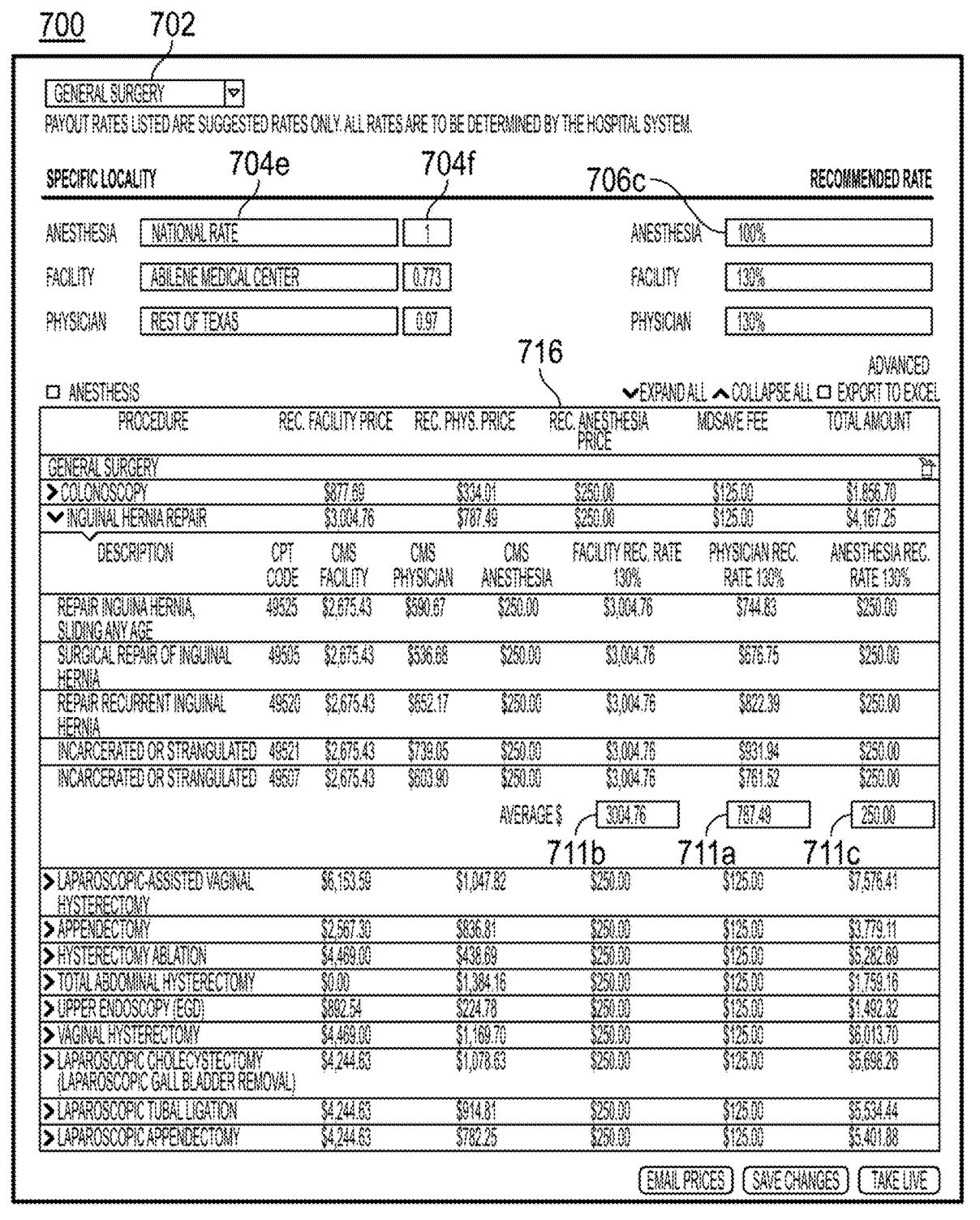

FIG. 7B is a screen shot illustrating a second example of a graphical user interface provided by service pricing page 700 for a user accessing provider portal 130 in association with a registered hospital system account. In the example illustrated in FIG. 7B, the user has selected "General Surgery" from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "General Surgery" from drop-down menu 702. More specifically, as shown in FIG. 7B, locality adjustment section 704 has been configured to include, in addition to the physician locality section and the facility section described above with reference to the example illustrated in FIG. 7C, an anesthesia locality section in response to the selection of "General Surgery" from drop-down menu 702. The anesthesia locality section is included within locality adjustment section 704 in response to pricing tool 137 recognizing that the respective information records for services.

In the present example, the anesthesia locality section includes an anesthesia location field 704e and an anesthesia location rate field 704f. The anesthesia location field 704e is for receiving and displaying an entry specifying the location at which the services indicated as being commonly associated with the selected medical specialty of general surgery within service pricing information database 114m would be performed, and the anesthesia location rate field 704f is configured to provide a rate adjustment factor for the pricing information included in detailed pricing information section 708 for the services indicated as being commonly associated with radiology.

Anesthesia location rate field 704f is provided for receiving and displaying a geographic adjustment rate for physician services that, by default, is derived and provided by pricing tool 137 in correspondence with the anesthesia location entry that is currently specified within anesthesia location field 704e. More particularly, in exemplary embodiments, pricing tool 137 can be configured to access the information pertaining to anesthesia rate adjustments in service pricing information database 114n corresponding to the anesthesia location entry that is currently specified within anesthesia location field 704e and derive a corresponding geographic adjustment rate that is displayed as a default value within anesthesia location rate field 704e. The corresponding geographic adjustment rate can be derived, for example, based on a ratio of the CMS anesthesia conversion factor to a standard, national anesthesia conversion factor.

Specification of a new location within anesthesia location field 704e, pricing tool 137 can be configured to dynamically access the information pertaining to physician rate adjustments in geographic factors database 114n corresponding to the newly-specified physician location entry within anesthesia location field 704e and derive a corresponding geographic adjustment rate that is displayed as the current value within anesthesia location rate field 704f. In the present example, pricing tool 137 is also configured to allow the provider user to directly access anesthesia location rate field 704f and specify a desired value for the geographic adjustment rate that will override the particular geographic adjustment rate that is derived by pricing tool 137 based on the location entry within anesthesia location field 704e and displayed as the current value within anesthesia location rate field 704f. The effect of such an entry being submitted within anesthesia rate field 704f will be described below with reference to detailed pricing information section 708.

With continued reference to the example screen shot illustrated in FIG. 7B, as noted above, pricing tool 137 has, in response to the user selection "General Surgery" from medical specialty drop-down menu 702, configured the user interface options and populated the information displayed within rate adjustment section 706.

With continued reference to the example screen shot illustrated in FIG. 7B, as noted above, pricing tool 137 has, in response to the user selection "General Surgery" from medical specialty drop-down menu 702, configured the user interface options and populated the information displayed within detailed pricing information section 708. In general, as shown in FIG. 7B, detailed pricing information section 708 is generated by pricing tool 137 as a table with various interactive user interface controls that includes, in addition to procedure column 711, facility price column 712, physician price column 713, additional fee column 714, and total amount column 715, an anesthesia price column 716. As illustrated in FIG. 7B, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base anesthesia rate and an adjusted anesthesia rate.

In the present example, as further illustrated in FIG. 7B, the expanded information for a particular procedure category further includes, in addition to physician price field 711a and facility price field 711b, an anesthesia price field 711c that specifies a price that will be applied by the provider user for each anesthesia service performed in association with the services that have been categorized under the expanded procedure category.

For example, pricing tool 137 can be configured to enable the user select between using the average of the corresponding adjusted anesthesia rates for all services listed in the expanded display for a procedure category for the price values within anesthesia price field 711c or the highest of the corresponding adjusted anesthesia rates for all services listed in the expanded display for a procedure category for the price values within anesthesia price field 711c. In exemplary embodiments, pricing tool 137 can be further configured to allow the provider user accessing service pricing page 700 to access anesthesia price field 711c to input a particular price value within this field.

As further indicated in the example screen shot illustrated in FIG. 7B, the row entry for a particular procedure category will include a pricing value under anesthesia price column 716 that corresponds to the pricing value that is specified within anesthesia price field 711c in the expanded display for the procedure category. In this regard, pricing tool 137 can be configured to dynamically update the pricing value provided under anesthesia price column 716 in response to changes to the price value within anesthesia price field 711c. As discussed above, in exemplary configurations of pricing tool 137, such changes to the price value within anesthesia price field 711c in the expanded display for a particular procedure category may occur in response to changes to any of the current value that is specified in anesthesia location rate field 704f of locality adjustment section 704, the current percentage value that is specified in anesthesia rate adjustment field 706c of recommended rate adjustment section 706, changes in the particular method employed by pricing tool 137 to derive and set the price value within anesthesia price field 711c, and direct entries of a particular price value by a provider user within anesthesia price field 711c.

As further illustrated in FIG. 7B, the row entry for a particular procedure category can include a pricing value under total amount column 715 that is provided as a sum of the price values listed under facility price column 712, physician price column 713, anesthesia price column 716, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130. In exemplary embodiments, pricing tool 137 can be further configured to provide an option via user interface controls implemented within service pricing page 700 for a provider user that is accessing the service pricing page 700 and has selected a medical specialty from drop-down menu 702 for which pricing tool 137 recognizes that the respective information records for services indicated as being commonly associated with the selected medical specialty within service pricing information database 114m include information records having an indication that the service is a primary service of a bundled set of services that a secondary service associated with the primary service in the bundled set is an anesthesia procedure to not include information and options pertaining to the associated anesthesia procedures and anesthesia pricing information within the service pricing page for the selected medical specialty.

FIG. 7C is a screen shot illustrating a third example of a graphical user interface provided by service pricing page 700 for a user accessing provider portal 130 in association with a registered hospital system account. In the example illustrated in FIG. 7C, the user has selected "GI" (gastroenterology) from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "GI" from drop-down menu 702.

In general, as shown in FIG. 7C, detailed pricing information section 708 is generated by pricing tool 137 as a table with various interactive user interface controls that includes, in addition to procedure column 711, facility price column 712, physician price column 713, additional fee column 714, and total amount column 715, a pathology price column 717.

As illustrated in FIG. 7C, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base pathology rate. The base pathology rate for each service listed in the expanded display is obtained by pricing tool 137 from the pathology rate for the service that is stored within the respective information record maintained for the service within service pricing information database 114m for display within detailed pricing information section 708.

In the present example, as further illustrated in FIG. 7C, the expanded information for a particular procedure category further includes, in addition to physician price field 711a and facility price field 711b, a pathology price field 711d that specifies a price that will be applied by the provider user for each pathology service performed in association with the services that have been categorized under the expanded procedure category. In exemplary embodiments, pricing tool 137 can be configured to derive and include an initial, default price value within pathology price field 711d. For example, pricing tool 137 can derive and set the default price value within pathology price field 711d as the average of the base pathology rates for all services listed in the expanded display for a procedure category. In exemplary embodiments, pricing tool 137 can be further configured to allow the provider user accessing service pricing page 700 to access pathology price field 711d to input a particular price value within this field.

As further indicated in the example screen shot illustrated in FIG. 7C, the row entry for a particular procedure category will include a pricing value under pathology price column 717 that corresponds to the pricing value that is specified within pathology price field 711d in the expanded display for the procedure category. In this regard, pricing tool 137 can be configured to dynamically update the pricing value provided under pathology price column 717 in response to changes to the price value within pathology price field 711d. As further illustrated in FIG. 7B, the row entry for a particular procedure category can include a pricing value under total amount column 715 that is provided as a sum of the price values listed under facility price column 712, physician price column 713, pathology price column 717, and, if included, additional fee column 714 and anesthesia price column 716 in the row entry for a particular procedure category. This represents the actual price at which each service listed in the expanded display for a procedure category would be offered for purchase as a bundled set of services via marketplace system 100 from the provider user accessing service pricing page 700 via provider portal 130.

In exemplary embodiments, the functionality that is provided within provider portal 130 for users of hospital system accounts can further include a set of user interface controls implemented by service selling service 135 that can be accessed by a user of a hospital system account to sell prepaid purchases of services to a customer in-person by operating a client system located at, for example, a medical clinic being visited by the customer to access application server 116. In this regard, service selling service 135 may provide functionality allowing a user of a hospital system account to sell, in addition to services that are offered for purchase by the hospital within server system 100, services that are constructed by a user of a hospital system account, including bundled sets of services.

In exemplary embodiments, the user interface implemented by account management service 131 may be further configured to provide user interface controls for requesting authorization for payment of a predetermined fee to gain access to the ability to offer healthcare products for purchase within marketplace system 100. Such a fee may be, for example, a one-time charge or a periodic charge (such as a monthly, biannual, or annual fee).

Upon the user indicating an intention to offer a healthcare product for purchase (for example, by selecting a "Offer Service" tab within the pharmacy account page implemented by provider portal 130), the user will be able to initiate a product offering with product management service 134 to offer a healthcare product for purchase via server system 110.

Upon the user indicating an intention within the pharmacy account page implemented by provider portal 130 to access various account management functions, the pharmacy administrator can access various user interface elements provided by account management service 131 to, for example, manage pharmacy and payment or compensation information, manage information pertaining to products offered for purchase by the pharmacy, and view a history of transactions performed for products offered for purchase by the pharmacy within server system 110.

In exemplary embodiments disclosed herein, because certain healthcare information may be considered highly confidential, marketplace system 100 can be implemented to provide for a high-level of security for information transferred between client applications executing on client systems 142 and application server 116. For illustration, whenever applicable, marketplace system 100 (for example, for operations and functionalities) may be implemented to comply with requirements under the Health Insurance Portability and Accountability Act (HIPAA). For example, if certain type of information should not be accessible to a specific party (for example, a prescription product manufacturer or service provider) according to HIPAA requirements or other confidentiality concerns, system 100 can implement information-control or information-protection measures that ensure the specific party cannot access that type of information. As another example, to protect patient privacy, information transmitted over a computer or communication network, such as information transmitted between application server 116 and any client system 140 and electronic messages transmitted by server system 110, can be encrypted. In exemplary embodiments, system 100 can be HIPAA-validated to ensure privacy and comply with all requirements.

Figure 8:
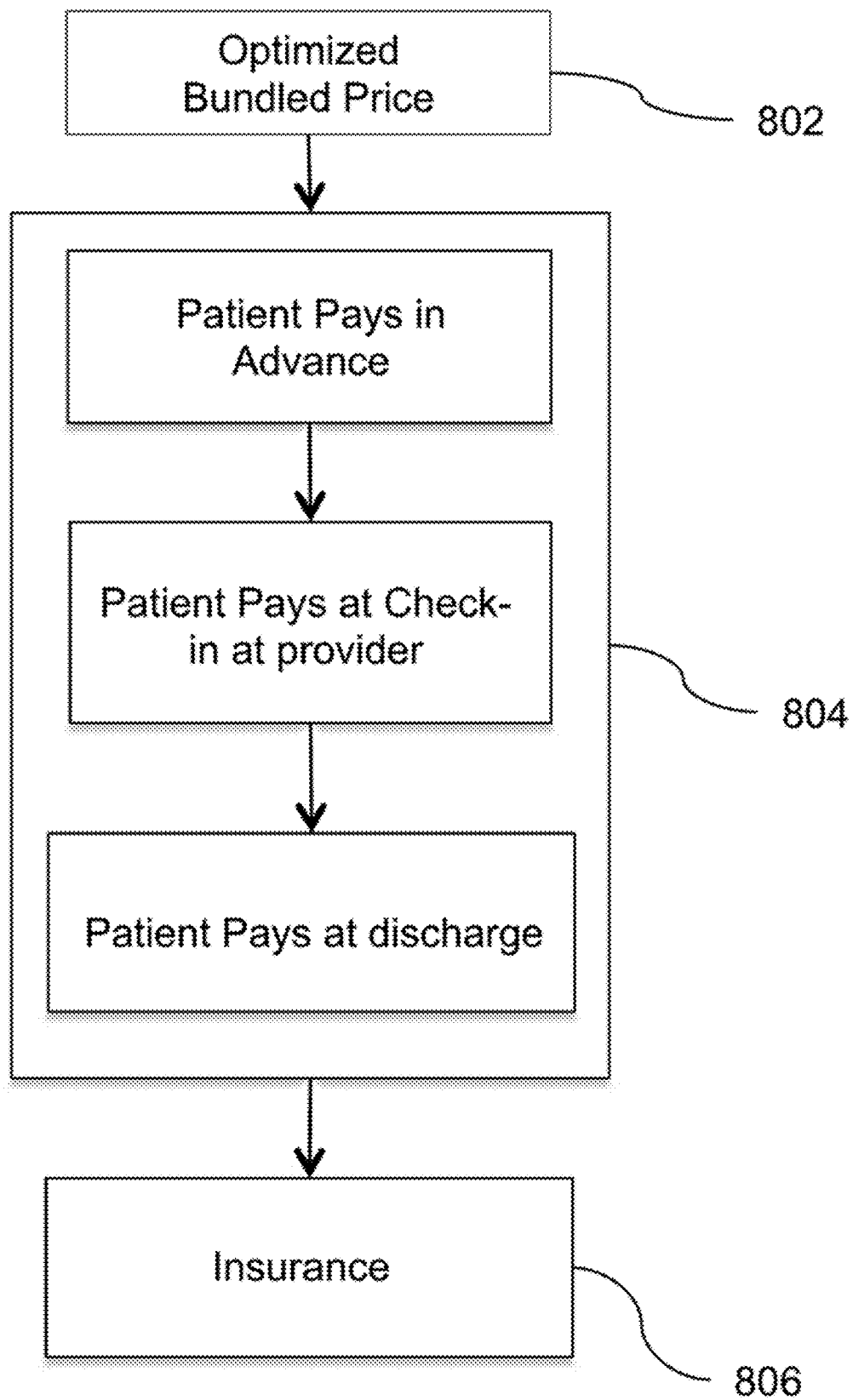
FIG. 8 illustrates a flow chart of an insurance policy stored in the insurance database executed by the application server in accordance with exemplary embodiments of the present invention.

FIG. 8 illustrates a flow chart of an insurance policy stored in the insurance database (114o, shown in FIG. 2) executed by the application server (116, shown in FIG. 2). The insurance database is programmed to provide an optimized bundled price 802 for healthcare services. For exemplary purposes, the system maximizes collections at each phase in the user's care cycle. For various phases there is an option for paying the payment 804. The patient is referred or scheduled for a procedure, where the patient may receive a push notification to pay prospectively. Alternatively, the patient checks-in at a provider's location and the patient pays at the point of service such as by cash, card, digital wallet, etc. Alternatively, the patient is made to pay after services are provided and/or at discharge wherein, the patient receives a push notification to pay retrospectively.

Further, each of the patient's information is monitored such as but not limited to a doctor's order/schedule (for example, CHC Redox), propensity to pay data (CHC-Vendor), benefit status (CHC-ribbon health) and CareCredit pre-approval. Based on the patient information, a doctor's order is matched. Further, the price is set based on the patient's capacity and/or willingness to pay for the service and/or product. Further, each payment is monitored to check if a patient is paying out-of-pocket. The system compares the bundled price to the remaining patient deductible to determine the patient's capacity to pay for the services and/or product. Furthermore, patients are allowed to pay either in full or through CareCredit.

The system is configured to pay the optimal price in full every time to the hospital/physician/pharmacy and any associated service provider. The procedure is transparent and acceptable to both patients and the provider. The service providers collect the maximum data on the patients who are willing to pay. Further, the hospital may leave revenue on the table by charging less than what patients are willing to pay.

The application server (116, shown in FIG. 2) processes the data stored in the insurance database 114o and allows the user to access the insurance information via an insurance management service (14, shown in FIG. 2). The hospital sends an electronic claim to the system after care is delivered to the patient. The system then distributes payment and sends an electronic remittance file based on the information stored in the insurance database 114o. The system passes the electronic claim to the insurance company 806 to update the patient's accumulator (not for reimbursement). The insurance 806 then notifies the system of accumulator status. The system then sends an update to the patients.

Figure 9:
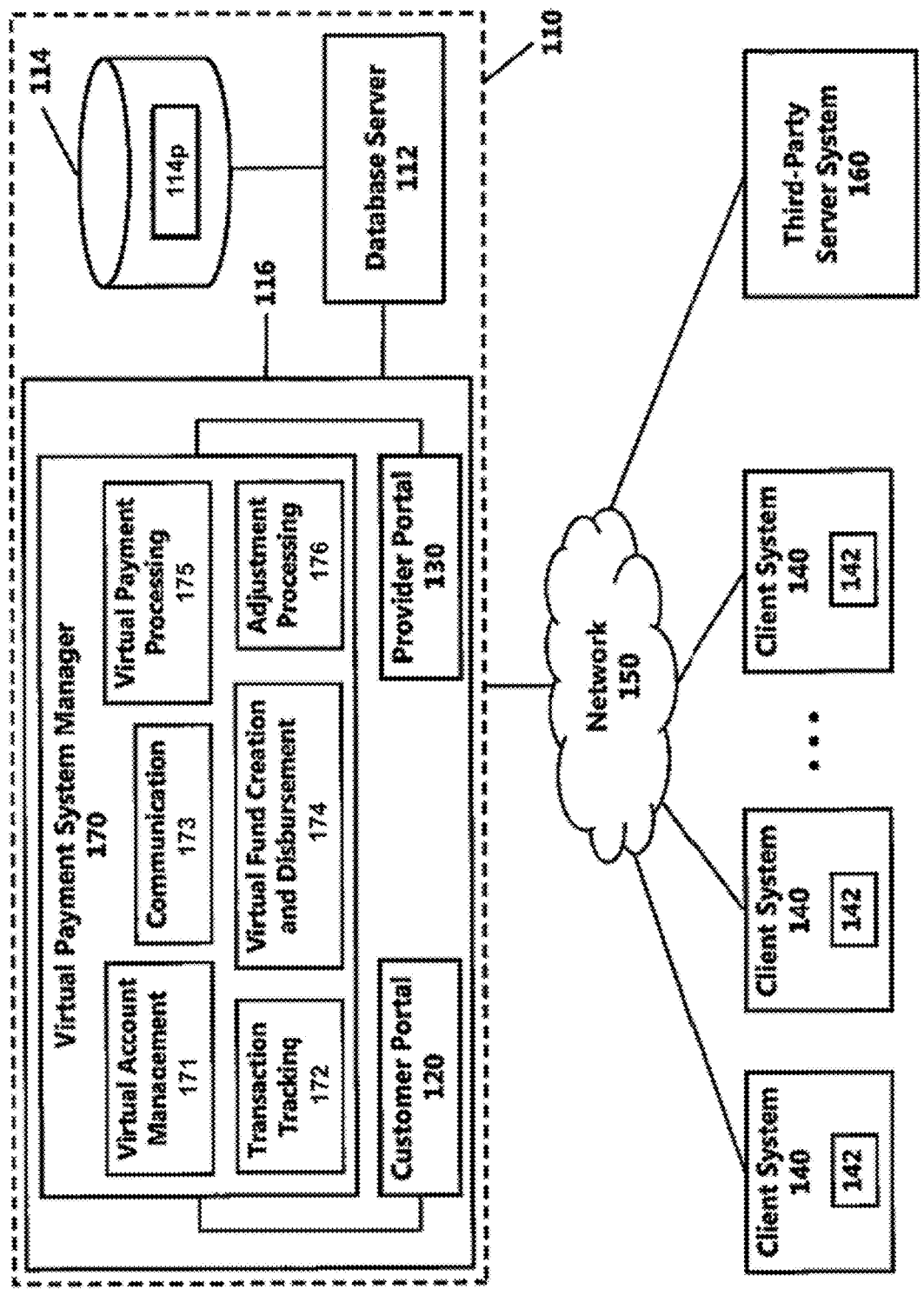
FIG. 9 illustrates a block diagram of a virtual payment system manager communicating with client system in a healthcare marketplace system.

FIG. 9 illustrates a block diagram of a virtual payment system manager 170 communicating with a client system in a healthcare marketplace system in accordance with another exemplary embodiment of the present invention. As noted above, exemplary embodiments of the present invention may be implemented to provide a virtual payment system for facilitating and accounting for the exchange of payment for services and products purchased by (or otherwise purchased on behalf of) patients and offered by healthcare providers via the creation, transfer, and redemption of virtual funds within a central server system 110.

In some exemplary embodiments, the virtual payment system manager 170 is configured to facilitate the tracking and management of promotional credits that may be offered by the providers of a healthcare marketplace system 100 to registered users of the server system 110 for taking certain actions within the system in association with their registered accounts.

For example, the providers of a marketplace system 100 may offer a promotion to potential customer users in which each user, upon completing registration of a respective customer account with server system 110, will receive a credit of a specified amount of funds (for instance, a credit of $25) that the customer user may use to purchase services and/or products offered within marketplace system 100 by provider users that are registered with server system 110.

In one embodiment, the virtual payment system manager 170 is configured to, access the database server 112 to create the respective account information record for the virtual money account for the customer within the virtual money account database 114o, and access database server 112 to create a new virtual fund corresponding to a specified amount for a promotional credit within the database of virtual fund objects included in the respective account information record.

In this regard, the virtual payment system manager 170 generates a unique identifier for the new virtual fund object being created and defines the attributes of the object to include an indication of the value of the corresponding virtual funds, the unique identifier generated for the object, an indication that the original funding source is a credit that was conveyed by the providers of marketplace system 100, a creation timestamp for the object, an indication that the corresponding virtual funds for the object are not presently allocated to use as payment for an offered service or product purchased within the marketplace system, and, optionally, an indication of an expiration date for the promotional credit by which the customer user must use the credited funds to purchase the services and/or products offered within marketplace system 100.

In such an example, the virtual payment system manager 170 is configured to further access database server 112 to also create a corresponding new virtual fund object for the promotional credit within the container of virtual fund objects included in the respective account information record for a respective virtual money account that is being maintained within virtual money account database 114o for an entity that provides the marketplace system (which may have already been established, for example, by a backend administrator of server system 110). More specifically, virtual payment system manager 170 generates a unique identifier for the new virtual fund object being created and define the attributes of the object to include an indication of the value of the corresponding virtual funds as a negative value, the unique identifier generated for the object, an indication that the original funding source is a corresponding amount of real currency held within an external financial account maintained by the providers of marketplace system 100 (and thereby owed to the virtual payment system by the marketplace system providers), and a creation timestamp for the object.

In one embodiment the virtual payment system manager 170 is also configured to, upon creating the corresponding virtual fund objects for the promotional credit within the respective account information records for the virtual money accounts for the customer user and the entity that provides the marketplace system within virtual money account database 114o, updates the total balance values and available balance values included in the sets of general information within the respective account information records for the respective virtual money accounts appropriately to reflect the newly-created virtual fund objects.

In the example illustrated in FIG. 9, the particular components that are utilized for providing the virtual payment system are integrated within system 100 in conjunction with the components of the system as described above and herein below with reference to the exemplary embodiments illustrated FIGS. 1 and 2. In particular, as depicted in FIG. 9, application server 116 is further implemented to include virtual payment system manager 170. As also depicted in FIG. 9, data store 114 further comprises virtual money account database 114*p*, which is maintained by database server 112, is accessed by application server 116.

In the present exemplary embodiment, virtual payment system manager 170 is shown in FIG. 9 as including a virtual account management module 171, a transaction tracking module 172, a communication module 173, a virtual fund creation and disbursement module 174, a virtual payment processing module 175, and an adjustment processing module 176. In general, the various modules implemented within virtual payment system manager 170 in the present exemplary embodiments are configured to interact with one another, customer portal 120, provider portal 130, and data store 114 via database server 112 to perform the various operations described in the examples provided above pertaining to exemplary embodiments in which a virtual payment system is implemented within server system 110.

The virtual account management module 171 is configured to access virtual money account database 114*p* to create respective account information records for respective virtual money accounts of participants to transactions conducted within marketplace system 100. The virtual account management module 171 retrieves, maintains, performs modifications to respective information account records as necessary in response to participants that are logged-in to server system 110 accessing the account management functions provided by account management service 122 or account management service 131 to manage and view information pertaining to the respective virtual money accounts for the participants within the virtual payment system.

Transaction tracking module 172 can, for example, be configured to dynamically perform updates to the accounting details pertaining to transactions conducted within the virtual payment system. The module 172 dynamically calculates and performs updates to the balance values that are included within the general information in the respective account information records for the respective virtual money accounts in response to transactions conducted within the virtual payment system.

Further, module 172 dynamically performs processing for handling virtual fund objects that have been created within the virtual money account based on promotional credits that have expired in response to such expirations occurring, and dynamically perform processing for reversing payment processing operations performed within the virtual payment system for purchases of offered services and products that have not been redeemed within expiration periods specified for such purchases in response to the end of such expiration periods being reached Communication module 173 can, for example, be configured to generate notifications and reports with respect to virtual money accounts managed and transactions conducted within the virtual payment system, transmit generated notifications and reports to corresponding components of customer portal 120 and provider portal 130, receive notifications and information from corresponding components of customer portal 120 and provider portal 130, and process such received notifications and information.

Virtual fund creation and disbursement module 174 can, for example, be configured to implement functionality for creating or instantiating new virtual fund objects within respective account information records for virtual money accounts as needed for transactions conducted within the virtual payment system, processing disbursal requests within the virtual payment system (including functionality for deleting virtual fund objects), and performing automatic periodic disbursals for virtual money accounts within the virtual payment system.

Virtual payment processing module 175 can, for example, be configured to implement functionality for performing operations for facilitating payment processing within the virtual payment system for purchases of offered services and products by customers users registered with server system 110, as well as to perform corresponding updates to the attributes defining the virtual fund objects within the respective account information records in response to performing such operations for facilitating payment processing within the virtual payment system. Adjustment processing module 176 can, for example, be configured to implement functionality for performing operations for processing cancellation requests, refund requests, and other modifications to purchases of offered services and products for which payment processing is handled within the virtual payment system, as well as to perform corresponding updates to the attributes defining the virtual fund objects within the respective account information records in response to performing such operations for processing cancellation requests, refund requests, and other modifications to purchases within the virtual payment system.

In exemplary embodiments disclosed herein, because certain healthcare information may be considered highly confidential, marketplace system 100 can be implemented to provide for a high-level of security for information transferred between client applications executing on client systems 142 and application server 116. For illustration, whenever applicable, marketplace system 100 (for example, for operations and functionalities) may be implemented to comply with requirements under the Health Insurance Portability and Accountability Act (HIPAA). As another example, to protect patient privacy, information transmitted over a computer or communication network, such as information transmitted between application server 116 and any client system 140 and electronic messages transmitted by server system 110, can be encrypted. In exemplary embodiments, system 100 can be HIPAA-validated to ensure privacy and comply with all requirements.

Figure 10:
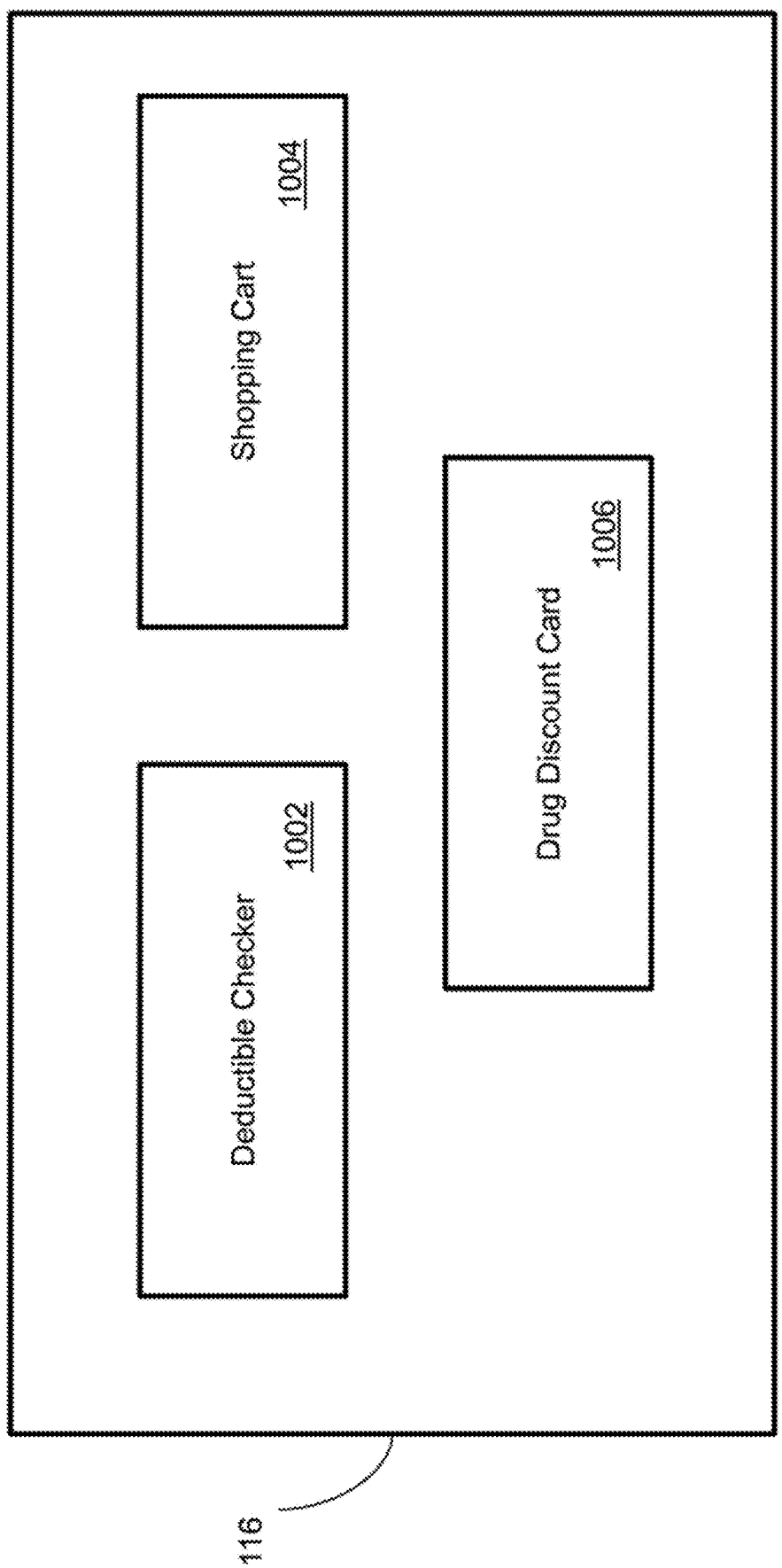
FIG. 10 illustrates a block diagram of the application server showing deductible checker, shopping cart, and drug discounted card in accordance with another embodiment of the present invention.

FIG. 10 illustrates a block diagram of the application server showing a deductible checker, shopping cart and drug discount card in accordance with another embodiment of the present invention. The application server 116 may further include a deductible checker 1002 to look up the patient's deductible, a shopping cart 1004 for providing details of pricing to the user, and a drug discount card 1006 for the user for subscription of healthcare services.

The deductible checker 1002 allows patient's/user's to look up their deductible and to let the user know whether the healthcare service offered is at better and/or competitive prices. The shopping cart 1004 is automatically communicated to the registered users with the pricing details of the healthcare services with which they intend to proceed. The shopping cart 1004 is automatically communicated such as but not limited to email, SMS, flashing on the graphical user interface, and any other similar communication networks etc. The shopping cart 1004 automatically checks for any deductibles, insurance and accordingly generates the pricing for the user.

In another embodiment, the shopping cart 1004 is verified by an analyst to confirm the pricing. Thus, the shopping cart is sent to the analyst system and then to the user. This allows the user to pre-pay for the healthcare services. Further, the shopping cart 1004 is generated with the right bundled prices (e.g. accounting for discounts when certain procedures are purchased together etc.). The drug discount card 1006 is provided to the users who subscribe to the healthcare services.

Figure 11:
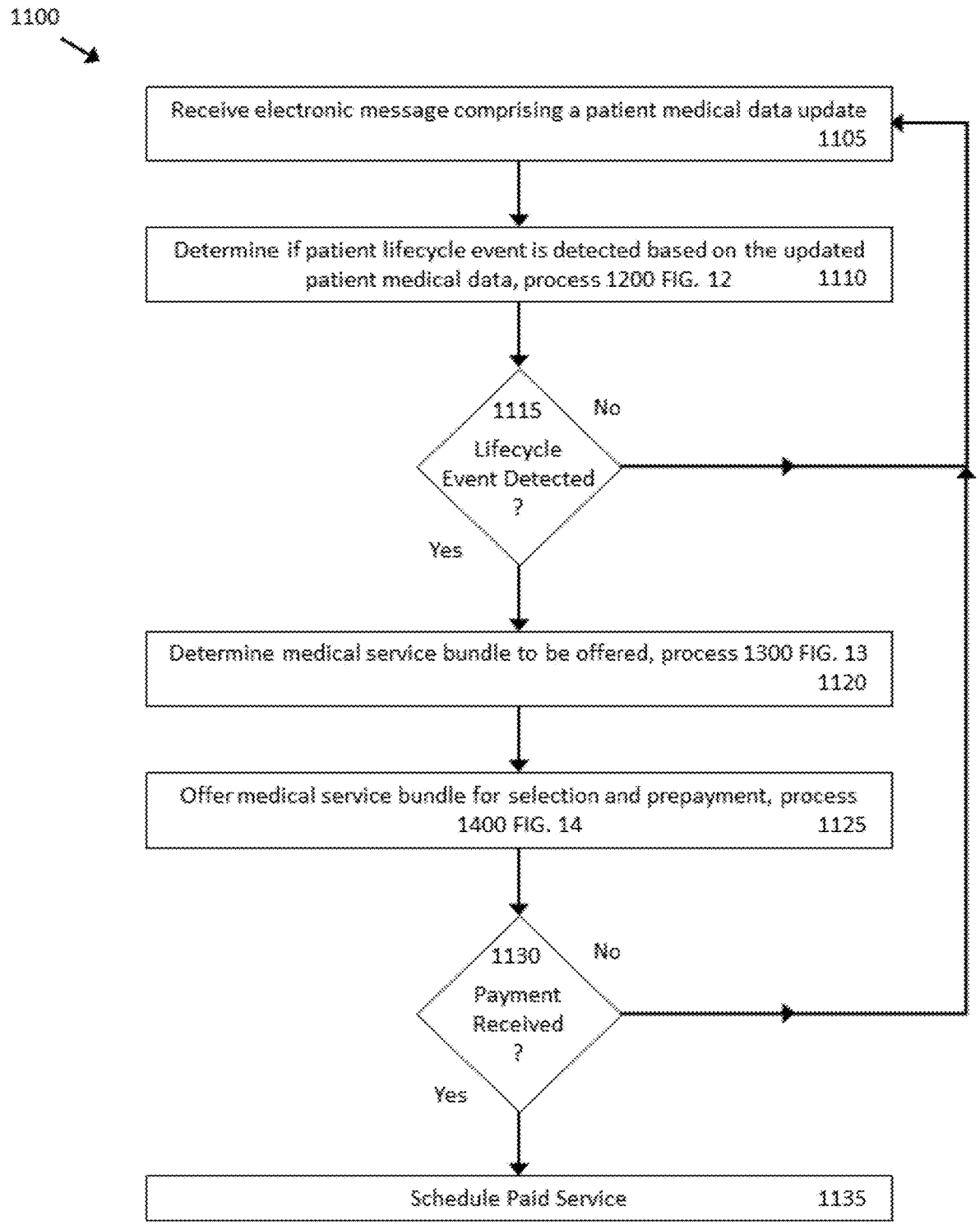
FIG. 11 is a process flow illustrative of an example aspect of patient lifecycle event triggered shopping cart provisioning design.

FIG. 11 is a process flow illustrative of an example aspect of patient lifecycle event triggered shopping cart provisioning design. The method depicted in FIG. 11 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1100 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 11 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604.

The depicted method 1100 begins at step 1105 with the processor 604 receiving an electronic message comprising a patient medical data update. The electronic message may include an EIR (Electronic Health Record). The EHR may include updated patient medical data. The patient medical data may be updated relative to historical patient medical data. The processor 604 may access and store the patient medical data using the customer profile database 114*a*, depicted in FIG. 2.

Then, the method continues at step 1110 with the processor 604 determining if a patient lifecycle event is detected based on the updated patient medical data. The processor 604 executes the process 1200, depicted by FIG. 12 and described herein, to determine if a patient lifecycle event is detected. The processor 604 may determine if a patient lifecycle event is detected based on accessing and storing patient, practice, or condition data using, for example, any of customer profile database 114*a*, practice group profile database 114*c*, or condition information database 114*f*, depicted in FIG. 2.

Then, the method continues at step 1115 with the processor 604 performing a test to determine if a patient lifecycle event is detected, based on the execution of process 1200 by the processor 604 at step 1110. Upon a determination by the processor 604 at step 1115 that a patient lifecycle event has not been detected, the method continues at step 1105 with the processor 604 receiving an electronic message comprising a patient medical data update.

Figure 13:
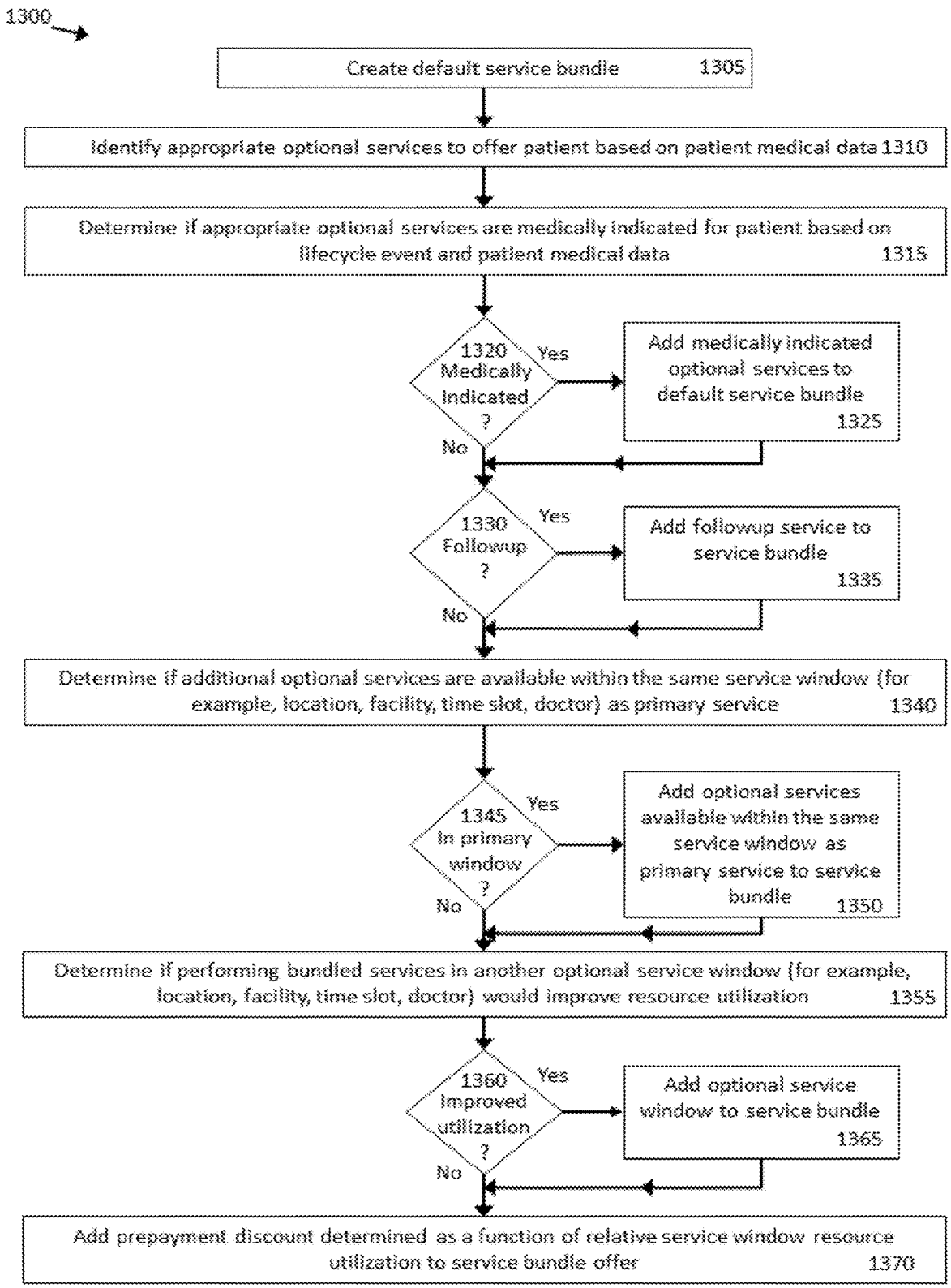
FIG. 13 is a process flow illustrative of an example aspect of patient lifecycle event triggered shopping cart provisioning design.

Upon a determination by the processor 604 at step 1115 that a patient lifecycle event has been detected, the method continues at step 1120 with the processor 604 executing the process 1300, depicted by FIG. 13 and described herein, to determine a medical service bundle to be offered. The processor 604 may determine the medical service bundle based on accessing and storing medical service data using any of customer profile database 114*a*, physician profile database 114*b*, practice group profile database 114*c*, condition information database 114*f*, or available service database 114*g*, depicted in FIG. 2.

Figure 14:
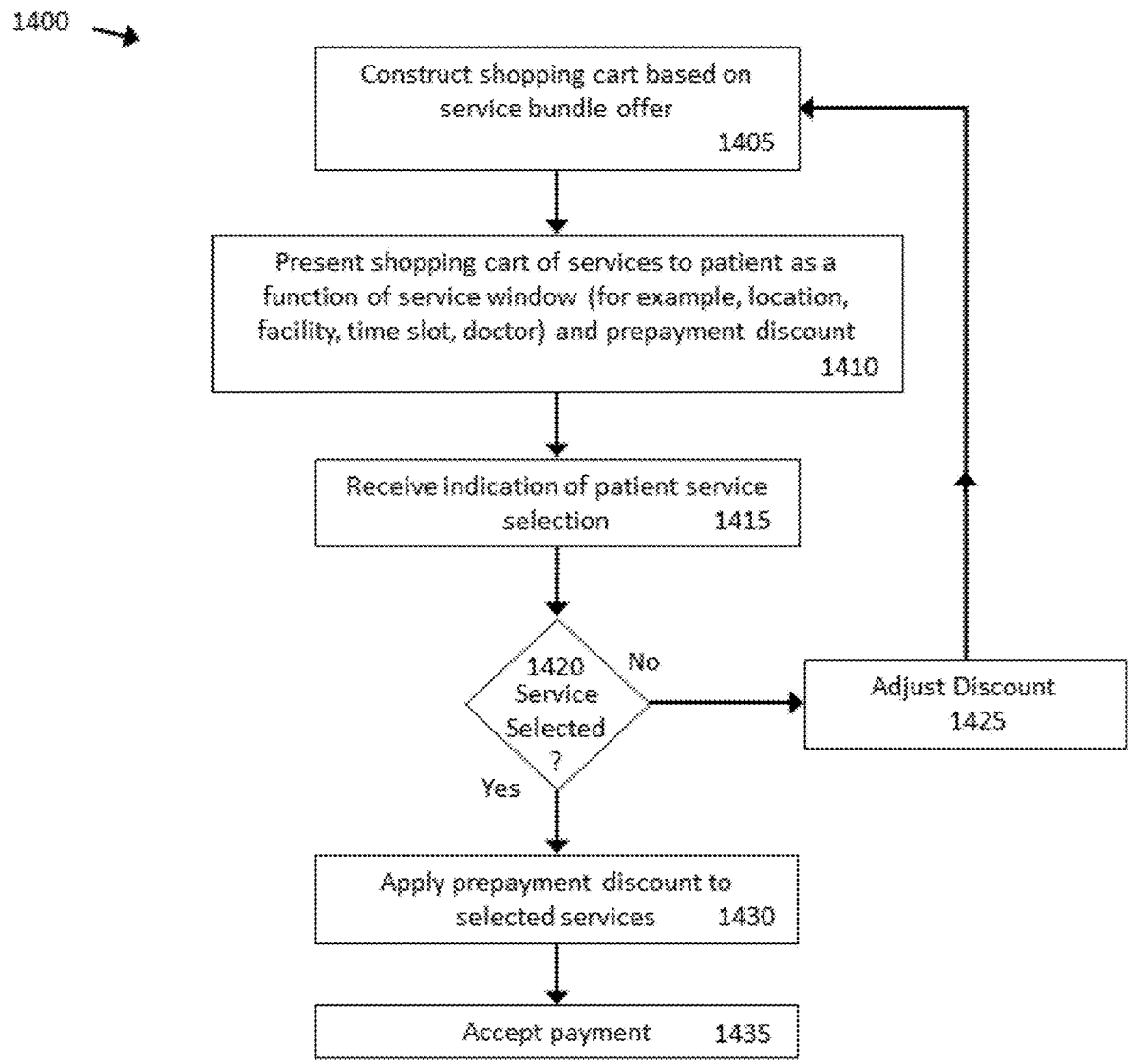
FIG. 14 is a process flow illustrative of an example aspect of patient lifecycle event triggered shopping cart provisioning design.

Then, the method continues at step 1125 with the processor 604 executing the process 1400, depicted by FIG. 14 and described herein, to offer the medical service bundle for selection and prepayment. For example, the processor 604 may offer the medical service bundle for selection and payment through the customer portal 120 (depicted by FIG. 2), using techniques similar to those described herein with reference to the account management service 122 and purchasing service 126 (both depicted by FIG. 2).

Then, the method continues at step 1130 with the processor 604 performing a test to determine if payment for the medical service bundle has been received. Upon a determination by the processor 604 at step 1130 payment has not been received, the method continues at step 1105 with the processor 604 receiving an electronic message comprising a patient medical data update.

Upon a determination by the processor 604 at step 1130 payment was received, the method continues at step 1135 with the processor 604 scheduling the paid services. In various embodiments, the method may repeat. In some designs, the method may end.

Figure 12:
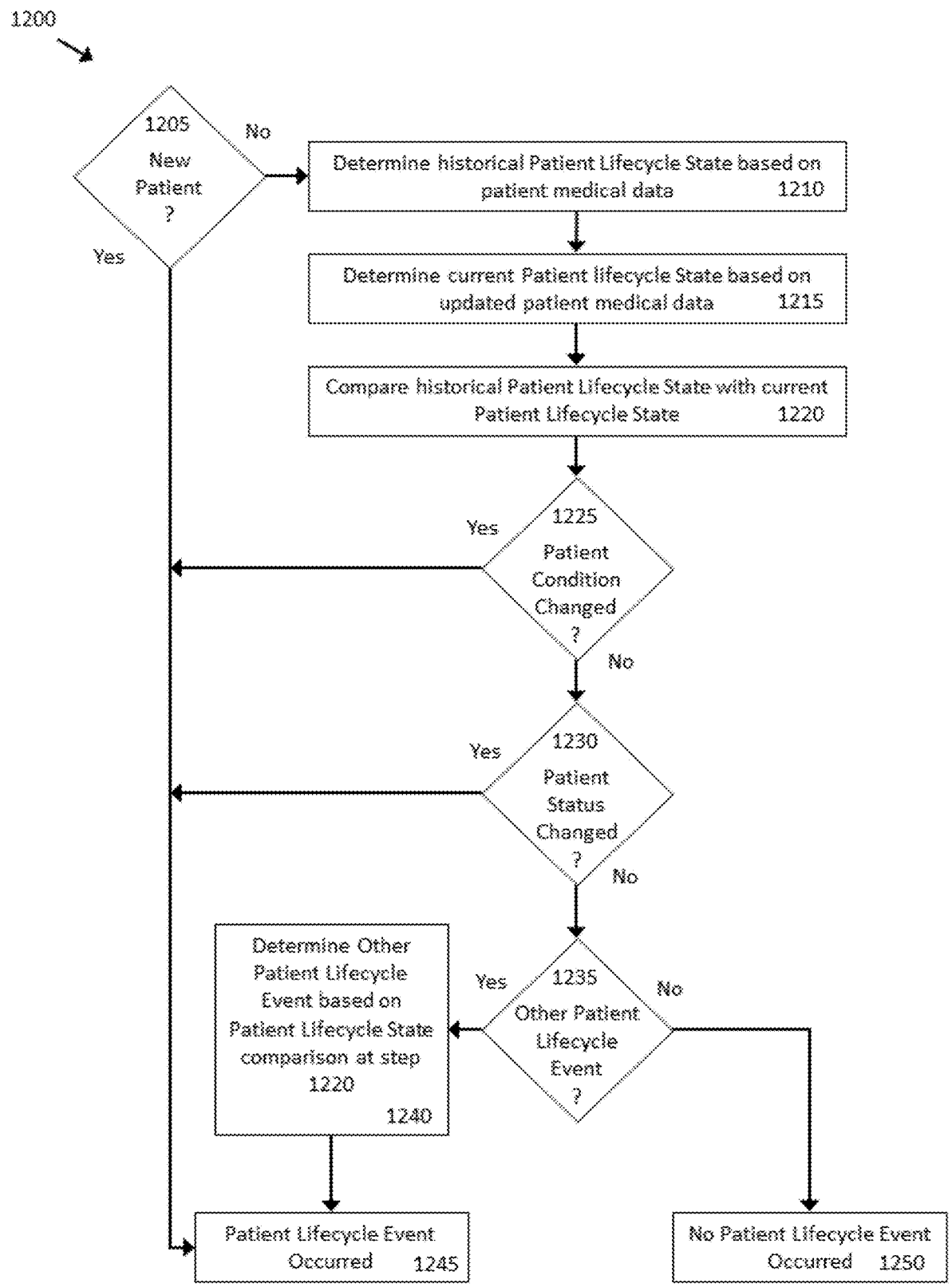
FIG. 12 is a process flow illustrative of an example aspect of patient lifecycle event triggered shopping cart provisioning design.

FIG. 12 is a process flow illustrative of an example aspect of patient lifecycle event triggered shopping cart provisioning design. The method depicted in FIG. 12 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1200 may be configured in an exemplary system 100 as described herein with reference to any of FIGS. 1, 6, and 9. In various embodiments, the method depicted in FIG. 12 may also be understood as from the perspective of processor-executable program instructions executing on a mobile device operably coupled with the network 150, depicted at least in FIGS. 1, 6, and 9. For example, the depicted process may execute as processor executable program instructions on processor 604 configured in the application server 116, depicted in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1200 begins at step 1205 with the processor 604 performing a test to determine if the patient is a new patient. The processor 604 may implement the test to determine if the patient is a new patient based on patient medical data encoded by an EHR.

Upon a determination by the processor 604 at step 1205 the patient is a new patient, the method continues at step 1245 with the processor 604 indicating to the invoking process that a patient lifecycle event occurred.

Upon a determination by the processor 604 at step 1205 the patient is not a new patient, the method continues at step 1210 with the processor 604 determining the patient's historical patient lifecycle state based on patient medical data. The historical patient lifecycle state may be the patient's lifecycle state previous to the current invocation of process 1200. The historical patient lifecycle state may be administratively assigned. The historical patient lifecycle state may be programmatically determined by the processor 604 as a function of patient medical data encoded by an EHR. The processor 604 may determine the historical patient lifecycle state based on, for example, patient medical data encoded by a previously processed EHR, administratively configured patient medical data, or an administratively configured lifecycle state. In illustrative examples, the EHR may encode patient physiological data such as, for example, a laboratory test report indicating the concentration of a substance in the patient's body, or a test result indicating a measured patient physiological parameter such as blood pressure, heart rate, weight, or height. The processor 604 may programmatically determine the historical patient lifecycle state based on, for example, operations such as comparing, or correlating, patient medical data encoded by an EHR with one or more range of similar data to determine the patient lifecycle state. In an illustrative example, the processor 604 may determine the patient lifecycle state to be new patient, well patient, acute care patient, chronic care patient, or recovering patient. Other patient lifecycle states may be determined by the processor 604 based on programmatically analyzing patient medical data such as laboratory results and measurements to determine correspondence with standardized or administratively determined medical data ranges. For example, at step 1210 the processor 604 may determine a patient with a blood pressure in a predetermined range is an acute care patient based on patient medical data encoded by an EHR.

Then, the method continues at step 1215 with the processor 604 determining the current patient lifecycle state based on updated patient medical data. The processor 604 may programmatically determine the current patient lifecycle state based on updated patient medical data encoded by an EHR. The EHR encoding updated patient medical data may be provided as input to the system as a result of a patient's examination by a medical professional. The EHR encoding updated patient medical data may be provided as input to the system as a result of a measurement by a doctor during a patient visit. The EHR encoding updated patient medical data may be provided as input to the system as a result of a measurement remotely performed by a patient in a care context such as telemedicine, or self-care by the patient in the patient's home. The operations performed by the processor 604 to determine the current patient lifecycle state at step 1215 are in line with the operations performed by the processor 604 at step 1210 to determine the historical patient lifecycle state. In any case, the processor 604 at step 1215 determines the current patient lifecycle state based on evaluating patient medical data that has been updated. In this example, the patient medical data has been updated relative to the patient medical data analyzed by the processor 604 at step 1210 to determine the historical patient lifecycle state.

Then, the method continues at step 1220 with the processor 604 comparing the historical patient lifecycle state determined by the processor 604 at step 1210 with the current patient lifecycle state determined by the processor 604 at step 1215, to determine if a patient lifecycle event occurred based on the comparison. In an illustrative example, the processor 604 may compare the historical and current lifecycle states based on comparing archived patient medica data with updated patient medical data.

Then, the method continues at step 1225 with the processor 604 performing a test to determine if the patient condition changed. The processor 604 may determine if the patient condition changed based on comparing archived patient medical data, such as, for example, a previous blood pressure measurement or laboratory test result, with patient medical data updated by a more recent measurement or result. For example, the processor 604 may determine patient condition changed if a more recent test result or measurement is in a different range than a previous test result or measurement. Upon a determination at step 1225 by the processor 604 patient condition changed, the method continues at step 1245 with the processor 604 indicating to the invoking process that a patient lifecycle event occurred.

Upon a determination by the processor 604 at step 1225 the patient condition did not change; the method continues at step 1230 with the processor 604 performing a test to determine if the patient status changed. The processor 604 may determine if patient status changed based on administratively configured or programmatically determined patient status. The processor 604 may determine if patient status changed based on comparing archived patient data with updated patient data. The patient data used by the processor 604 to determine patient status may be medical, billing, payment, insurance, or other data. In an illustrative example, patient status may be new patient, active patient, inactive patient, former patient, referral patient, or referred patient. For example, the processor 604 may determine patient status changed from active to inactive if the patient has not kept an appointment for at least a predetermined time period. The processor 604 may determine the patient is a new patient if patient records were not previously accessible to the system. A referral patient may have been referred from another medical practice, and in view of this, patient care of such a patient may benefit from customized consideration, in line with what may be known by one of skill in the art. A referred patient may have specific goals resulting in the patient's referral to another medical practice, or to a specialist, for example. In an illustrative example, the referred patient may benefit from optional services offered through the specialist's practice. In any case, upon a determination by the processor 604 at step 1230 the patient status changed, the method continues at step 1245 with the processor 604 indicating to the invoking process that a patient lifecycle event occurred.

Upon a determination by the processor 604 at step 1230 the patient status did not change, the method continues at step 1235 with the processor 604 performing a test to determine if another patient lifecycle event occurred. The operations performed by the processor 604 at step 1235 to determine if another patient lifecycle event has occurred may include comparing archived patient data with updated patient data encoded by an EHR received with a notification or administratively configured in the system. In any case the processor 604 may determine a patient lifecycle event other than a change in patient condition or status has occurred, based on comparing the archived and updated patient data, to determine if a change has occurred based on the comparison. The change detected by the processor 604 may be any change in patient data that has not been identified previously.

Upon a determination by the processor 604 at step 1235 another patient lifecycle event has not occurred, the method continues at step 1250 with the processor 604 indicating to the invoking process that no patient lifecycle event occurred.

Upon a determination by the processor 604 at step 1235 another patient lifecycle event has occurred, the method continues at step 1240 with the processor 604 determining the patient lifecycle event that did occur, based on the patient lifecycle state comparison performed by the processor 604 at step 1220. The operations performed by the processor 604 to determine the patient lifecycle event at step 1240 are in line with the operations performed by the processor 604 at step 1225 and step 1230 with deeper analysis of the patient data at step 1240. The patient data analysis performed by the processor 604 at step 1240 may include lifecycle event determination based on patient data input to a predictive analytic, machine learning, or artificial intelligence model trained with patient data.

Then, the method continues at step 1245 with the processor 604 indicating to the invoking process that a patient lifecycle event occurred. In various embodiments, the method may repeat. In some designs, the method may end.

FIG. 13 is a process flow illustrative of an example aspect of patient lifecycle event triggered shopping cart provisioning design. The method depicted in FIG. 13 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1300 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 13 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1300 begins at step 1305 with the processor 604 creating a default service bundle. The default service bundle created by the processor 604 may include a service for which a patient is already registered. The service for which the patient is already registered may be a primary service. The default service bundle may include a service window parameter related to a bundled service, such as, for example, location, facility, time slot, or doctor. The processor 604 may create the default service bundle as an empty bundle with no service, or no service window.

Then, the method continues at step 1310 with the processor 604 identifying appropriate optional services to offer to the patient based on patient medical data. The processor 604 may determine an optional service is appropriate to a patient if the optional service considered is not contraindicated by medical care standards, in view of the patient's medical condition. The patient's medical condition may be determined by the processor 604 using techniques similar to those described herein with reference to process 1200, depicted by FIG. 12.

Then, the method continues at step 1315 with the processor 604 determining if any of the optional services determined at step 1310 by the processor 604 as appropriate are medically indicated for the patient based on the current patient lifecycle event and patient medical data. The processor 604 may determine an optional service is medically indicated for a patient if the service is related by medical care standards to the patient condition. For example, if a medical care standard suggests a doctor treating a patient with a given condition should also consider treatment with a particular class of drug or screening by a particular test for another condition, the processor 604 may determine that consideration of the drug treatment or screening test may be medically indicated for the patient based on the current patient lifecycle event and patient medical data. The current patient lifecycle event may be determined by the processor 604 using techniques similar to those described herein with reference to process 1200, depicted by FIG. 12.

Then, the method continues at step 1320 with the processor 604 performing a test to determine if medically indicated procedures should be added to the default service bundle, based on the determination by the processor 604 at step 1315, as to whether appropriate optional services may be medically indicated. Upon a determination at step 1320 by the processor 604 some appropriate optional service is medically indicated, the method continues at step 1325 with the processor 604 adding at least one medically indicated appropriate optional service to the default service bundle. The service added to the service bundle by the processor 604 may include a service window parameter related to the added service, such as, for example, location, facility, time slot, or doctor.

Upon a determination at step 1320 by the processor 604 no appropriate optional service is medically indicated, the method continues at step 1330 with the processor 604 performing a test to determine if a follow-up service may be added to the service bundle. A follow-up service may be, for example, mandatory, such as a post-surgical visit for suture removal. In some cases, a follow-up service may be optional. A candidate follow-up service considered by the processor 604 for addition to the service bundle may be a follow-up service to a primary service, or a follow-up service to an optional service. Upon a determination by the processor 604 at step 1330 some follow-up service may be added to the service bundle, the method continues at step 1335 with the processor 604 adding at least one follow-up service to the service bundle.

Upon a determination by the processor 604 at step 1330 no follow-up service may be added to the service bundle, the method continues at step 1340 with the processor 604 determining if additional optional services are available within the same service window (for example, location, facility, time slot, or doctor) as a primary service.

Then, the method continues at step 1345 with the processor 604 performing a test to determine if an optional service available in the same service window as a primary service may be added to the service bundle. Upon a determination at step 1345 by the processor 604 an optional service available in the same service window as a primary service may be added to the service bundle, the method continues at step 1350 with the processor 604 adding to the service bundle an optional service available within the same service window as a primary service.

Upon a determination at step 1345 by the processor 604 no optional service available in the same service window as a primary service may be added to the service bundle, the method continues at step 1355 with the processor 604 determining if performing bundled services in another optional service window (that is, a service window different from, or alternative to, the primary service window) would improve resource utilization. The resource utilization data evaluated by the processor 604 at step 1355 may include facility, equipment, or medical professional cost per unit time, percent idle time, or percent active time. The processor 604 may determine if resource utilization may be improved based on comparing calculated projected utilization of one or more resource based on the resource utilization data for more than one service window. The processor 604 may determine the relative cost to provide service in various service windows, to facilitate offering a discount determined by the processor 604 as a function of relative resource utilization between the service windows.

Then the method continues at step 1360 with the processor 604 performing a test to determine if offering service in an alternative service window would improve resource utilization, based on the evaluation of resource utilization in optional service windows performed by the processor 604 at step 1355. Upon a determination by the processor 604 at step 1360 offering service in an alternative service window would improve resource utilization, the method continues at step 1365 with the processor 604 adding an optional service window to the service bundle.

Upon a determination by the processor 604 at step 1360 offering service in an alternative service window would not improve resource utilization, the method continues at step 1370 with the processor 604 adding a prepayment discount determined as a function of relative service window resource utilization to the service bundle offer. In various embodiments, the method may repeat. In some designs, the method may end.

FIG. 14 is a process flow illustrative of an example aspect of patient lifecycle event triggered shopping cart provisioning design. The method depicted in FIG. 14 is given from the perspective of an exemplary patient lifecycle event triggered shopping cart provisioning engine (SCPE) implemented via processor-executable program instructions executing on the SCPE processor 604, depicted in FIG. 5. In various embodiments, the processor 604 implementing the process 1400 may be configured in an exemplary system 100 as described herein with reference to any of FIGS. 1, 6, and 9. For example, the depicted process may execute as processor executable program instructions on processor 604 configured in the application server 116, depicted in FIGS. 1, 6, and 9. In various embodiments, the method depicted in FIG. 14 may also be understood as from the perspective of processor-executable program instructions executing on a mobile device operably coupled with the network 150, depicted at least in FIGS. 1, 6, and 9. In the illustrated embodiment, the SCPE executes as program instructions on the processor 604, depicted in FIG. 5. In some embodiments, the SCPE may execute as a cloud service communicatively and operatively coupled with system services, hardware resources, or software elements local to and/or external to the SCPE processor 604. The depicted method 1400 begins at step 1405 with the processor 604 constructing a shopping cart based on the service bundle offer predetermined by the processor 604 executing the process 1300, depicted by FIG. 13.

Then, the method continues at step 1410 with the processor 604 presenting the shopping cart of bundled services to a patient as a function of service window (for example, a service window may include location, facility, time slot, doctor, or other variables) and a prepayment discount. The shopping cart of bundled services may be presented to the patient in an email, text message, mobile app, web page, chat window, or automated phone call. Various designs may enable the patient to select from among the offered services presented in the shopping cart. In an illustrative example, the shopping cart may offer a choice of service window with some services. For example, given an offered service such as a particular medical procedure, a service window choice presented to the patient with the medical procedure may include a choice of location, facility, time slot, doctor, or other optional procedures available within the service window. In some cases, more than one service window may be presented to a patient for selection. The service window choice may include a prepayment discount. More than one prepayment discount amount or prepayment discount percentage may be offered to a patient. The prepayment discount may vary as a function of the service window. The prepayment discount may be determined as a function of medical practice resource utilization, medical practice cost per unit time to provide a service in the service window, or medical professional availability during the service window. The prepayment discount may be a prepayment discount valid for prepayment before a predetermined date.

Then, the method continues at step 1415 with the processor 604 receiving an indication of patient service selection from the shopping cart of bundled services presented to the patient by the processor 604 at step 1410. The indication of patient service selection may be an indication the patient did not select an offered service after a predetermined time period. The indication of patient service selection may be an indication the patient rejected the offered services.

Then, the method continues at step 1420 with the processor 604 performing a test to determine if the patient selected a service. Upon a determination by the processor 604 at step 1420 the patient did not select a service, the method continues at step 1425 with the processor 604 optionally adjusting the prepayment discount, and the method continues at step 1405 with the processor 604 constructing a shopping cart based on a service bundle offer.

Upon a determination by the processor 604 at step 1420 the patient selected a service, the method continues at step 1430 with the processor 604 applying the prepayment discount to the selected services, and the method continues at step 1435 with the processor 604 accepting payment. In various embodiments, the method may repeat. In some designs, the method may end.

Figure 15:
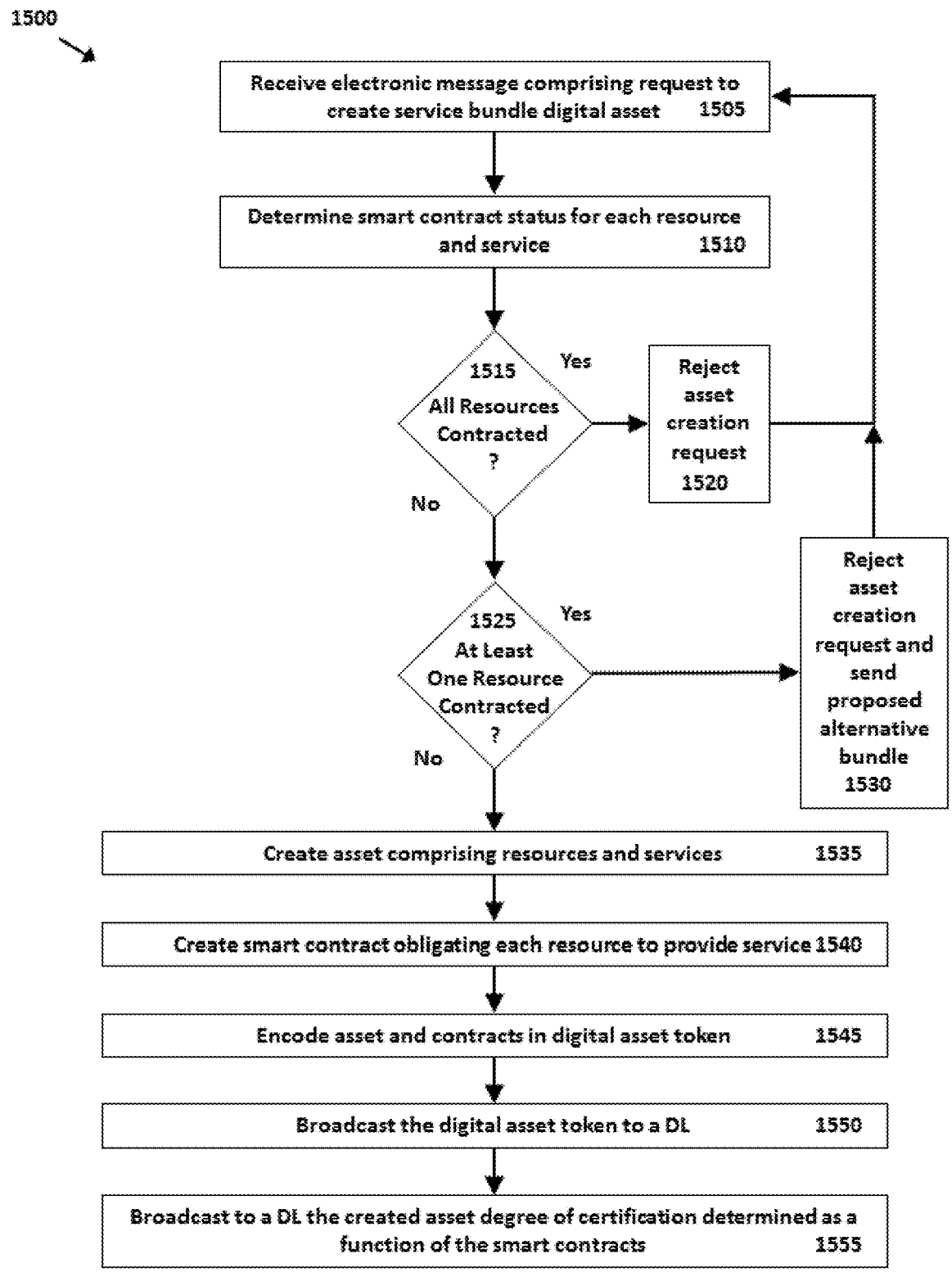
FIG. 15 is a process flow illustrative of an example aspect of digital health asset creation.

FIG. 15 is a process flow illustrative of an example aspect of digital health asset creation. The method depicted in FIG. 15 is given from the perspective of an exemplary digital health asset creation engine implemented via processor-executable program instructions executing on the processor 604, depicted in FIG. 5. In various embodiments, the processor 604 implementing the process 1500 may be configured in an exemplary system 110 as described herein with reference to any of FIGS. 1AA, 1AM, 1AN, 2, 6, and 9. The method depicted in FIG. 15 may also be understood as from the perspective of processor-executable program instructions executing on a mobile device operably coupled with the network 150, depicted at least in FIGS. 1AA, 1AM, 1AN, 2, 6, and 9. In the illustrated embodiment, the digital health asset creation engine executes as program instructions on the processor 604, depicted in FIG. 5. In some embodiments, the digital health asset creation engine may execute as a cloud service communicatively and operatively coupled with system services, hardware resources, or software elements local to and/or external to the processor 604.

The depicted method 1500 begins at step 1505 with the processor 604 receiving an electronic message comprising a request to create a service bundle digital asset. The request may include a service bundle definition.

The method continues at step 1510 with the processor 604 determining the smart contract status for each resource and service encoded by the request. The processor 604 may recursively evaluate the existence or status of a smart contract governing multiple services.

The method continues at step 1515 with the processor 604 performing a test to determine if all service resources are governed by a smart contract, based on the contract status determined by the processor 604 at step 1510.

Upon a determination by the processor 604 at step 1515 all resources are governed by a smart contract to provide service, the method continues at step 1520 with the processor 604 sending an electronic message comprising a rejection of the asset creation request, and the method continues at step 1505 with the processor 604 receiving an electronic message comprising a request to create a service bundle digital asset. The rejection message may be status encoded in a digital asset token and broadcast to a DL. In an illustrative example, the processor 604 enforces the non-fungible property of digital assets created by the process, based on the processor 604 rejecting the asset creation request in response to determining all resources are governed by a smart contract to provide service. The processor 604 may reject the asset creation request to enforce the non-fungible property based on a non-fungible property definition including a list of resources required to provide a service. The non-fungible property definition for a service or service bundle may be published by a provider, to a DL accessible to the processor 604.

Upon a determination by the processor 604 at step 1515 all resources are not governed by a smart contract to provide service, the method continues at step 1525 with the processor 604 performing a test to determine if at least one resource is governed by a smart contract to provide service.

Upon a determination by the processor 604 at step 1525 at least one resource is governed by a smart contract to provide service, the method continues at step 1530 with the processor 604 sending an electronic message comprising a rejection of the asset creation request with a proposed alternative service bundle, and the method continues at step 1505 with the processor 604 receiving an electronic message comprising a request to create a service bundle digital asset. The alternative service bundle may be determined by the processor 604 based on a published list of resources required to provide a service.

Upon a determination by the processor 604 at step 1525 no resource is governed by a smart contract to provide service, the method continues at step 1535 with the processor 604 creating the service bundle digital asset comprising the bundled resources and services.

Then, the method continues at step 1540 with the processor 604 creating a smart contract obligating each resource to provide their respective service.

Then, the method continues at step 1545 with the processor 604 encoding the asset and smart contracts in a digital asset token.

Then, the method continues at step 1550 with the processor 604 broadcasting the created digital asset token to one or more DL.

Then, the method continues with the processor 604 broadcasting to one or more DL the created asset degree of certification determined as a function of the smart contracts.

In various examples, the method may repeat. In some cases, the method may end.

Figure 16:
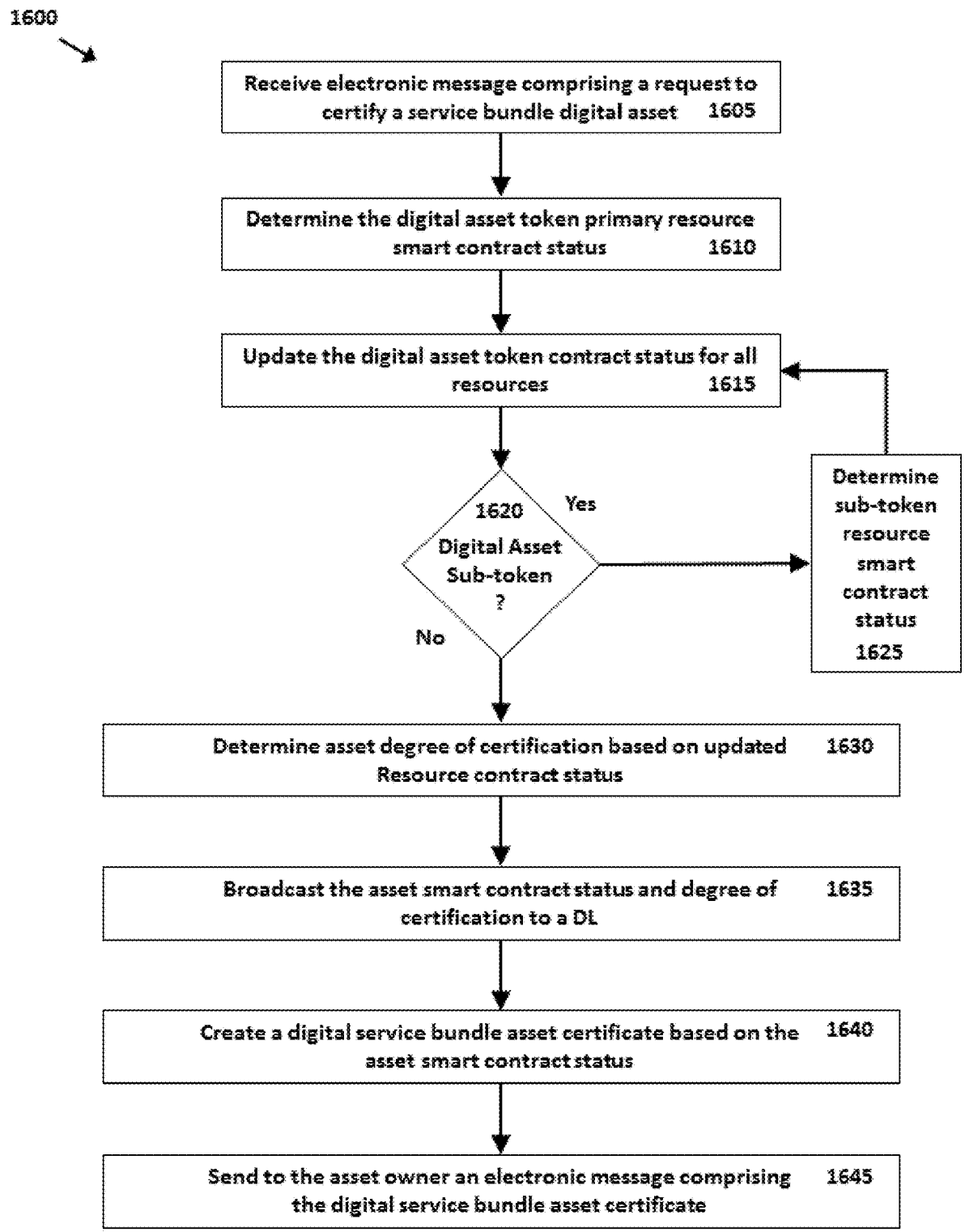
FIG. 16 is a process flow illustrative of an example aspect of digital health asset certification.

FIG. 16 is a process flow illustrative of an example aspect of digital health asset certification. The method depicted in FIG. 16 is given from the perspective of an exemplary digital health asset certification engine implemented via processor-executable program instructions executing on the processor 604, depicted in FIG. 5. In various embodiments, the processor 604 implementing the process 1600 may be configured in an exemplary system 110 as described herein with reference to any of FIGS. 1AA, 1AM, 1AN, 2, 6, and 9. The method depicted in FIG. 16 may also be understood as from the perspective of processor-executable program instructions executing on a mobile device operably coupled with the network 150, depicted at least in FIGS. 1AA, 1AM, 1AN, 2, 6, and 9. In the illustrated embodiment, the digital health asset certification engine executes as program instructions on the processor 604, depicted in FIG. 5. In some embodiments, the digital health asset certification engine may execute as a cloud service communicatively and operatively coupled with system services, hardware resources, or software elements local to and/or external to the processor 604.

The depicted method 1600 begins at step 1605 with the processor 604 receiving an electronic message comprising a request to certify a service bundle digital asset. The service bundle digital asset may be certified at a token and sub-token level to a degree of certification determined as a function of the status of a smart contract governing each resource.

The method continues at step 1610 with the processor 604 determining the digital asset token primary resource smart contract status.

The method continues at step 1615 with the processor 604 updating the digital asset token smart contract status maintained by the processor 604 for all resources encoded by the digital asset token.

The method continues at step 1620 with the processor 604 performing a test to determine if the digital asset token includes a sub-token resource to be certified.

Upon a determination by the processor 604 at step 1620 the digital asset token includes a sub-token to be certified, the method continues at step 1625 with the processor 604 determining the sub-token resource smart contract status, and the method continues at step 1615 with the processor 604 updating the digital asset token contract status.

Upon a determination by the processor 604 at step 1620 the digital asset token does not include a sub-token to be certified, the method continues at step 1630 with the processor 604 determining the asset degree of certification based on the updated resource smart contract status.

Then, the method continues at step 1635 with the processor 604 broadcasting the asset smart contract status and degree of certification to a DL.

Then, the method continues at step 1640 with the processor 604 creating a digital service bundle asset certificate based on the asset smart contract status. The certificate may be signed by each resource governed by a contract.

Then, the method continues at step 1645 with the processor 604 sending to the asset owner an electronic message comprising the digital service bundle asset certificate. The certificate may be encoded in a digital asset token and broadcast to a DL.

In various examples, the method may repeat. In some cases, the method may end.

Although various embodiments have been described with reference to the Drawings, other embodiments are possible. In an illustrative example, a Digital Health Asset (DHA) may define a unit of purchase that is a digital asset representing a bearer instrument for the service(s) offered by the seller. Such DHA may be created to represent a wide variety of traditional and non-traditional products and services. Exemplary DHA may represent healthcare services digitally as a "non-fungible" token, which may be referred to herein as "digital health assets" or "DHA's." Using the DHA, the unit of purchase in healthcare service delivery may be fundamentally re-cast, replacing small atomic codes with a non-fungible token representation of healthcare services. For example, it is the seller who decides the terms, conditions, pricing, service description, provider information and other data which is embedded on the DHA. Sellers therefore assume control over the "packaging" or "bundling" of services.

In an illustrative example, such a platform enables purchasers of healthcare services to rationally shop the market for the desired service according to the prices, terms, and other preferences that they desire. In some examples, a blockchain implementation may allow buyers and sellers a trusted DHA exchange medium without the need for intermediaries that may create non-value-added influence or unnecessary value extraction. Purchasers may redeem the DHA at the point of service or choose to re-list the asset on the exchange or a secondary market.

In an illustrative example, DHA's may be created, offered, purchased, rented, expired, and returned, and/or burned (removed from circulation) as per the design of the exchange participants. Some DHA's may be made to be temporary or conform to a specific time period. DHA's may be deflationary or inflationary. When bundled, DHA tokens may include multiple sub-tokens with each separate token having a unique set of values. If a sub-token is removed, the single token may be moved to minimize transaction fees. Sub-tokens may be tracked as part of the bundle and can be reported on individually if necessary.

A number of distinct classes of non-fungible offerings emerge from this simple template. A few examples include Pre-Purchase, Open Redemption, and Bundled Offerings. For certain discrete and well-defined services such as diagnostics and lab services, it may be that a pre-purchased asset makes most sense. These pre-paid offerings can be expirable, requiring the services to be redeemed within an agreed upon time-window, for example, 1 week, 6 months or a "plan year." The benefits of such an arrangement are many. The service provider can sell in bulk and receive payment up front, avoiding costly, inefficient, and lengthy account receivable processes. For the buyer, the ability to pre-purchase, even in bulk, gives the ability to negotiate for significant discounts and savings over the status quo. This model of service offering fits well with efforts to enable populations to compare "shoppable" healthcare services. A shorter time window could be used to offload near-term excess capacity. A bundled offering can be used when a service or therapy is less simple. Care may require multiple services delivered by a number of different providers. Despite this complexity, many such services are predictable. Examples include joint replacement surgeries and chronic disease care.

DHA functionality allows providers to more easily combine offerings into more coherent, patient-focused bundles of care. Additionally, providers' agreement on how a single payment is apportioned among a group can be hard-coded into the DHA itself, allowing easier coordination among groups of otherwise unaffiliated providers. Physicians may form new ad-hoc networks for tighter coordination and services combinations.

In an illustrative example, a provider listing a DHA may set a reserve price at which they would no longer supply. The purchasing organization (for example, insurer, TPA, or employer) may set a maximum reserve price. Some designs may include "Bidding Bots" configured to automatically engage purchasers, and clear the market.

A service bundle digital asset, or DHA, may be configured to permit exchange of the digital asset based on the intrinsic value of resources allocated to provide a bundled service. A service bundle digital asset may be implemented as a transaction unit configured to represent a bundle of healthcare services underlying the digital asset. A service bundle digital asset may be encoded by a digital asset token. The digital asset token may be stored in memory, transmitted, or received via a communication network, processed, and manipulated, to permit exchange of the digital asset. A DHA may be temporary, or conform to a specific time period. A DHA may be deflationary, or inflationary. The digital asset token may include one or more sub-token. A token may encode a reference to a sub-token. When representing bundled services, a token may encode multiple sub-tokens with each sub-token having a unique set of values. A resource required to provide a service included in a service bundle may be represented by a sub-token. The token representing the service bundle may encode a reference to a sub-token. A token or sub-token may be individually manageable. For example, a new sub-token may be created. The new sub-token may be added to an existing token. A sub-token encoded by a token may be deleted. In an illustrative example, if a sub-token is removed from a token, the sub-token, or the remaining token, may be transferred, traded, or sold, to minimize transaction fees, or to enhance bundle customization. A sub-token may be tracked as part of a bundle. A sub-token may be individually accounted for, sold, transferred, redeemed, or reported on.

In an illustrative example of a service bundle digital asset, a primary service may be represented as a digital asset token encoding a reference to a sub-token that represents a secondary service. The digital asset token representing the primary and secondary services may be configured to encode the services, resources, initial price, quantity, expiration date, or validity date related to the services represented by the digital asset token. The expiration date may be a date or time when the asset becomes unavailable for delivery or redemption of the associated service. The validity date may be a date or time when the asset initially becomes available for delivery or redemption of the associated service.

Creating a digital asset may include receiving an indication of services and resources specified by a provider. The asset may be created based on a service bundle defined by resources required to provide the bundled services, such as, for example, location; time; service; provider; facility; professionals, such as doctors, nurses, or technicians; equipment; or support services.

A service bundle digital asset may be a non-fungible digital asset. The service bundle digital asset may represent a bearer instrument for a service offered by a provider. The provider may define the terms, conditions, pricing, service description, provider information, and other data encoded by a service bundle digital asset. A non-fungible service bundle digital asset may be a non-reproducible digital asset representing a unique service bundle. For example, the non-fungible digital asset may be linked to a specific tangible asset or resource allocated or obligated to provide a bundled service. The specific tangible asset or resource may provide the digital asset with underlying value. The specific tangible asset or resource may be uniquely defined by a combination of physical elements, such as, for example, location, time, service type, or professional resource allocated to provide the service. A non-fungible digital asset uniquely defined by such a physical element combination may be a unique and non-copyable asset that cannot be replicated. Such a non-fungible digital asset may have a value based on the asset's scarcity and uniqueness, and the intrinsic value of the resources underlying the asset, such as, for example, professional or facility time allocated to provide a service.

In an illustrative example, a DHA (Digital Health Asset) may be a digital token encoding an asset, based on a header uniquely identifying the asset and an asset payload encoding asset parameters including a unique reference to the header. The header may be stored or transmitted separately from the payload, permitting efficient token storage and communication. In some examples, the header may include a mutable asset state value in an otherwise immutable header, permitting an efficient test to determine if an asset has been redeemed. The digital asset token payload may include a unique reference to the header. The unique reference to the header encoded by the payload may include a copy of the asset identifier encoded by the header; the hash of the header; and a number only used once (nonce). The asset identifier may be unique within a predetermined namespace.

Encoding the unique asset identifier in both the header and payload of a digital asset token may permit the header and payload of a particular token to be separately stored, transmitted, or operated on by various transactions. A particular token's header and payload that each encode the token's unique asset identifier may be used or operated on separately, and recombined as needed, to form a complete token. For example, a digital asset token's header may be separated from the associated payload. The separated header may be broadcast to a DL (Distributed Ledger) transaction stream. A transaction stream may include, for example, only headers, but not payloads, or only payloads, but not headers, of various digital asset tokens. The respective digital asset payload associated with a header by the unique identifier encoded in both the header and payload may be separately stored, for example in a database, or a user's digital wallet. In an illustrative example, the payload does not need to be stored or transmitted repeatedly to perform transactions such as trades on the asset, as only the header needs to be transmitted or evaluated to perform a transaction. Transactions or operations on digital asset tokens may be performed separately on headers by themselves, payloads by themselves, or complete tokens each comprising the digital asset token header and payload. In an illustrative example, a digital asset token payload may be stored or transmitted a limited number of times, while the associated digital asset token header may be repeatedly stored, transmitted, evaluated, signed, bought, and sold, with the mutable asset state in the header potentially changing for each transaction, while the unique asset identifier encoded in the header and payload permits the header and payload to be associated and recombined as needed to form the complete digital asset token. Such a separable header digital asset token design may reduce health care transaction effort or cost, based on reducing the quantity of data that must be stored or communicated to facilitate transactions. Such reduction in the quantity of data stored or communicated to facilitate transactions may be a result of permitting transactions based on communicating or storing only the header, without the payload. Such reduced transaction effort or cost may be a result of a digital asset token design including a header that may be stored or transmitted separately from the payload, permitting efficient token header storage and communication and reducing computation and network communication bandwidth requirements, because only the header needs to be stored, transmitted, or evaluated, to perform a DHA operation with reference to the associated DHA token payload, which may be stored separately, for example in one or more database. Encoding the unique asset identifier in both the header and payload of a digital asset token may be considered counterintuitive and inefficient in view of accepted data and network communication design practice, because the unique identifier in the header is duplicated in the payload, appearing to waste storage space and communication bandwidth. Such a design would be considered inefficient in most contexts, however in the context of this example, encoding the unique asset identifier in both the header and payload of a digital asset token may permit the header and payload to be separately stored, transmitted, and operated upon to facilitate various transactions. The separated header and payload may be recombined based on associating the header and payload through the unique asset identifier, permitting efficient token header storage and communication, and reducing computation and network communication bandwidth requirements, because only the header needs to be stored, transmitted, or evaluated, to perform a DHA operation.

Various exemplary implementations may comprise "persistent voucher generation for selective redemption of bundled services" features. The voucher may be pre-paid, to receive a pre-paid service when the voucher is redeemed. The pre-paid voucher may be converted to a Digital Health Asset (DHA) that is at least partially certified as described herein, based on prepayment received for at least one service of a service bundle.

In an illustrative example, operation of exemplary "persistent voucher generation for selective redemption of bundled services" features may cause tangible technical effects at least including creating a persistent voucher selectively redeemable in the future for a purchased primary or secondary service at different times, individually tracking the voucher redemption status for each service in a service bundle, and individually updating the voucher redemption status for a service in the service bundle when the service is performed. For example, a persistent service bundle voucher may permit individual services comprising the service bundle to be selectively redeemed, and the redemption status of each individual service updated in the data store to indicate the current voucher redemption status of each service in the service bundle, enabling the same voucher uniquely identified by the confirmation number to persist for multiple service redemptions at different times and locations. Such persistent voucher generation for selective redemption of bundled services features are at least one technical solution, necessarily rooted in computer and information technology such as disclosed herein, to the technical problem of persistently tracking and updating the redemption status for each service of a service bundle of services to be performed separately, as the individual services are selectively redeemed.

In an illustrative example of a "persistent voucher generation for selective redemption of bundled services" features implementation, the service offer database may comprise a plurality of service offer information records respectively associated with a plurality of service offers. The plurality of service offers may include at least one service offer for a bundled set of services. The bundled set of healthcare services may be services that are performed separately by multiple providers to prospective patients through such a network-based mechanism in which a patient is provided the opportunity to make a prepaid purchase of such a bundled set of services in a single transaction via a network-connected device, whereby the network-based application facilitates a disbursed distribution of the payment among the multiple healthcare service providers that perform services included in the bundled set of services. In an illustrative example, if a particular healthcare service is offered as a bundled set of services, the cost information that is included in the respective information record for the primary service may be maintained within an available services database. Various implementations may be configured to provide a healthcare service information page that is implemented by navigation and search service 124 for a particular healthcare service that is being offered as a bundled set of services. The healthcare service information page may also present additional information relevant to the bundled set of services. Information presented in provider listing section 326 may be generated in a manner similar to the information included in result listing section 311 of example search result listing page 310 depicted in FIG. 3B to present a list of providers offering the particular service within a default search radius (for example, 50 miles) of a location. In an illustrative example, the network service, upon being accessed by a user of one of the client systems to process a purchase of a service offer, may generate a voucher for the user that specifies a unique confirmation number for the purchase. The confirmation number 408 for the purchase, may be generated by purchasing server 126 based on the unique transaction identifier that is included in the respective information record for the purchase that is maintained within transaction information database. Various implementations may be configured to, upon processing the payment for the purchase of the offered service that is being offered as a primary service in conjunction with a bundled set of services, generate a voucher for the customer user within the user interface for the purchased service that can be utilized by the customer user to redeem the purchase and receive the service from the corresponding physician specified for each of the services of the bundled set of services. An example of such a voucher for a bundled set of services is illustrated in FIG. 4B. As depicted in the example, example voucher 400 can be generated to include identifying information for the customer user 402, identifying and contact information for each physician specified for a service and any facility included in the offered service 404, a description of each service of the purchased service 406, a confirmation number 408 for the purchase, which may be generated by purchasing server 126 based on the unique transaction identifier that is included in the respective information record for the purchase that is maintained within transaction information database 114k, and instructions for redeeming the voucher. Some implementations may be configured to, upon processing the payment for the purchase, generate a confirmation number 408 for the purchase, which may be generated by purchasing server 126 based on the unique transaction identifier that is included in the respective information record for the purchase that is maintained within transaction information database 114k, and instructions for redeeming the voucher 410. In an illustrative example, when a payment for an offered service is processed, some implementations may be configured to also generate a respective information record for the completed purchase within transaction information database which initially indicates that the purchase has not yet been redeemed with respect to a purchase of an individual service or with respect to each service for a purchase of a bundled set of services, and generate a voucher for the customer user to use with respect to the purchased service to redeem the purchase by receiving the service from the physician specified for each service included in the purchase. Such a voucher can include a confirmation number or other redemption code for the purchase. Some implementations may be configured to, upon processing the payment for the purchase of the offered service, send an electronic confirmation message to the customer user and electronic notifications to the physician user that will be performing the service and the provider user. Various implementations may be configured to generate a respective information record for the completed purchase with corresponding information within transaction information database 114k, which initially indicates that the purchase has not yet been redeemed. In an illustrative example, some designs may be configured to, upon processing the payment for the purchase of the offered service that is being offered as a primary service in conjunction with a bundled set of services, generate a respective information record for the completed purchase with corresponding information within transaction information database 114k, which initially indicates that the purchase has not yet been redeemed with respect to the primary service, each secondary service, and any facility specified for the purchased offered service. In some implementations, upon the user indicating an intention to request payment for a purchased service, the system may be configured, for example, to implement a voucher history page within the user interface that presents information relevant to the purchased service, maintained within transaction information database 114k. The relevant information for each listed purchase may include, for example, the voucher confirmation number. Some designs may be configured, for example, to implement a display of the voucher history maintained within transaction information database. The voucher history may further comprise voucher redemption status for each primary service and each secondary service, or other service, related to the primary service. In some implementations, database information records relevant to the purchase may be included in the respective information record that may include a unique transaction identifier that is used by application server 116 to uniquely identify the information record, and provide an indication of whether the purchase has been redeemed and, if the purchase has been redeemed, a redemption date. The information records for purchased services within the transaction information database may include a bundled set of services, the primary service of the bundled set of services, and, for each service of the bundled set of services that is included within the purchase, an indication of whether the purchase has been redeemed with respect to that particular service, and, if the purchase has been redeemed with respect to that particular service, a redemption date for that particular service. Some implementations may be configured to execute a voucher processing session to present a voucher history page within the user interface that presents information relevant to a list of purchases, including a respective information record for the purchase that is maintained within the transaction information database and includes each service included in the purchase (for example, a primary or secondary service for a bundled set of services). The relevant information for each listed purchase may include, for example, the voucher confirmation number or redemption code, a purchase date, and a voucher redemption status. Such a voucher history page may also be accessed in association with the user account for the physician user to verify vouchers presented by customers requesting to have a service performed in association with a voucher. Such a voucher history page may also be accessed in association with a user account, to verify vouchers presented by customers requesting to have a service performed in association with a voucher. In an illustrative example, various implementations may be configured to present the voucher history in association with each of the listed purchases for which the voucher redemption status for the service indicates the service has not been performed, and to permit a user to submit a verification that the physician has performed the service. At least one service offer information record associated with a service offer for a bundled set of services may further comprise an indication of a facility for performing the primary service, a facility fee for the facility, and compensation information for the facility fee. If the selected service offer is a service offer for a bundled set of services for which the associated service offer information record includes an indication of a facility for performing the primary service, upon receiving a notification from one of the client systems that the primary service of the selected service offer has been performed, the network service may operate to access a servicer for a financial account indicated by the compensation information for the facility fee in the service offer information record to direct a disbursement of funds. In an illustrative example, some implementations may be configured to present the voucher history in association with each of the listed purchases for which the voucher redemption status for the service indicates the service has not been performed, and configured to permit a user to submit a verification the provider has performed the service. Some implementations may be configured to, upon receiving such a verification, to update in the service offer database the indication of whether the purchase has been redeemed with respect to that particular service, in the information record for the purchased service that is maintained within transaction information database.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

In the present disclosure, various features may be described as being optional, for example, through the use of the verb "may.", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation, and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

The Abstract is provided to comply with 37 C. F. R. § 1.72(b), to allow the reader to quickly ascertain the nature of the technical disclosure and is submitted with the understanding that it will not be used to interpret or limit the scope or meaning of the claims.

In the present disclosure, any method or apparatus embodiment may be devoid of one or more process steps or components. In the present disclosure, embodiments employing negative limitations are expressly disclosed and considered a part of this disclosure.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Recitation in a claim of the term "first" with respect to a feature or element does not necessarily imply the existence of a second or additional such feature or element.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Aspects of exemplary embodiments of the present invention described herein can be implemented using one or more program modules and data storage units. As used herein, the term "modules", "program modules", "components", "systems", "tools", "utilities", and the like include routines, programs, objects, components, data structures, and instructions, or instructions sets, and so forth that perform particular tasks or implement particular abstract data types. As can be appreciated, the modules refer to computer-related entities that can be implemented as software, hardware, firmware, and/or other suitable components that provide the described functionality, and which may be loaded into memory of a machine embodying an exemplary embodiment of the present invention. Aspects of the modules may be written in a variety of programming languages, such as C, C++, Java, etc. The functionality provided by modules used for aspects of exemplary embodiments described herein can be combined and/or further partitioned.

As used herein, the terms "data storage unit," "data store", "storage unit", and the like can refer to any suitable memory device that may be used for storing data, including manual files, machine readable files, and databases. The modules and/or storage units can all be implemented and run on the same computing system (for example, the exemplary computer system illustrated in FIG. 5 and described below) or they can be implemented and run on different computing systems. For example, one or modules can be implemented on a personal computer operated by a user while other modules can be implemented on a remote server and accessed via a network.

According to an embodiment of the present invention, the system and method may be accomplished through the use of one or more computing devices. As depicted, for example, at least in FIGS. 1, 2, 5, 6, and 9, one of ordinary skill in the art would appreciate that an exemplary system appropriate for use with embodiments in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with embodiments of the present invention include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and embodiments of the present invention are contemplated for use with any computing device.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions, by combinations of general purpose hardware and computer instructions; and so on—any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

Traditionally, a computer program consists of a sequence of computational instructions or program instructions. It will be appreciated that a programmable apparatus (i.e., computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable, and replaceable, or fixed. It will also be understood that a computer can include a Basic Input/output System (BIOS), firmware, an operating system, a database, or the like that can include, interface with, or support the software and hardware described herein.

Regardless of the type of computer program or computer involved, a computer program can be loaded onto a computer to produce a particular machine that can perform any and all of the depicted functions. This particular machine provides a means for carrying out any and all of the depicted functions.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, embodiments that execute or process computer program instructions, computer-executable code, or the like can suitably act upon the instructions or code in any and all of the ways just described.

While the invention has been described in detail with reference to exemplary embodiments, it will be understood by those skilled in the art that various changes and alternations may be made and equivalents may be substituted for elements thereof without departing from the scope of the invention as defined by the appended claims. In addition, many modifications may be made to adapt a particular application or material to the teachings of the invention without departing from the essential scope thereof.

Variations described for exemplary embodiments of the present invention can be realized in any combination desirable for each particular application. Thus particular limitations, and/or embodiment enhancements described herein, which may have particular limitations need be implemented in methods, systems, and/or apparatuses including one or more concepts describe with relation to exemplary embodiments of the present invention.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112(f), or 35 U.S.C. § 112, sixth paragraph (pre-AIA), unless the element is expressly recited using the phrase "means for" or "step for." These following claims should be construed to maintain the proper protection for the present invention.

What is claimed is:

1. An apparatus comprising:
a processor; and
a memory configured to be operably coupled to the processor, wherein the memory comprises encoded data and processor executable program instructions, wherein the data and instructions jointly configure and program the apparatus that the instructions when executed by the processor cause the apparatus to perform operations comprising:
receive a service offer from a service provider, wherein the service offer comprises identification of a named healthcare service provider; and
construct in the memory a digital asset token for the service offer, the digital asset token comprising:
a header, encoding:
an immutable asset identifier representing the service offer;
an immutable asset exchange identifier;
an immutable asset creation time representing the time at which the digital asset token was constructed;
a mutable asset state value representing the minting state;
a payload, encoding;
the service offer;
a copy of the asset identifier encoded by the header;
the hash of the header;
a nonce;
send the header without the payload to a first application server; and
send the payload without the header to a second application server.

2. The apparatus of claim 1, wherein the asset identifier is unique within a predetermined namespace.

3. The apparatus of claim 1, wherein the exchange identifier is unique within a predetermined namespace.

4. The apparatus of claim 1, wherein the operations performed by the apparatus further comprise: in response to receiving payment for the digital asset, set the state value to sold.

5. The apparatus of claim 1, wherein the service offer further comprises the service offer encoding a plurality of references to a respective plurality of smart contracts, and wherein the operations performed by the apparatus further comprise broadcast to a Distributed Ledger (DL) the asset degree of certification determined as a function of the fraction of the smart contracts that obligate at least one resource to provide at least one service associated with the service offer.

6. The apparatus of claim 1, wherein the service offer further comprises a price.

7. The apparatus of claim 1, wherein the payload further comprises a reference to a contract related to the named healthcare service provider.

8. The apparatus of claim 7, wherein the payload further comprises an asset class value determined as a function of the contract status.

9. The apparatus of claim 1, wherein the service offer further comprises: a reference to a service bundle; a reference to a contract defining service bundle provision terms, and an asset class value determined as a function of the contract status.

10. The apparatus of claim 9, wherein the service bundle further comprises a healthcare service.

11. The apparatus of claim 10, wherein the contract encodes a location and time at which the healthcare service will be performed.

12. The apparatus of claim 10, wherein the healthcare service is a primary healthcare service.

13. The apparatus of claim 12, wherein the service bundle further comprises a secondary healthcare service related to the primary healthcare service.

14. The apparatus of claim 9, wherein the service bundle further comprises a plurality of related service bundles.

15. The apparatus of claim 14, wherein each service bundle of the plurality of related service bundles further comprises a subcontract encoding a location, time, facility, and professional resource allocated to provide the service bundle.

16. An apparatus comprising:
a processor; and
a memory configured to be operably coupled to the processor, wherein the memory comprises encoded data and processor executable program instructions, wherein the data and instructions jointly configure and program the apparatus that the instructions when executed by the processor cause the apparatus to perform operations comprising:
receive a service offer from a service provider; and
construct in the memory a digital asset token for the service offer, the digital asset token comprising:
a header, encoding:
an immutable asset identifier representing the service offer, wherein the asset identifier is unique within a predetermined namespace;
an immutable asset exchange identifier, wherein the exchange identifier is unique within a predetermined namespace;
an immutable asset creation time representing the time at which the digital asset token was constructed;
a mutable asset state value representing the trading state;

a payload, encoding:
  the service offer;
  a copy of the asset identifier encoded by the header;
  the hash of the header;
  a reference to an asset bundle, wherein the asset bundle comprises at least one healthcare service;
  a reference to at least one contract defining asset bundle provision terms;
  an asset class determined as a function of the at least one contract status;
  a nonce;
send the header without the payload to an asset exchange identified by the asset exchange identifier; and
broadcast to a DL the asset degree of certification determined as a function of the fraction of the at least one contract that obligates at least one resource to provide at least one service associated with the service offer.

17. The apparatus of claim 16, wherein the at least one contract encodes a procedure, a location, and a time associated with the at least one healthcare service.

18. The apparatus of claim 17, wherein the at least one healthcare service is a primary healthcare service.

19. The apparatus of claim 18, wherein the asset bundle further comprises a secondary healthcare service related to the primary healthcare service.

20. The apparatus of claim 16, wherein the asset bundle further comprises a plurality of related asset bundles.

21. The apparatus of claim 20, wherein each asset bundle of the plurality of related asset bundles further comprises a subcontract encoding a location, time, facility, and professional resource allocated to provide a service included with the asset bundle.

22. An apparatus comprising:
a processor; and
a memory configured to be operably coupled to the processor, wherein the memory comprises encoded data and processor executable program instructions, wherein the data and instructions jointly configure and program the apparatus that the instructions when executed by the processor cause the apparatus to perform operations comprising:
  receive a service offer from a service provider; and
  construct in the memory a digital asset token for the service offer, the digital asset token comprising:
    a header, encoding:
      an immutable asset identifier representing the service offer, wherein the asset identifier is unique within a predetermined namespace;
      an immutable asset exchange identifier, wherein the exchange identifier is unique within a predetermined namespace;
      an immutable asset creation time representing the time at which the digital asset token was constructed;
      a mutable asset state value selected from the group consisting of minting, issued, trading, sold, redeemed, and burned;
    a payload, encoding:
      the service offer;
      a copy of the asset identifier encoded by the header;
      the hash of the header;
      a reference to a plurality of related asset bundles, wherein each asset bundle of the plurality of related asset bundles comprises at least one healthcare asset;
      a reference to at least one contract defining provision terms of the related asset bundles, wherein the at least one contract comprises one or more subcontract encoding a location, time, facility, and professional resource allocated to provide each of the at least one healthcare asset of the related asset bundles;
      an asset class determined as a function of contract status;
      a nonce; and
    send the header without the payload to an asset exchange identified by the asset exchange identifier, and send the payload without the header to an application server.

23. The apparatus of claim 22, wherein the operations performed by the apparatus further comprise: receive a digital asset token representing a certified service bundle digital asset having a current degree of certification; determine if the status of at least one contract changed, based on contract status received in response to a contract status query comprising the asset identifier; in response to determining the status of the at least one contract changed, determine an updated asset degree of certification based on the fraction of the at least one contract that obligates at least one resource to provide at least one asset; and broadcast the updated asset degree of certification to a DL with the asset identifier.

24. The apparatus of claim 22, wherein the asset class determined as a function of contract status further comprises the asset class based on the fraction of subcontracts binding a party to provide an asset, and wherein the contract comprises a smart contract.

25. An apparatus comprising:
a processor; and
a memory configured to be operably coupled to the processor, wherein the memory comprises encoded data and processor executable program instructions, wherein the data and instructions jointly configure and program the apparatus that the instructions when executed by the processor cause the apparatus to perform operations comprising:
  receive a digital asset token representing a certified service bundle digital asset having a current asset degree of certification, wherein the received digital asset token encodes a reference to at least one contract of a plurality of contracts, and wherein the at least one contract obligates at least one resource to provide at least one service related to the service bundle digital asset;
  determine if the status of the at least one contract changed, based on updated contract status received in response to a query comprising a service bundle digital asset identifier that uniquely identifies the service bundle digital asset within a predetermined namespace;
  in response to determining the status of the at least one contract changed, determine an updated asset degree of certification that is distinct from the current degree of certification, wherein the updated asset degree of certification is based on the updated fraction of the at least one contract that obligates at least one resource to provide at least one service related to the service bundle; and
broadcast to a DL the updated asset degree of certification and the asset identifier.

26. The apparatus of claim 25, wherein the service bundle digital asset further comprises an asset class value determined as a function of the updated fraction of the at least one contract that obligates at least one resource to provide at least one service related to the service bundle.

27. The apparatus of claim 25, wherein the updated asset degree of certification represents an asset that is more fully certified than the current asset degree of certification.

28. The apparatus of claim 25, wherein the digital asset token further comprises: a header; and a payload, wherein the payload comprises a copy of an identifier encoded by the header; and the operations performed by the apparatus to receive the digital asset token further comprise: associate, based on the identifier, the header received without the payload from a first application server with the payload received without the header from a second application server.

* * * * *